(12) United States Patent
Kadam et al.

(10) Patent No.: US 9,458,173 B2
(45) Date of Patent: Oct. 4, 2016

(54) AMIDES OF 2-AMINO-4-ARYLTHIAZOLE COMPOUNDS AND THEIR SALTS

(71) Applicant: GLENMARK PHARMACEUTICALS S.A., La Chaux-de-fonds (CH)

(72) Inventors: Suresh Mahadev Kadam, Thane (West) (IN); Abraham Thomas, Navi Mumbai (IN); Sukumar Sinha, Navi Mumbai (IN); Sukeerthi Kumar, Navi Mumbai (IN); Bipin Parsottam Kansagra, Navi Mumbai (IN); Sachin Gavhane, Thane (IN); Sandeep Bandu Khandagale, Shrirampur (IN); Shailesh Pawase, Mumbai (IN); Jayant Prakashrao Patil, Nasik (IN); Shailendra Bhadane, Jalgaon (IN); Bhavna Mishra, Navi Mumbai (IN); Rajesh Dwivedi, Navi Mumbai (IN)

(73) Assignee: GLENMARK PHARMACEUTICALS S.A., La Chaux-de-Fonds (CH)

( * ) Notice: Subject to any disclaimer, the term of this patent is extended or adjusted under 35 U.S.C. 154(b) by 124 days.

(21) Appl. No.: 14/402,608

(22) PCT Filed: Jun. 8, 2013

(86) PCT No.: PCT/IB2013/054703
§ 371 (c)(1),
(2) Date: Nov. 20, 2014

(87) PCT Pub. No.: WO2013/183035
PCT Pub. Date: Dec. 12, 2013

(65) Prior Publication Data
US 2015/0111038 A1    Apr. 23, 2015

Related U.S. Application Data

(60) Provisional application No. 61/665,282, filed on Jun. 27, 2012, provisional application No. 61/748,016, filed on Dec. 31, 2012.

(30) Foreign Application Priority Data

Jun. 8, 2012   (IN) .......................... 1687/MUM/2012
Dec. 13, 2012  (IN) .......................... 3519/MUM/2012

(51) Int. Cl.
C07D 495/04    (2006.01)
C07D 239/553   (2006.01)
C07D 239/60    (2006.01)

(52) U.S. Cl.
CPC ......... *C07D 495/04* (2013.01); *C07D 239/553* (2013.01); *C07D 239/60* (2013.01); *C07B 2200/13* (2013.01); *Y10T 428/2982* (2015.01)

(58) Field of Classification Search
CPC .............. C07D 495/04; C07D 239/60; C07D 239/553; C07B 2200/13; Y10T 428/2982

USPC ........................................... 428/402; 544/278
See application file for complete search history.

(56) References Cited

U.S. PATENT DOCUMENTS

| | | | |
|---|---|---|---|
| 6,028,074 A | 2/2000 | Cheshire et al. |
| 6,890,923 B2 | 5/2005 | Ingall et al. |
| 7,465,581 B2 | 12/2008 | Bevan et al. |
| 7,951,814 B2 | 5/2011 | Muthuppalniappan et al. |
| 8,163,761 B2 | 4/2012 | Ng et al. |
| 8,389,529 B2 | 3/2013 | Moran et al. |
| 8,507,503 B2 | 8/2013 | Kumar et al. |
| 8,575,178 B2 | 11/2013 | Kumar et al. |
| 8,592,398 B2 | 11/2013 | Kumar et al. |
| 8,623,880 B2 | 1/2014 | Chaudhari et al. |
| 8,987,278 B2 | 3/2015 | Kumar et al. |
| 2004/0038994 A1 | 2/2004 | Wilson |

(Continued)

FOREIGN PATENT DOCUMENTS

| EP | 1657238 | * | 5/2006 |
|---|---|---|---|
| EP | 1657238 A1 | | 5/2006 |

(Continued)

OTHER PUBLICATIONS

International Search Report dated Dec. 17, 2013, for corresponding International Patent Application No. PCT/IB2013/054703.

(Continued)

*Primary Examiner* — Leszek Kiliman
(74) *Attorney, Agent, or Firm* — Pergament & Cepeda LLP; Milagros A. Cepeda; Edward D. Pergament

(57) ABSTRACT

The present disclosure is directed to salts of N-{4-[2,4-difluoro-3-(trifluoromethyl)phenyl]-1,3-thiazol-2-yl}dimethyl-2,4-dioxo-1,2,3,4-tetrahydrothieno[2,3-d]pyrimidin-5-yl)acetamide and process for the preparation thereof (formula II).

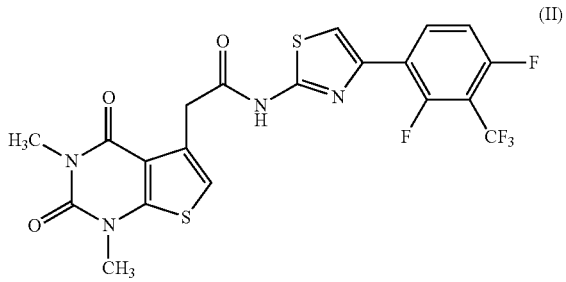

28 Claims, 17 Drawing Sheets

(56) References Cited

U.S. PATENT DOCUMENTS

| | | |
|---|---|---|
| 2005/0070558 A1 | 3/2005 | Vidal Juan et al. |
| 2007/0032531 A1 | 2/2007 | Smith et al. |
| 2007/0099940 A1 | 5/2007 | Spearing |
| 2007/0105920 A1 | 5/2007 | Palin et al. |
| 2007/0196866 A1 | 8/2007 | Patapoutian et al. |
| 2009/0062258 A1 | 3/2009 | Hamamura et al. |
| 2009/0233907 A1 | 9/2009 | Austin et al. |
| 2009/0325987 A1* | 12/2009 | Muthuppalniappan ............... C07D 239/96 514/266.21 |
| 2012/0178766 A1 | 7/2012 | Chaudhari et al. |
| 2014/0128603 A1 | 5/2014 | Chaudhari et al. |

FOREIGN PATENT DOCUMENTS

| | | |
|---|---|---|
| GB | 1445697 | 8/1976 |
| WO | WO03000694 * | 1/2003 |
| WO | WO2004/014916 * | 2/2004 |
| WO | WO2007/073505 * | 6/2007 |
| WO | 2008/094909 A2 | 8/2008 |
| WO | WO2009/002933 * | 12/2008 |
| WO | 2009/158719 A2 | 12/2009 |
| WO | WO2010/109329 * | 9/2010 |
| WO | WO2010/109334 * | 9/2010 |

OTHER PUBLICATIONS

Written Opinion dated Dec. 17, 2013, for corresponding International Patent Application No. PCT/IB2013/054703.

International Preliminary Report on Patentability issued Dec. 9, 2014, for corresponding International Patent Application No. PCT/IB2013/054703.

MacPherson, et al., "Noxious compounds activate TRPA1 ion channels through covalent modification of cysteines", LETTERS, Nature, Feb. 1, 2007, pp. 541 to 545, vol. 445, Nature Publishing Group.

Childers et al., "Advances in the development of novel analgesics", Expert Opin. Ther. Patents, Sep. 1, 2008, pp. 1027-1067, vol. 18-issue No. 9, Informa UK Ltd.

L. Carroll King and Robert J. Hlavacek, "The Reaction of Ketones with Iodine and Thiourea", J. Am. Chem. Soc., Aug. 1950, pp. 3722-3725, vol. 72.

G. F. Duffin and J. D. Kendall, "The Reaction of Diazonium Salts with 1-Aryl-Δ2-pyrazolines", J. Chem. Soc., 1954, pp. 408-415.

H. Egg and I. Volgger, "A Convenient Synthesis of 1,3 Dialkyl-6-methyluracils and 1,3-Dialkyl-6-ethylthymines", Synthesis, Dec. 1982, pp. 1071-1073, Georg Thieme Verlag, Stuttgart, New York.

Satyanarayana et al., "Cycloaromatization of α-Oxoketene Dithioacetals with Enaminone Derived Carbanions", Tetrahedron Letters, 1992, pp. 6173-6176, vol. 33-issue No. 41, Pergamon Press Ltd.

Hirota et al., "Convenient Synthesis of Pyrido[4,3-d]Pyrimidine-2,4-(1H,3H)-Diones", Heterocycles, 1998, pp. 871-882, vol. 47-issue No. 2.

Stephen B. McMahon and John N. Wood, "Increasingly Irritable and Close to Tears: TRPA1 in Inflammatory Pain", Cell, Mar. 24, 2006, pp. 1123-1125, vol. 124, Elsevier Inc.

Senda et al., "Pyrimidine Derivatives and Related Compounds. XII. The Vilsmeier Reaction of Barbituric Acid Derivatives and Uracil Derivatives", Yakugaku Zasshi, 1971, pp. 1372-1376, vol. 91-issue No. 12.

Dipak Prajapati and Jagir Singh Sandhu, "Studies on Pyrimidine-Annelated Heterocycles; 8. Intramolecular Cycloaddition of Thiophene and Nitrile Oxide or Nitrone Groups Bonded to 1,3-Dimethyluracils", Synthesis, Apr. 1988, pp. 342-344.

Richard B. Silverman and Michael P. Groziak, "Model Chemistry for a Covalent Mechanism of Action of Orotidine 5'-Phosphate Decarboxylase", J. Am. Chem. Soc., 1982, pp. 6434-6439, vol. 104-issue No. 23, American Chemical Society.

Story et al., "ANKTM1, a TRP-like Channel Expressed in Nociceptive Neurons, Is Activated by Cold Temperatures", Cell, Mar. 21, 2003, pp. 819-829, vol. 112, Cell Press.

Thomas L. Little and Stephen E. Webber, "A Simple and Practical Synthesis of 2-Aminoimidazoles", J. Org. Chem., 1994, pp. 7299-7305, vol. 59, American Chemical Society.

Tormyshev et al., "Aryl Alkyl Ketones in a One-Pot Gewald Synthesis of 2-Aminothiophenes", Synlett, 2006, pp. 2559-2564, issue No. 16, Georg Thieme Verlag Stuttgart, New York.

Voorhoeve et al., "A Genetic Screen Implicates miRNA-372 and miRNA-373 As Oncogenes in Testicular Germ Cell Tumors", Cell, Mar. 24, 2006, pp. 1169-1181, vol. 124, Elsevier Inc.

Wissenbach et al., "TRP channels as potential drug targets", Biology of the Cell, 2004, pp. 47-54, vol. 96, Elsevier SAS.

Hirota et al., "Pyrimidines. 65 [1]. Synthesis of 6-Substituted Thieno[2,3-d]pyrimidine-2,4(1H,3H)-diones", J. Heterocyclic Chem., Mar.-Apr. 1990, pp. 717-721, vol. 27.

Kotha et al., "A Simple Synthetic Approach to Allylated Aromatics via the Suzuki-Miyaura Cross-Coupling Reaction", Synlett, 2005, pp. 1877-1880, issue No. 12, Georg Thieme Verlag Stuttgart, New York.

Kennis et al., "New 2-Substituted 1,2,3,4-Tetrahydrobenzofuro[3,2-c]pyridine Having Highly Active and Potent Central α2-Antagonistic Activity as Potential Antidepressants", Bioorganic & Medicinal Chemistry Letters, 2000, pp. 71-74, vol. 10, Elsevier Science Ltd.

Mashraqui et al., "Dipyridyl/pyridinium thieno[2,3-b]thiophenes as new atropisomeric systems. Synthesis, conformational analysis and energy minimization", Tetrahedron, 2005, pp. 3507-3513, vol. 61, Elsevier Ltd.

Mohler et al., "A Facile Synthesis of Homologous 4,4'-Dialkanoic Acid Substituted 2,2'-Bipyridines", Synthesis, 2002, pp. 745-748, issue No. 6, Georg Thieme Verlag Stuttgart, New York.

He et al., "Conformational Color Polymorphism and Control of Crystallization of 5-Methyl-2-[(4-methyl-2-nitrophenyl)amino]-3-thiophenecarbonitrile", Journal of Pharmaceutical Sciences, Mar. 2001, pp. 371-388, vol. 90-issue No. 3, Wiley-Liss, Inc. and the American Pharmaceutical Association.

Prakash et al., "N-Halosuccinimide/BF3-H2O, Efficient Electrophilic Halogenating Systems for Aromatics", J. Am. Chem. Soc., 2004, pp. 15770-15776, vol. 126-issue No. 48, American Chemical Society.

Postema et al., "Synthesis and Partial Biological Evaluation of a Small Library of Differentially-Linked β-C Disaccharides", J. Org. Chem., 2003, pp. 4748-4754, vol. 68-issue No. 12, American Chemical Society.

Tsupak et al., "Pyrrolopyrimidines. 5. Reaction Of 6-Amino-1,3-Dimethylpyrrolo[3,4-d]Pyrimidine-2,4(1H,3H)-Diones With 1,3-Diketones", Chemistry of Heterocyclic Compounds, 2003, pp. 953-959, vol. 39-issue No. 7, Plenum Publishing Corporation.

Samir J. Naik and Uma P. Halkar, "Synthesis and application of novel 4,5,6,7-tetrahydrobenzothiazole based azo disperse dyes", ARKIVOC, 2005, pp. 141-149, vol. xiii, Arkat USA, Inc.

Toth et al., "Arachidonyl dopamine as a ligand for the vanilloid receptor VR1 of the rat", Life Sciences, 2003, pp. 487-498, vol. 73, Elsevier Science Inc.

McNamara et al., "TRPA1 mediates formalin-induced pain", PNAS, Aug. 14, 2007, pp. 13525-13530, vol. 104-issue No. 33, The National Academy of Sciences of the USA.

Press et al., "Furo[3,4-d]pyrimidine-2,4-dione derivatives with antihypertensive activity. Analogues of thienopyrimidine-2,4-diones", Eur. J. Med. Chem., 1989, pp. 627-630, vol. 24, Elsevier, Paris.

Sladowska et al., "Synthesis and pharmacological properties of N, N-dialkyl(dialkenyl)amides of 7-methyl-3-phenyl-1-[2-hydroxy-3-(4-phenyl-1-piperazinyl)propyl]-2-4-dioxo-1,2,3,4-tetrahydropyrido-[2,3-d]pyrimidine-5-carboxylic acid", Farmaco, Jan. 2003, pp. 25-32, vol. 58-issue No. 1, Elsevier SAS.

International Search Report and Written Opinion dated Aug. 26, 2010 for International Patent Application No. PCT/IB2010/000553.

International Search Report and Written Opinion dated Oct. 6, 2010 for International Patent Application No. PCT/IB2010/000930.

(56) References Cited

OTHER PUBLICATIONS

International Search Report and Written Opinion dated Jun. 28, 2010 for International Patent Application No. PCT/IB2010/000834.
International Search Report and Written Opinion dated Jun. 28, 2010 for International Patent Application No. PCT/IB2010/000840.
International Search Report and Written Opinion dated Sep. 20, 2010 for International Patent Application No. PCT/IB2010/001073.
Extended European Search Report dated Jul. 4, 2013 for corresponding European Application No. EP 13 00 2731.
Extended European Search Report dated Jul. 2, 2012 for corresponding European Application No. EP 10 75 5503.
Non-Final Office Action mailed by the USPTO on Jun. 17, 2014, for U.S. Appl. No. 13/925,975.
Non-Final Office Action mailed by the USPTO on Nov. 5, 2012, for U.S. Appl. No. 12/936,451.

* cited by examiner

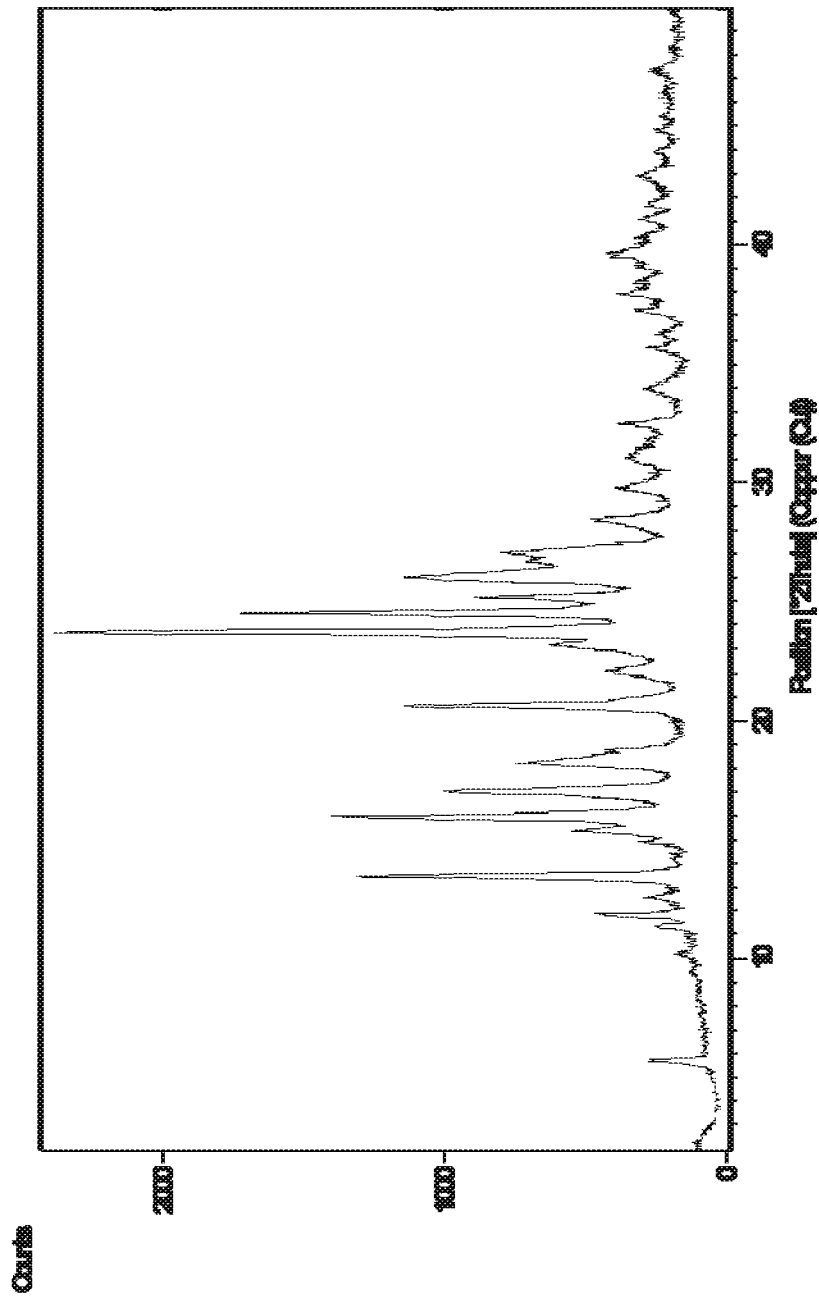
Fig.1: XRPD Pattern of Form I

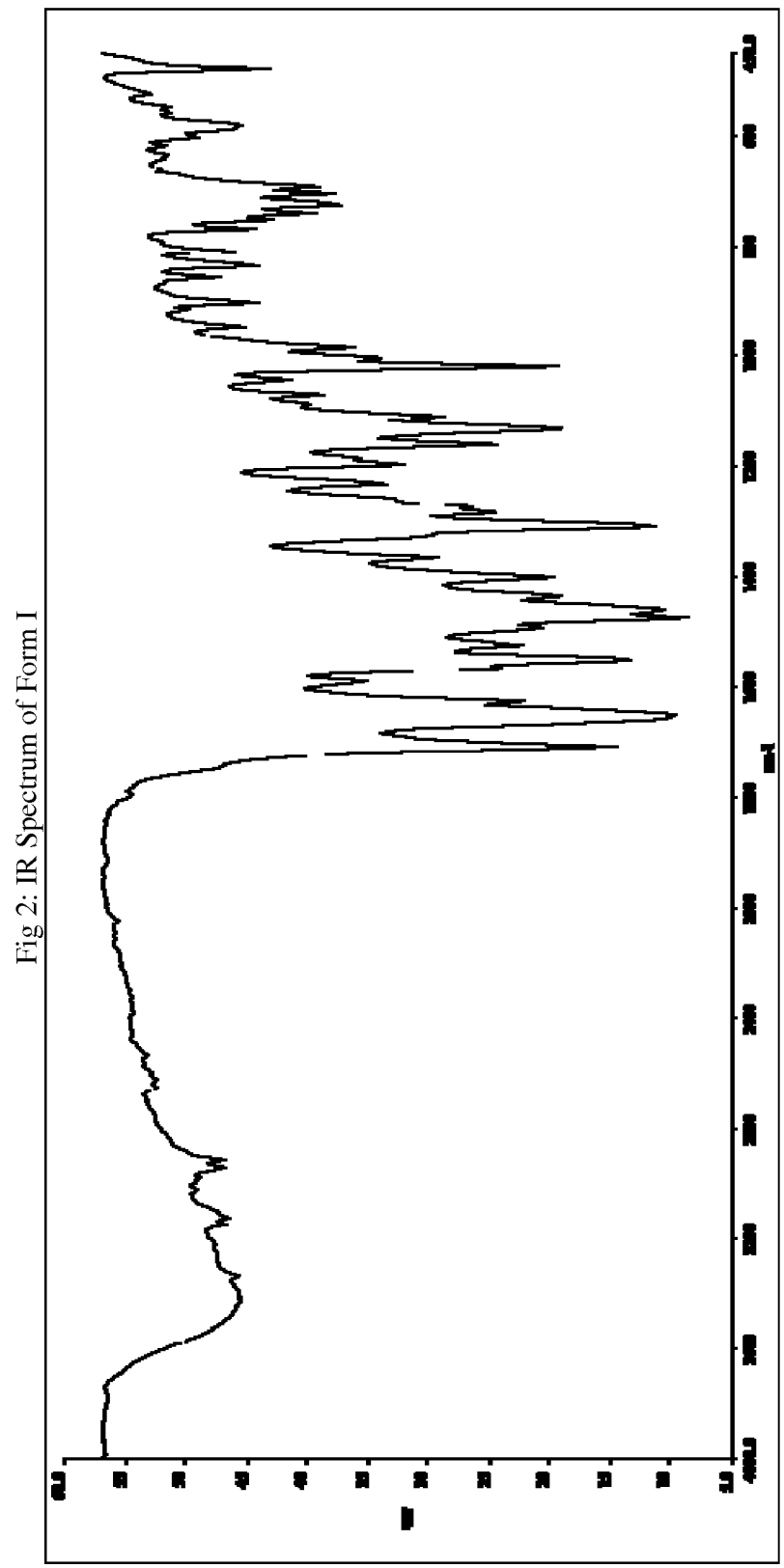
Fig 2: IR Spectrum of Form I

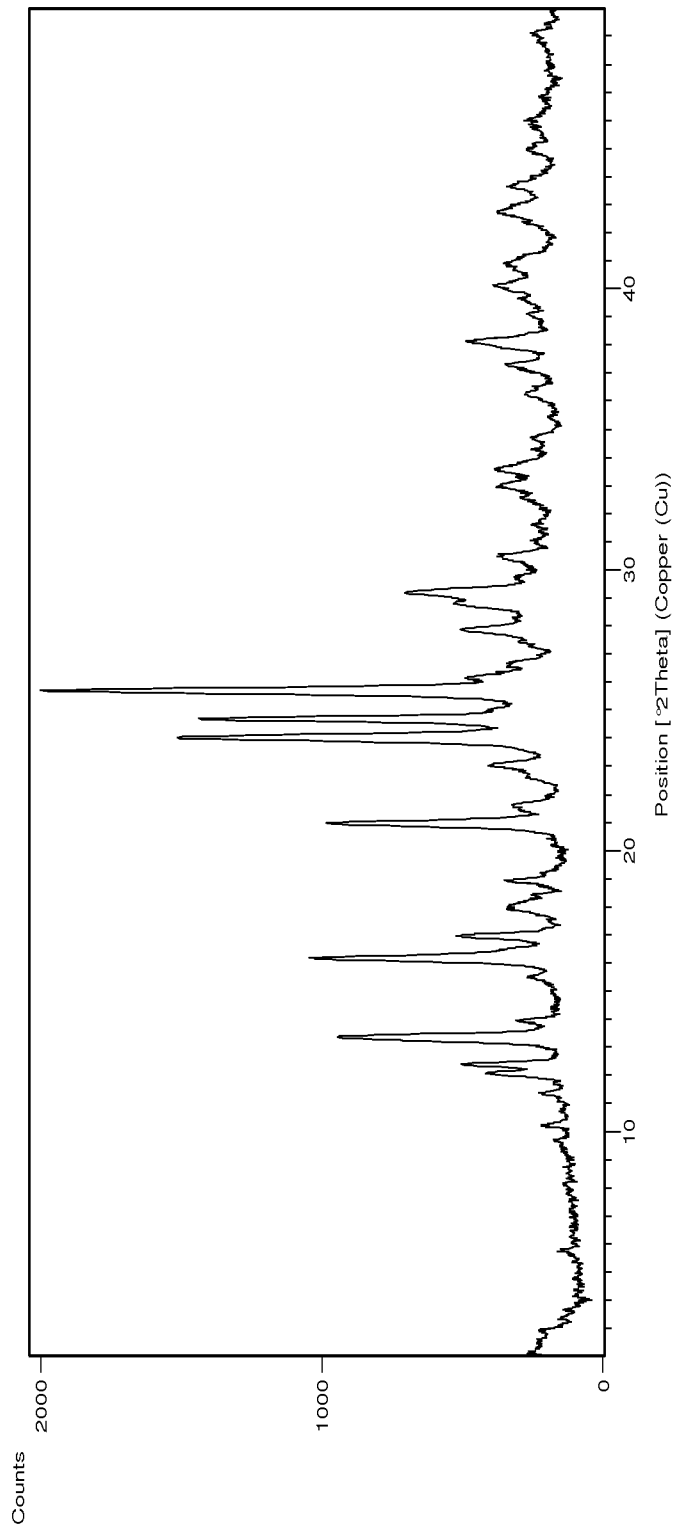
Fig 3: XRPD Pattern of Form II

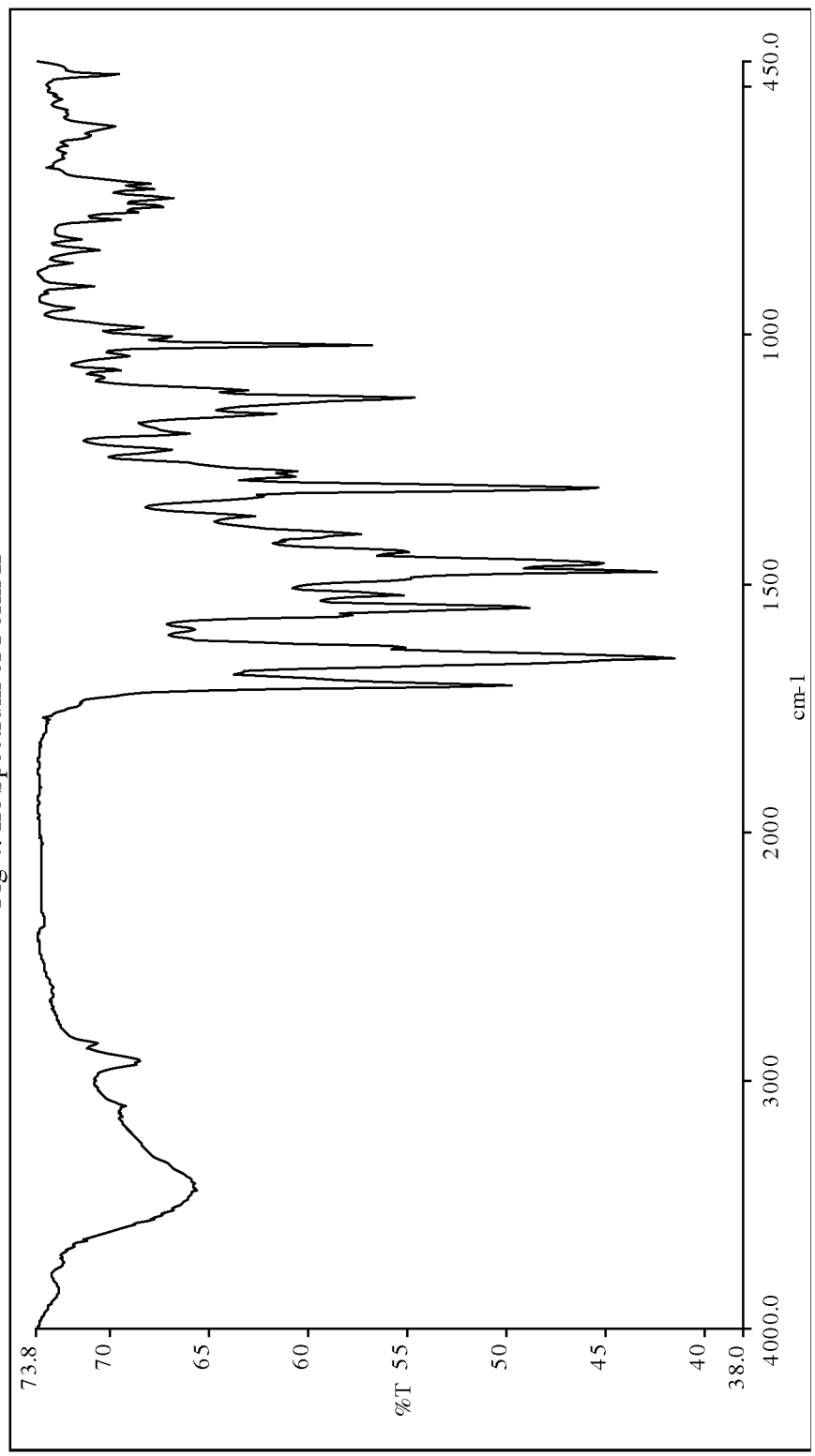

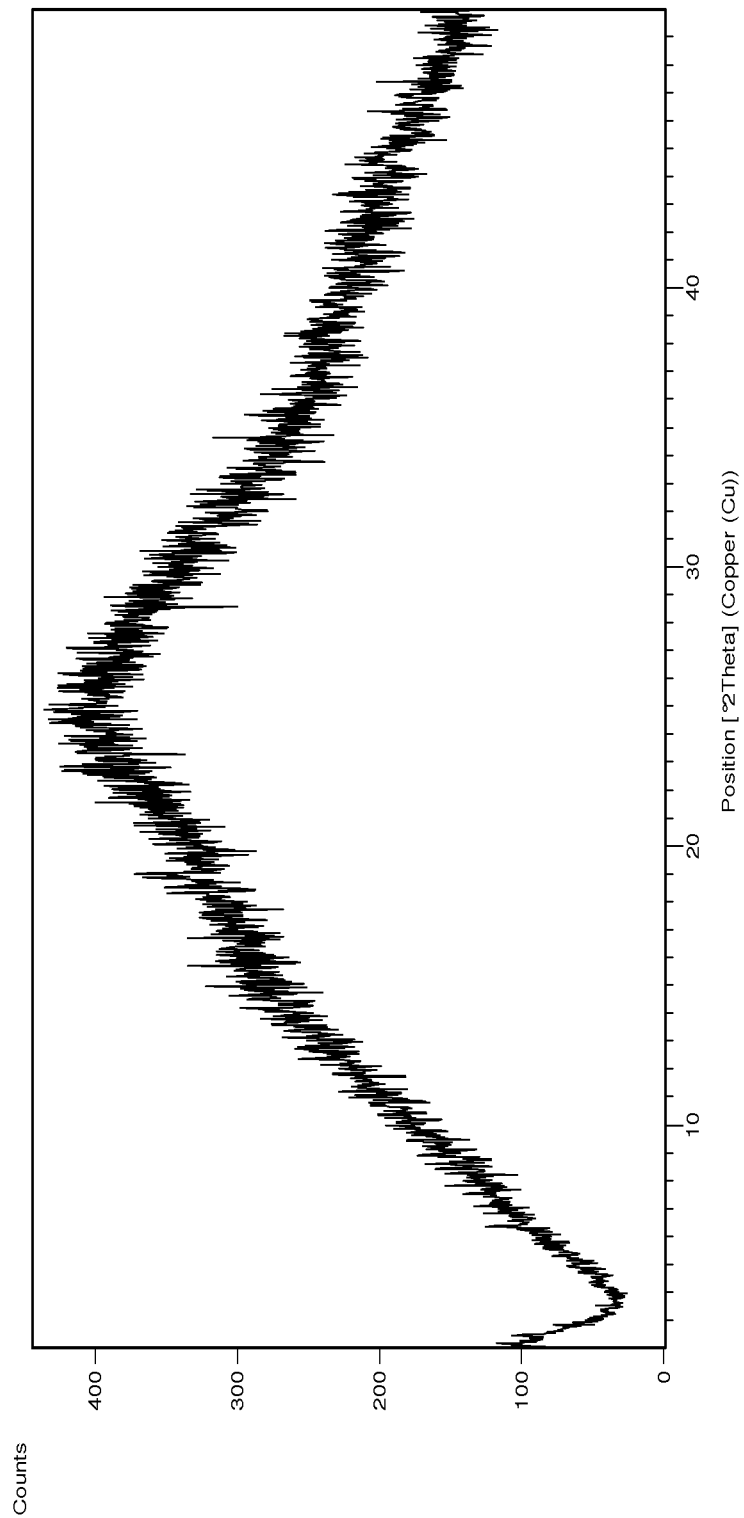
Fig 5: XRPD Pattern of amorphous potassium salt of compound of formula (II)

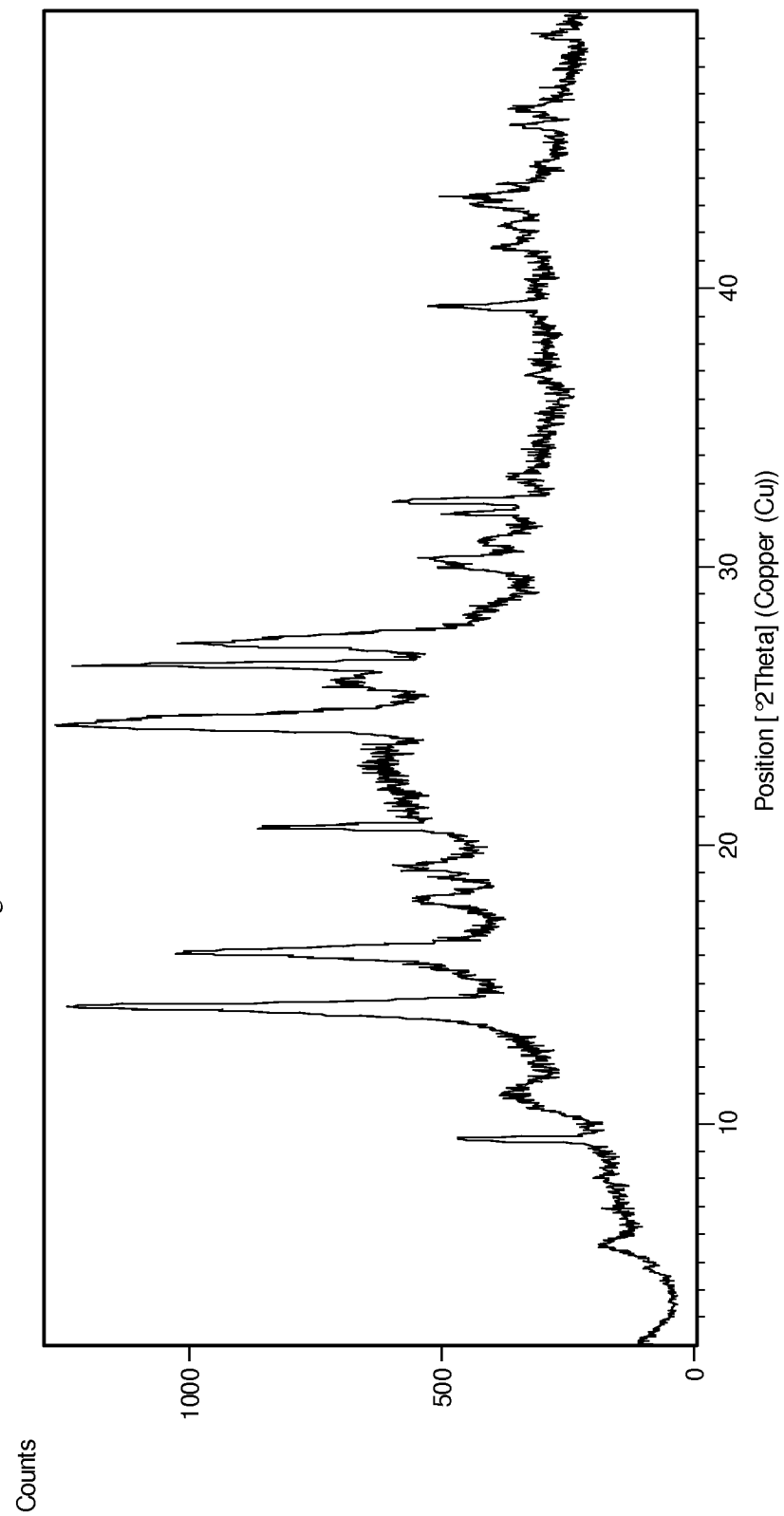
Fig 6: XRPD Pattern of Form A

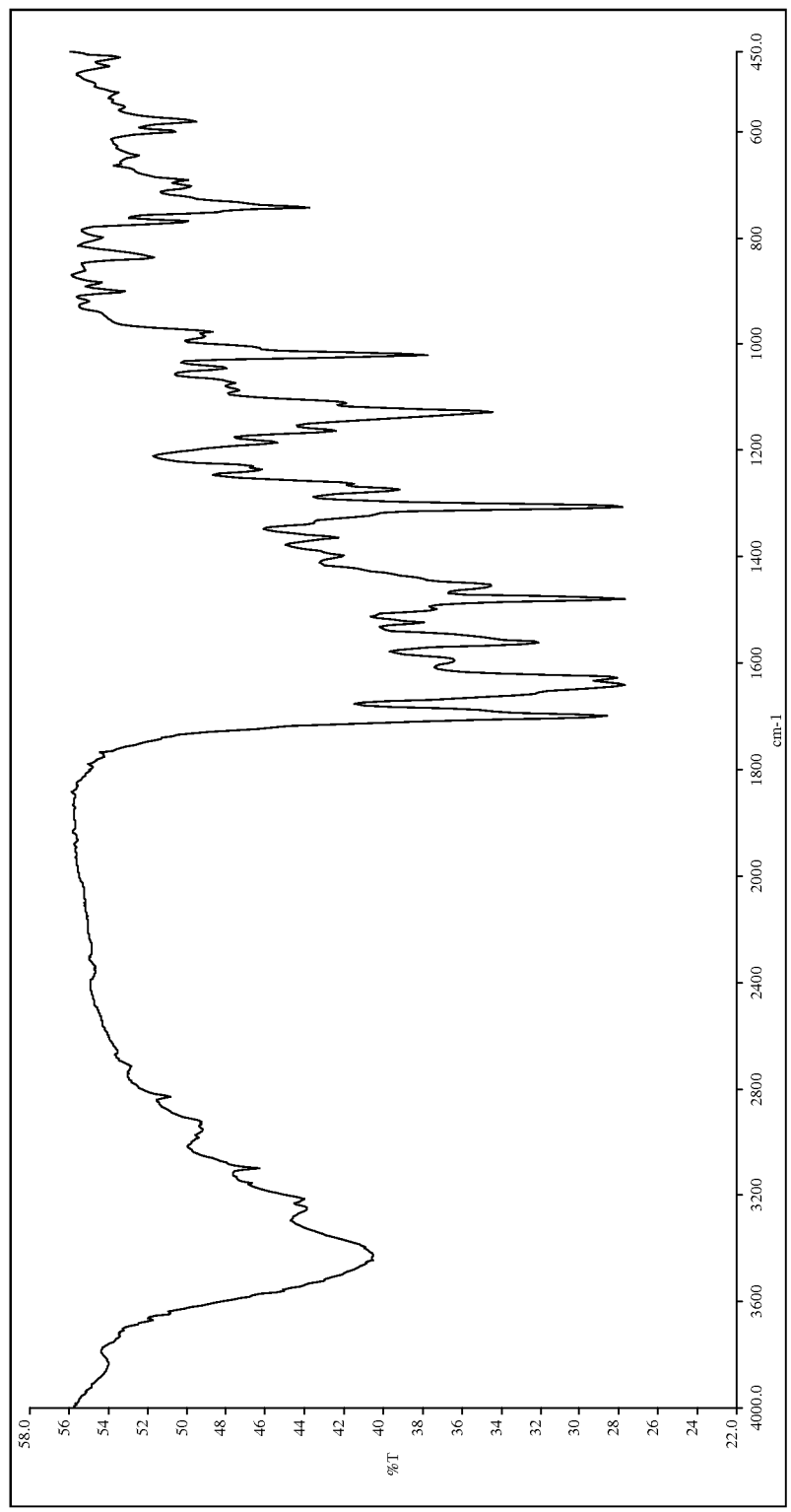
Fig 7: IR Spectrum of Form A

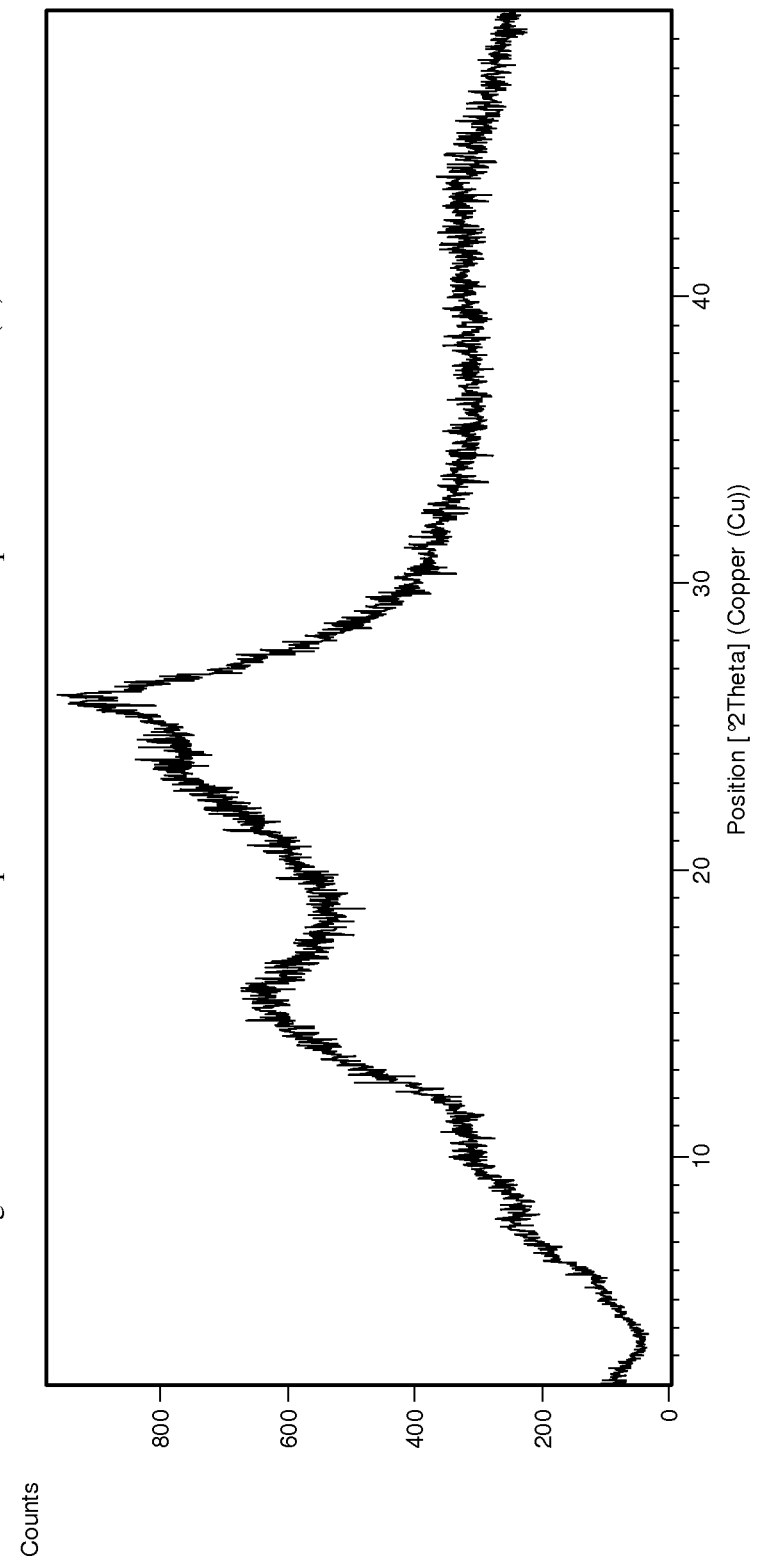
Fig 8: XRPD Pattern of amorphous sodium salt of compound of formula (II)

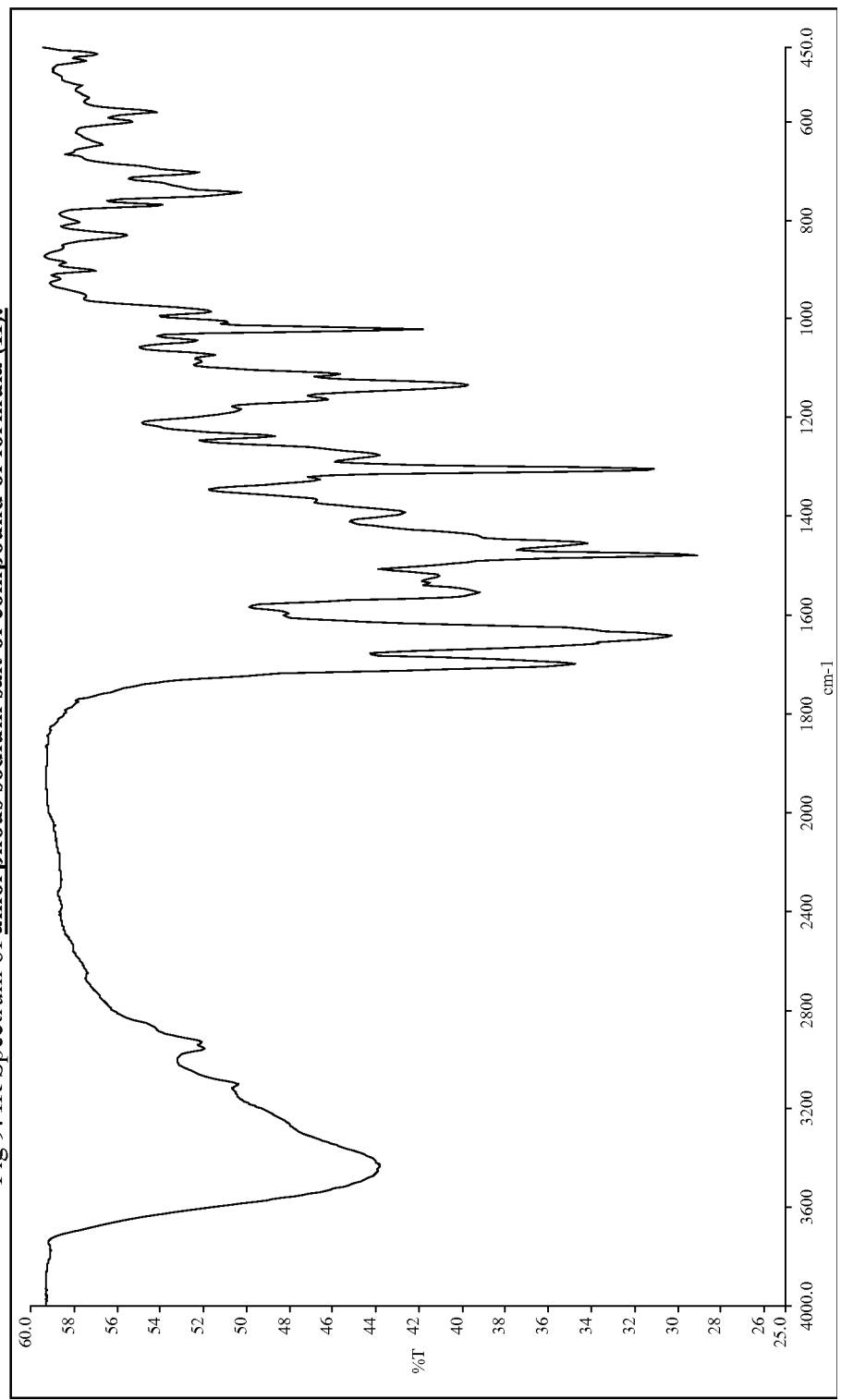
Fig 9: IR Spectrum of amorphous sodium salt of compound of formula (II).

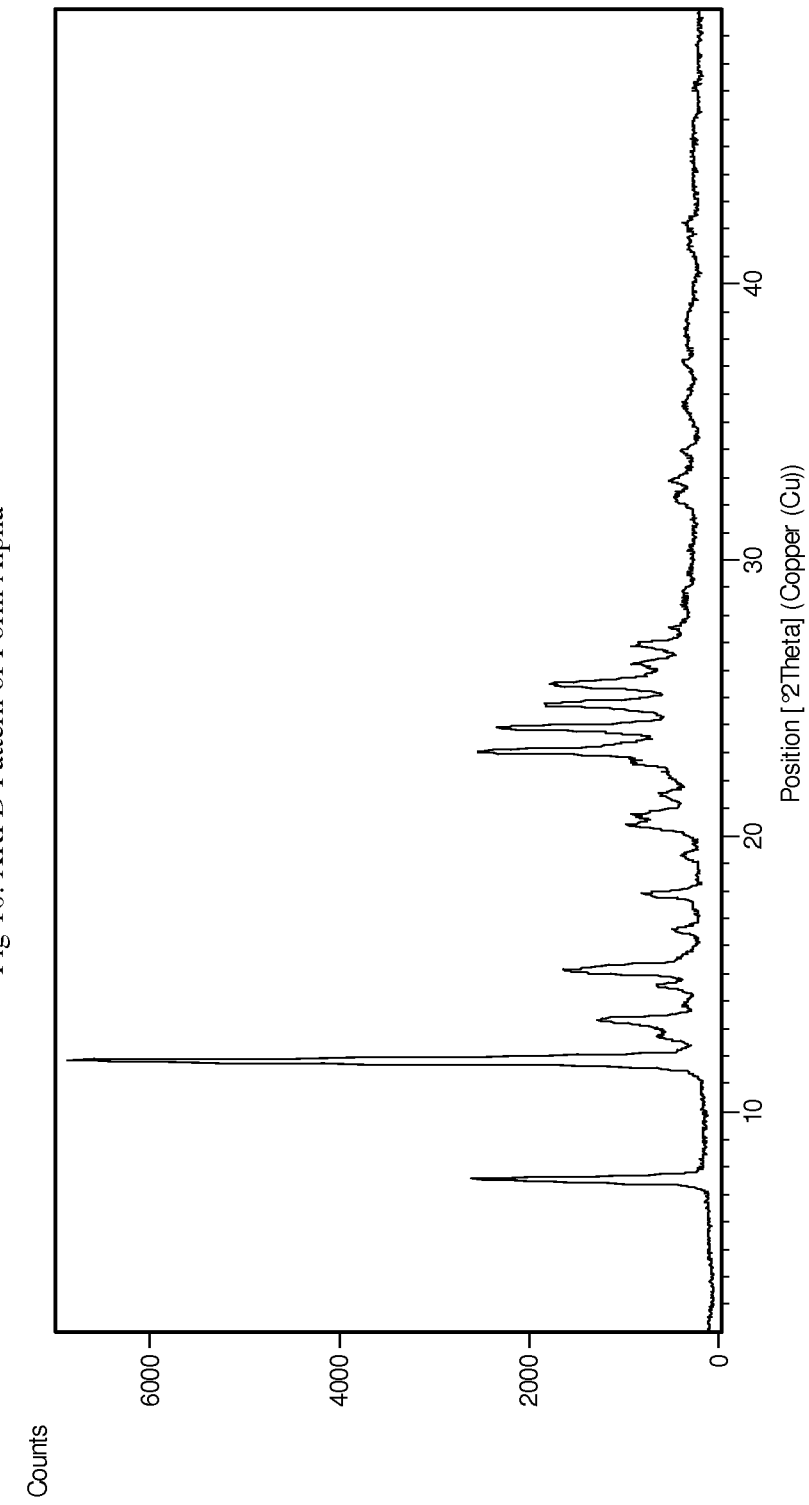

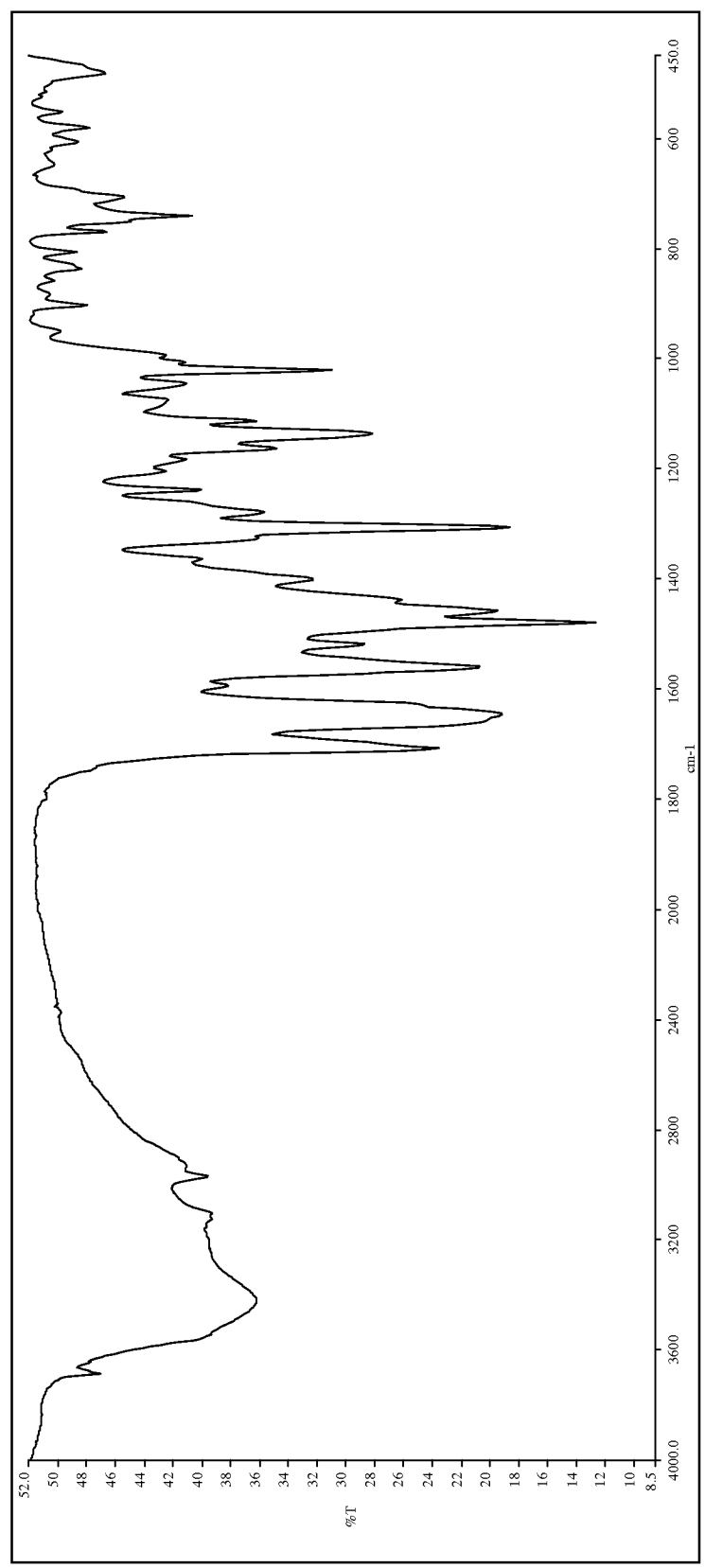
Fig 11: IR Spectrum of Form Alpha

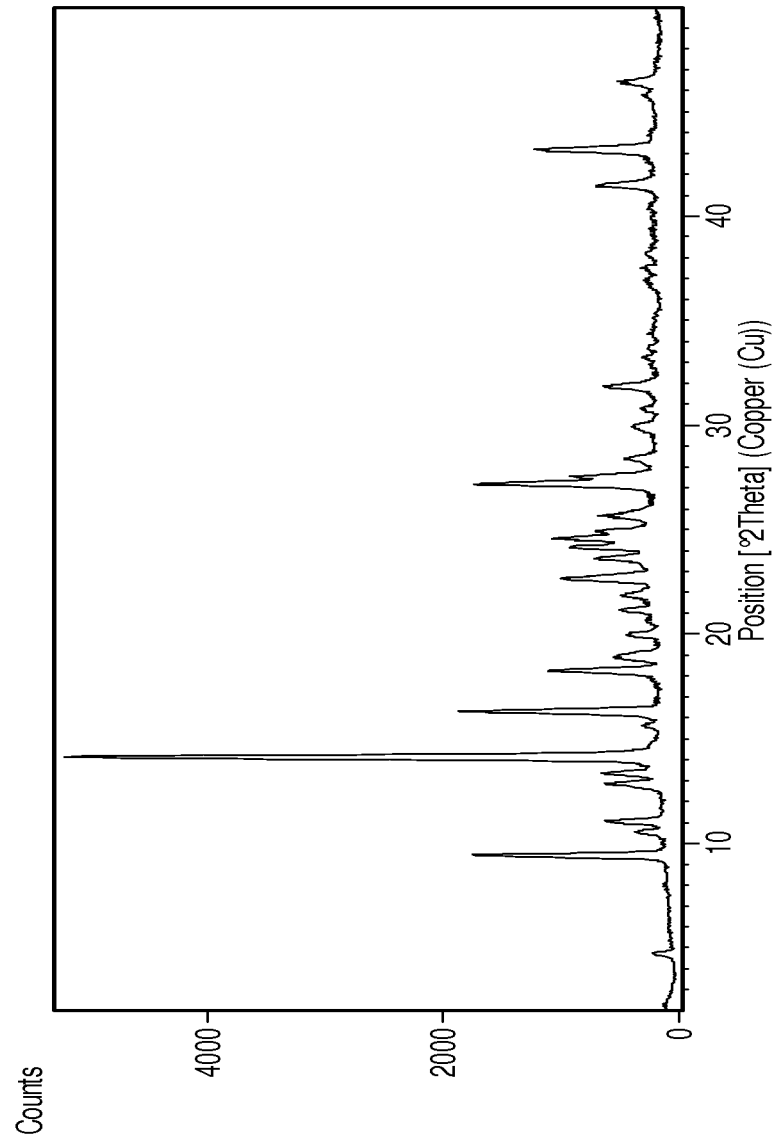
Fig.12: XRPD Pattern of Form X

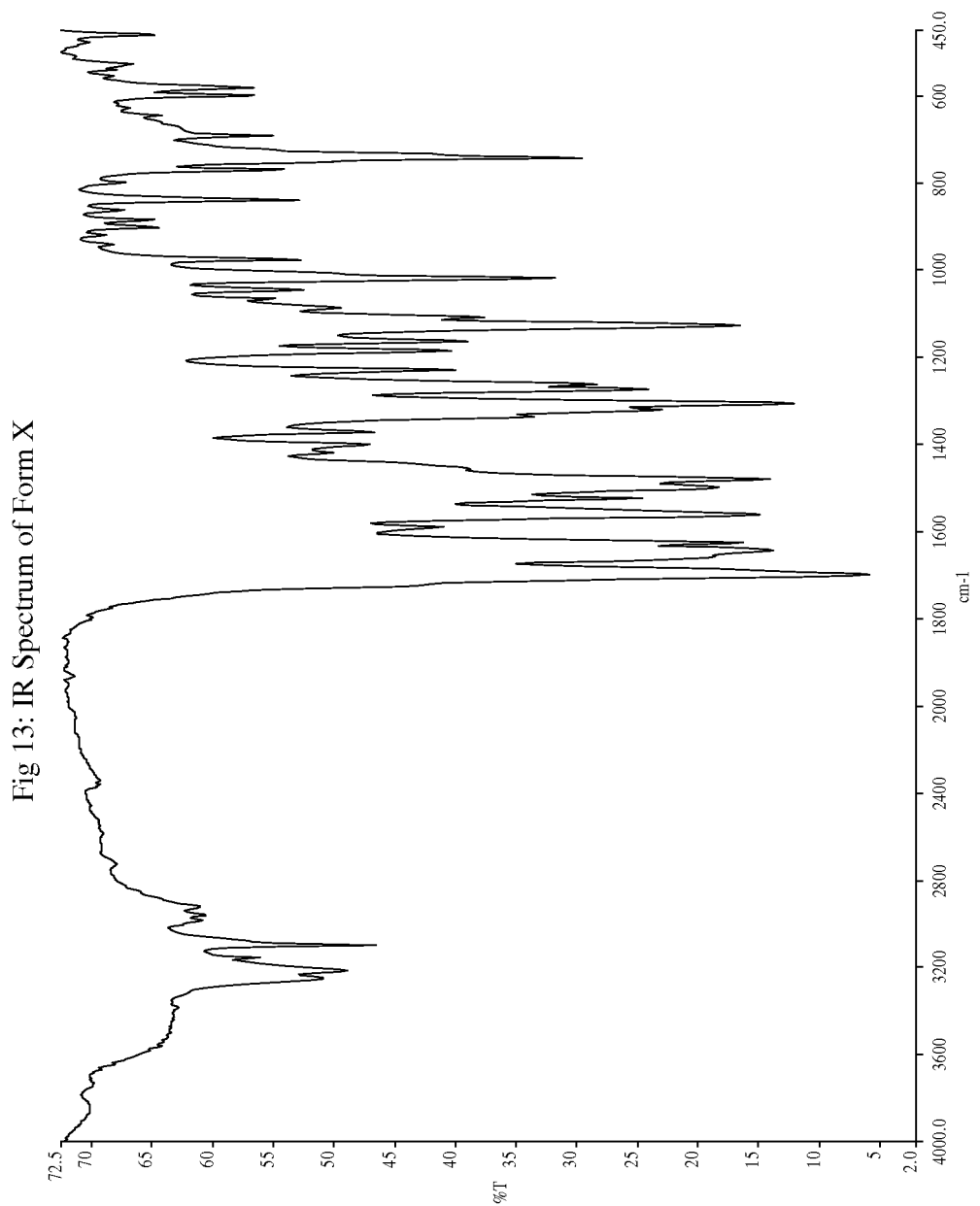
Fig 13: IR Spectrum of Form X

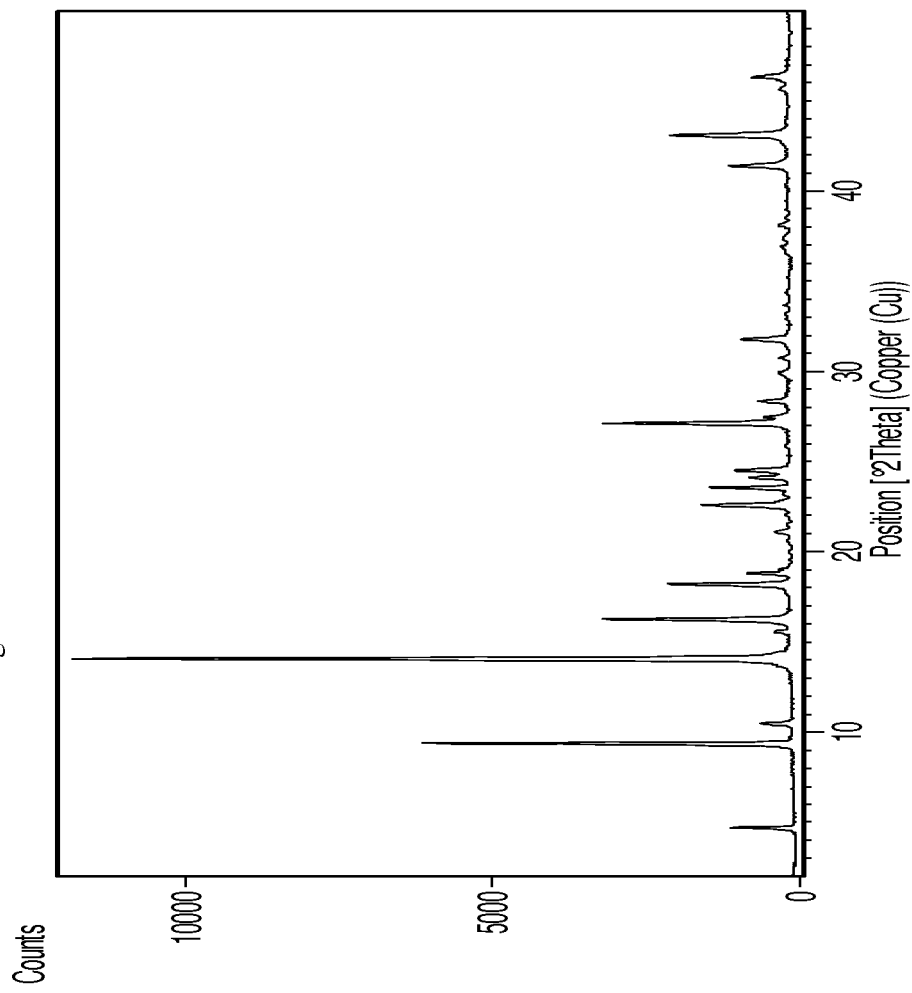

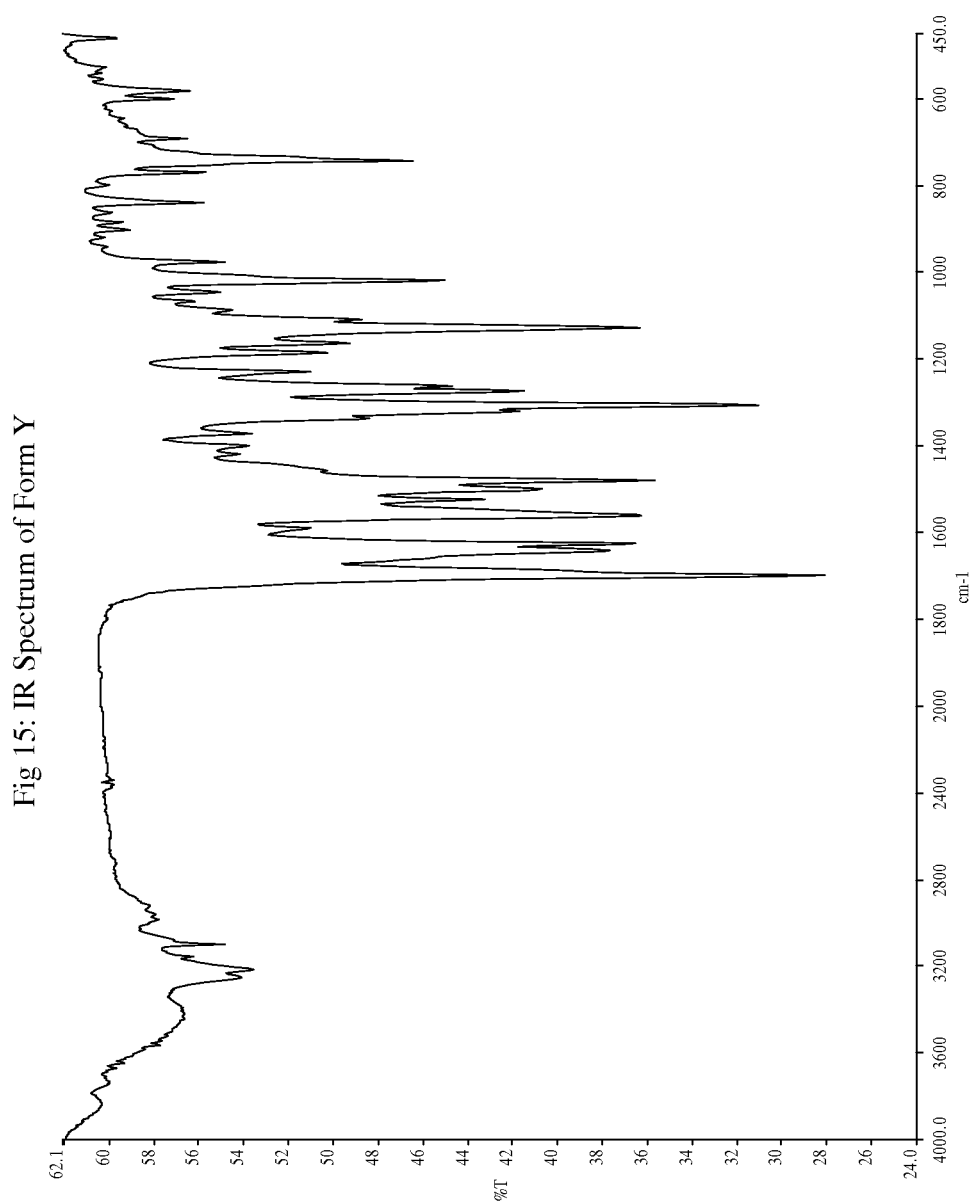
Fig 15: IR Spectrum of Form Y

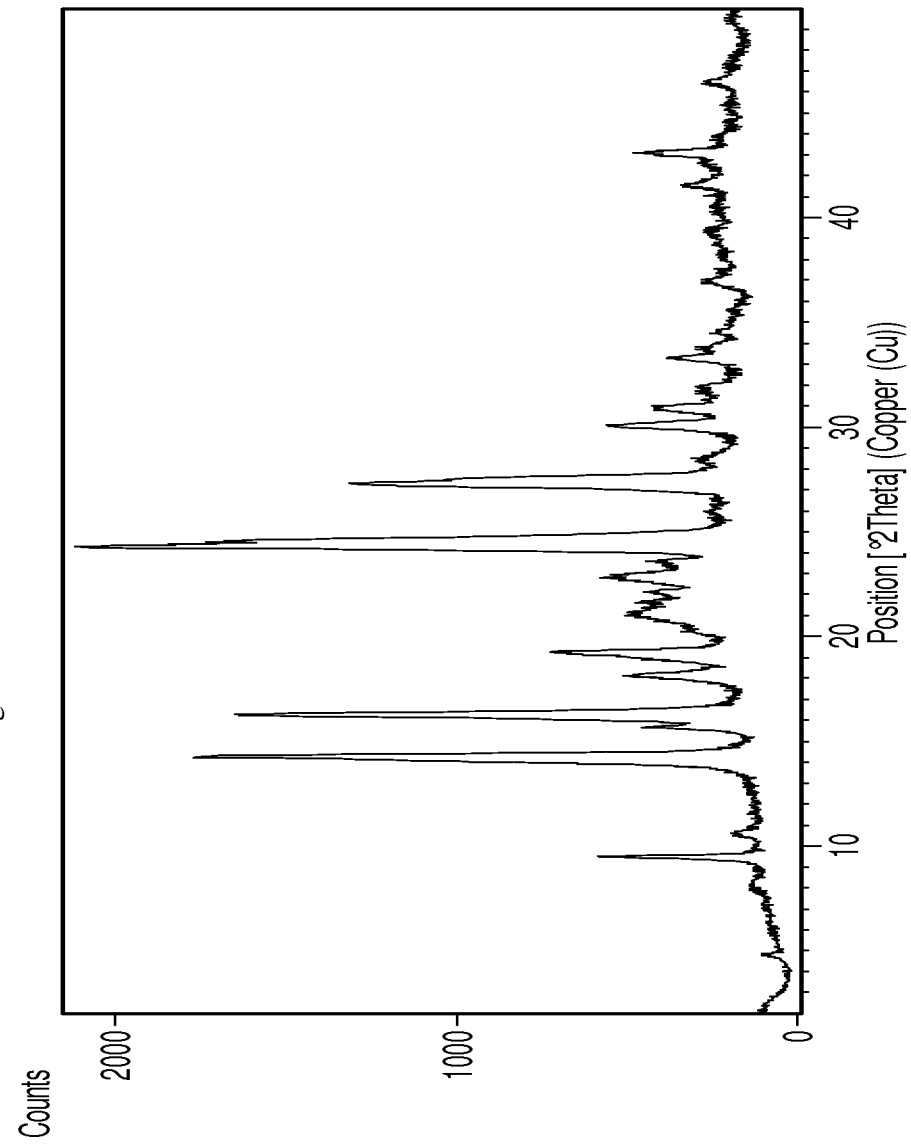
Fig 16: XRPD Pattern of Form Z

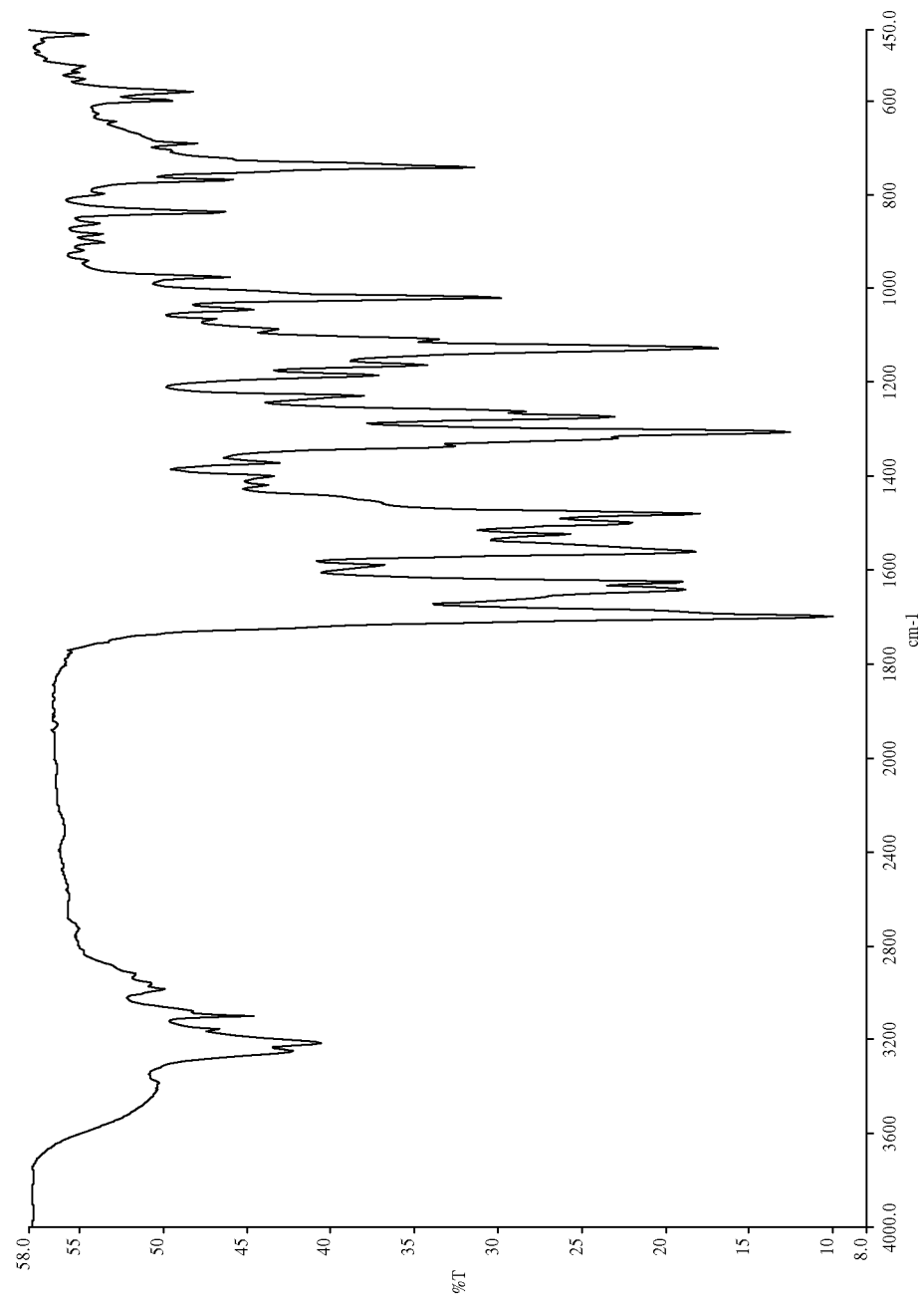

AMIDES OF 2-AMINO-4-ARYLTHIAZOLE COMPOUNDS AND THEIR SALTS

RELATED APPLICATIONS

This application is a National Stage Application under 35 U.S.C. §371 of PCT International Application No. PCT/IB2013/054703 filed Jun. 8, 2013 which claims the benefit of Indian Provisional Application Nos. 1687/MUM/2012 filed on Jun. 8, 2012 and 3519/MUM/2012 filed on Dec. 13, 2012; and US Provisional Application Nos. 61/665,282 filed on Jun. 27, 2012 and 61/748,016 filed on Dec. 31, 2012, all of which are hereby incorporated by reference in their entireties.

TECHNICAL FIELD

The present application relates to salts of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide and process for the preparation thereof.

BACKGROUND OF THE INVENTION

It is believed transient receptor potential ankyrinl (TRPA1) is expressed in nociceptive neurons. Nociceptive neurons of the nervous system sense the peripheral damage and transmit pain signals. TRPA1 is membrane bound and most likely acts as a heterodimeric voltage gated channel. It is believed to have a particular secondary structure, its N-terminus is lined with a large number of ankyrin repeats which are believed to form a spring-like edifice. TRPA1 is activated by a variety of noxious stimuli, including cold temperatures (activated at 17° C.), pungent natural compounds (e.g., mustard, cinnamon and garlic) and environmental irritants (MacPherson L J et al, *Nature*, 2007, 445; 541-545). Noxious compounds activate TRPA1 ion channels through covalent modification of cysteines to form covalently linked adducts. Variety of endogenous molecules produced during tissue inflammation/injury have been identified as pathological activators of TRPA1 receptor. These include hydrogen peroxide which is produced due to oxidative stress generated during inflammation, alkenyl aldehyde 4-HNE—an intracellular lipid peroxidation product and cyclopentenone prostaglandin 15dPGJ2 which is produced from PGD2 during inflammation/allergic response. TRPA1 is also activated in receptor dependant fashion by Bradykinin (BK) which is released during tissue injury at peripheral terminals.

International PCT publication number WO 2010/109334 discloses thienopyrimidinedione compounds of formula (I) which are shown to be having TRPA1 inhibition activity. Thus, the compounds of formula (I) may be useful for the treatment of diseases, conditions and/or disorders modulated by TRPA1.

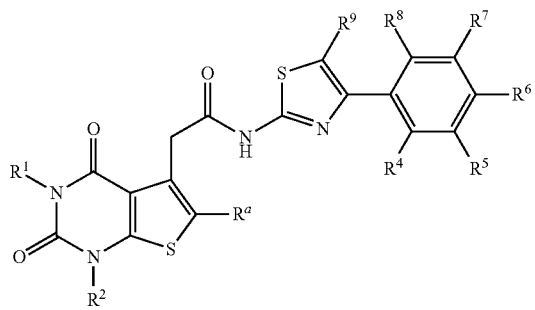

wherein, $R^1$, $R^2$ and $R^3$, which may be the same or different, are each independently hydrogen or $(C_1-C_4)$alkyl;

$R^4$, $R^5$, $R^6$, $R^7$, $R^8$ and $R^9$, which may be same or different, are each independently selected from the group comprising of hydrogen, halogen, cyano, hydroxyl, nitro, amino, $(C_1-C_6)$alkyl, $(C_1-C_6)$alkoxy, halo$(C_1-C_6)$alkyl, halo$(C_1-C_6)$alkoxy, $(C_3-C_6)$cycloalkyl, $(C_3-C_6)$cycloalkyl$(C_1-C_6)$alkyl and $(C_3-C_6)$cycloalkyl$(C_1-C_6)$alkoxy.

N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide, herein after designated as 'compound of formula (II), and its use for the treatment of TRPA1 mediated disorders was described in international publication number WO 2010/109334.

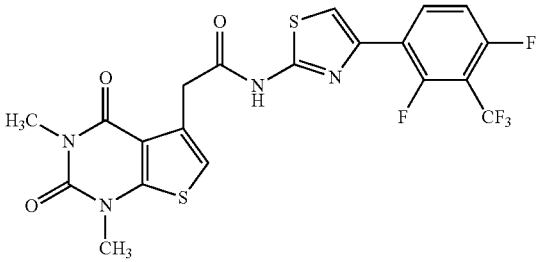

In the formulation of drug compositions, it is important for the active pharmaceutical ingredient to be in a form in which it can be conveniently handled and processed. Convenient handling is important not only from the perspective of obtaining a commercially viable manufacturing process, but also from the perspective of subsequent manufacture of pharmaceutical formulations comprising the active pharmaceutical ingredient. The drug development therefore involves research regarding finding suitable pharmaceutically acceptable salt forms of a drug. It may be also desirable to explore various polymorphs of these salts, which display better handling properties as well as it may also show improved physicochemical as well as pharmacokinetic and pharmacodynamic properties.

Further, development of a commercial drug candidate involves many steps, such as development of a cost effective synthetic method which is efficient in large scale manufacturing process.

SUMMARY OF THE INVENTION

The present application relates to salts of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide represented by formula (II)

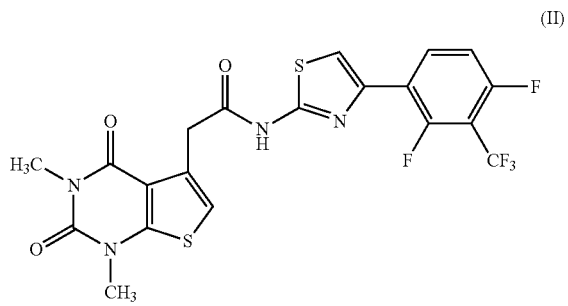 [SMILES: Cn1c(=O)c2c(CC(=O)Nc3nc(-c4ccc(F)c(C(F)(F)F)c4F)cs3)csc2n(C)c1=O]

(II)

and process for preparation thereof.

N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide, herein after designated as 'compound of formula (II)

In an embodiment, the present invention relates to potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide.

In another embodiment, the present invention relates to Potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide in crystalline form.

In yet another embodiment, potassium salt of a compound of formula (II) is provided in an amorphous form.

In yet another embodiment, the solid state forms of potassium salt of a compound of formula (II) exist in an anhydrous and/or solvent-free form or as a hydrate and/or a solvate form.

In another embodiment, there is provided a method for treating diseases, conditions and/or disorders modulated by TRPA1; comprising administering a solid state form of potassium salt of compound of formula (II), or a pharmaceutical composition that comprises the solid state form of potassium salt of compound of formula (II) along with pharmaceutically acceptable excipients.

In yet another embodiment, there is provided a method for treating diseases, conditions and/or disorders modulated by TRPA1; comprising administering crystalline potassium salt of compound of formula (II), or a pharmaceutical composition that comprises crystalline potassium salt of compound of formula (II) along with pharmaceutically acceptable excipients.

In an embodiment, there is provided potassium salt of a compound of formula (II) has water content less than about 5%.

In another embodiment, there is provided crystalline potassium salt of a compound of formula (II) having water content less than about 5%.

In another embodiment, there is provided potassium salt of compound of formula (II) having water content about 0.2-2.0% as determined by Karl Fischer method.

In another embodiment, there is provided potassium salt of compound of formula (II) having water content in the range of 0.2 to 1.0% as determined by Karl Fischer method.

In another embodiment, there is provided crystalline potassium salt of compound of formula (II) having water content about 0.2-2.0% as determined by Karl Fischer method.

In another embodiment, there is provided crystalline potassium salt of compound of formula (II) having water content in the range of 0.2 to 1.0% as determined by Karl Fischer method.

In another embodiment, there is provided the potassium salt of compound of formula (II) which exhibits the gradual increase of moisture content from initial value of about 0.80% to about 16.0% in 48 hours at 25° C./90% Relative Humidity (RH).

In another embodiment, there is provided crystalline potassium salt of compound of formula (II) which exhibits the gradual increase of moisture content from initial value of about 0.80% to about 16.0% in 48 hours at 25° C./90% Relative Humidity (RH).

In another embodiment, there is provided the potassium salt of compound of formula (II) which exhibits the gradual increase of moisture content from initial value of about 0.80% to about 6.6% in 48 hours at 25° C./80% RH.

In another embodiment, there is provided crystalline potassium salt of compound of formula (II) which exhibits the gradual increase of moisture content from initial value of about 0.80% to about 6.6% in 48 hours at 25° C./80% RH.

In another embodiment, there is provided the potassium salt of compound of formula (II) which exhibits the gradual increase of moisture content from initial value of about 0.80% to about 3.5% in 48 hours at 25° C./60% RH.

In another embodiment, there is provided the crystalline potassium salt of compound of formula (II) which exhibits the gradual increase of moisture content from initial value of about 0.80% to about 3.5% in 48 hours at 25° C./60% RH.

In another embodiment, there is provided the potassium salt of compound of formula (II) has an average particle size ($D_{50}$) in the range from about 1 μm to about 100 μm.

In yet another embodiment, there is provided the potassium salt of compound of formula (II) has an average particle size ($D_{50}$) in the range from about 1 μm to about 50 μm.

In yet another embodiment, there is provided potassium salt of compound of formula (II) has an average particle size ($D_{50}$) in the range from about 1 μm to about 20 μm.

In another embodiment, there is provided crystalline potassium salt of compound of formula (II) has an average particle size ($D_{50}$) in the range from about 1 μm to about 100 μm.

In yet another embodiment, there is provided the crystalline potassium salt of compound of formula (II) has an average particle size ($D_{50}$) in the range from about 1 μm to about 50 μm.

In yet another embodiment, there is provided the crystalline potassium salt of compound of formula (II) has an average particle size ($D_{50}$) in the range from about 1 μm to about 20 μm.

In another embodiment, there is provided the potassium salt of compound of formula (II) has about 10% of the particles ($D_{10}$) having size in the range from about 0.3 μm to about 10 μm.

In yet another embodiment, there is provided the potassium salt of compound of formula (II) has about 10% of the particles ($D_{10}$) having size in the range from about 0.5 μm to about 8 μm.

In yet another embodiment, there is provided the potassium salt of compound of formula (II) has about 10% of the particles ($D_{10}$) having size in the range from about 0.5 µm to about 5 µm.

In another embodiment, there is provided the crystalline potassium salt of compound of formula (II) has about 10% of the particles ($D_{10}$) having size in the range from about 0.3 µm to about 10 µm.

In yet another embodiment, there is provided the crystalline potassium salt of compound of formula (II) has about 10% of the particles ($D_{10}$) having size in the range from about 0.5 µm to about 8 µm.

In yet another embodiment, there is provided the crystalline potassium salt of compound of formula (II) has about 10% of the particles ($D_{10}$) having size in the range from about 0.5 µm to about 5 µm.

In another embodiment, there is provided the potassium salt of compound of formula (II) has about 90% of the particles ($D_{90}$) having size in the range from about 4 µm to about 300 µm.

In yet another embodiment, there is provided the potassium salt of compound of formula (II) has about 90% of the particles ($D_{90}$) having size in the range from about 5 µm to about 250 µm.

In yet another embodiment, there is provided the potassium salt of compound of formula (II) has about 90% of the particles ($D_{90}$) having size in the range from about 5 µm to about 200 µm.

In yet another embodiment, there is provided the potassium salt of compound of formula (II) has about 90% of the particles ($D_{90}$) having size in the range from about 5 µm to about 150 µm.

In another embodiment, there is provided the crystalline potassium salt of compound of formula (II) has about 90% of the particles ($D_{90}$) having size in the range from about 4 µm to about 300 µm.

In yet another embodiment, there is provided the crystalline potassium salt of compound of formula (II) has about 90% of the particles ($D_{90}$) having size in the range from about 5 µm to about 250 µm.

In yet another embodiment, there is provided the crystalline potassium salt of compound of formula (II) has about 90% of the particles ($D_{90}$) having size in the range from about 5 µm to about 200 µm.

In yet another embodiment, there is provided the crystalline potassium salt of compound of formula (II) has about 90% of the particles ($D_{90}$) having size in the range from about 5 µm to about 150 µm.

In another embodiment, the present invention also relates to substantially pure potassium salt of compound of formula (II). For the purposes of this invention, substantially pure is greater than about 90% pure.

In yet another embodiment, the present invention relates to substantially pure potassium salt of compound of formula (II) having purity greater than about 95%.

In yet another embodiment, the present invention relates to substantially pure potassium salt of compound of formula (II) having purity greater than about 98%.

In yet another embodiment, the present invention relates to substantially pure potassium salt of compound of formula (II) having purity greater than about 99%.

In another embodiment, the present invention also relates to substantially pure crystalline potassium salt of compound of formula (II). For the purposes of this invention, substantially pure is greater than about 90% pure.

In yet another embodiment, the present invention relates to substantially pure crystalline potassium salt of compound of formula (II) having purity greater than about 95%.

In yet another embodiment, the present invention relates to substantially pure crystalline potassium salt of compound of formula (II) having purity greater than about 98%.

In yet another embodiment, the present invention relates to substantially pure crystalline potassium salt of compound of formula (II) having purity greater than about 99%.

In another embodiment, the present invention relates to crystalline potassium salt of compound of formula (II) and process for the preparation thereof.

In yet another embodiment, the present invention relates to crystalline potassium salt of compound of formula (II).

In yet another embodiment, the present invention relates to process to prepare crystalline form of potassium salt of compound of formula (II).

In another embodiment, the present invention relates to crystalline form of potassium salt of compound of formula (II) which is designated as Form I.

In yet another embodiment, the present invention relates to process to prepare crystalline form of potassium salt of compound of formula (II) which is designated as Form I.

In another embodiment the present invention relates to crystalline form of potassium salt of compound of formula (II) which is designated as Form II.

In yet another embodiment the present invention relates to process for the preparation of crystalline form of potassium salt of compound of formula (II) designated as Form II.

In another embodiment, there is provided a method for treating diseases, conditions and/or disorders modulated by TRPA1; comprising administering Form I of potassium salt of compound of formula (II), or a pharmaceutical composition that comprises Form I of potassium salt of compound of formula (II) along with pharmaceutically acceptable excipients.

In another embodiment, there is provided a method for treating diseases, conditions and/or disorders modulated by TRPA1; comprising administering Form II of potassium salt of compound of formula (II), or a pharmaceutical composition that comprises Form II of potassium salt of compound of formula (II) along with pharmaceutically acceptable excipients.

In another embodiment, the present invention relates to amorphous potassium salt of compound of formula (II) and process for the preparation thereof.

In yet another embodiment, the present invention relates to amorphous potassium salt of compound of formula (II).

In yet another embodiment the present invention relates to process for the preparation of amorphous potassium salt of compound of formula (II).

In another embodiment, there is provided a method for treating diseases, conditions and/or disorders modulated by TRPA1; comprising administering amorphous form of potassium salt of compound of formula (II), or a pharmaceutical composition that comprises amorphous form of potassium salt of compound of formula (II) along with pharmaceutically acceptable excipients.

In another embodiment, the present invention relates to crystalline sodium salt of compound of formula (II) which is designated as Form A and process for the preparation thereof.

In yet another embodiment, the present invention relates to crystalline sodium salt of compound of formula (II) which is designated as Form A.

In yet another embodiment the present invention relates to process for the preparation of crystalline sodium salt of compound of formula (II) which is designated as Form A.

In another embodiment, there is provided a method for treating diseases, conditions and/or disorders modulated by TRPA1; comprising administering crystalline Form A of sodium salt of compound of formula (II), or a pharmaceutical composition that comprises crystalline Form A of sodium salt of compound of formula (II) along with pharmaceutically acceptable excipients.

In another embodiment, the present invention relates to amorphous sodium salt of compound of formula (II) and process for the preparation thereof.

In another embodiment, the present invention relates to amorphous sodium salt of compound of formula (II).

In yet another embodiment the present invention relates to process for the preparation of amorphous sodium salt of compound of formula (II).

In another embodiment, there is provided a method for treating diseases, conditions and/or disorders modulated by TRPA1; comprising administering amorphous sodium salt of compound of formula (II), or a pharmaceutical composition that comprises amorphous sodium salt of compound of formula (II) along with pharmaceutically acceptable excipients.

In another embodiment, the present invention relates to lithium salt of compound of formula (II).

In yet another embodiment the present invention relates to process for the preparation of lithium salt of compound of formula (II).

In another embodiment, the present invention relates to crystalline lithium salt of compound of formula (II) which may be designated as Form alpha and process for the preparation thereof.

In another embodiment, the present invention relates to crystalline lithium salt of compound of formula (II) which may be designated as Form alpha.

In yet another embodiment the present invention relates to process for the preparation of crystalline lithium salt of compound of formula (II) which may be designated as Form alpha.

In another embodiment, there is provided a method for treating diseases, conditions and/or disorders modulated by TRPA1; comprising administering lithium salt of compound of formula (II), or a pharmaceutical composition that comprises lithium salt of compound of formula (II) along with pharmaceutically acceptable excipients.

In another embodiment, there is provided a method for treating diseases, conditions and/or disorders modulated by TRPA1; comprising administering crystalline lithium salt of compound of formula (II), or a pharmaceutical composition that comprises crystalline lithium salt of compound of formula (II) along with pharmaceutically acceptable excipients.

The present application also relates to crystalline forms of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as compound of formula (II)

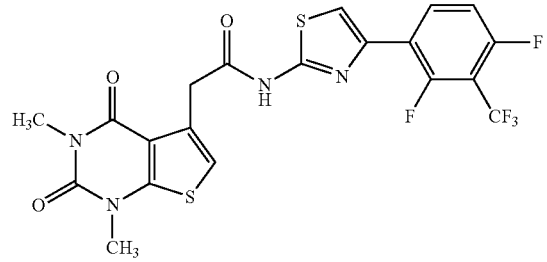

and process for preparation thereof.

In another embodiment, the crystalline forms of compound of formula (II) exist in an anhydrous and/or solvent-free form or as a hydrate and/or a solvate form.

In yet another embodiment there is provided a crystalline form of compound of formula (II) designated as Form X.

In yet another embodiment there is provided a process for the preparation of crystalline form of compound of formula (II) designated as Form X.

In yet another embodiment there is provided a crystalline form of compound of formula (II) designated as Form Y.

In yet another embodiment there is provided a process for the preparation of crystalline form of compound of formula (II) designated as Form Y.

In yet another embodiment there is provided a crystalline form of compound of formula (II), designated as Form Z.

In yet another embodiment there is provided a process for the preparation of crystalline form of compound of formula (II) designated as Form Z.

In another embodiment, there is provided a method for treating diseases, conditions and/or disorders modulated by TRPA1; comprising administering Form Y of compound of formula (II), or a pharmaceutical composition that comprises Form Y of compound of formula (II) along with pharmaceutically acceptable excipients.

In another embodiment, there is provided a method for treating diseases, conditions and/or disorders modulated by TRPA1; comprising administering Form Z of compound of formula (II), or a pharmaceutical composition that comprises Form Z of compound of formula (II) along with pharmaceutically acceptable excipients.

In yet another embodiment, there is provided crystalline compound of formula (II) having water content less than about 5%.

In yet another embodiment, there is provided crystalline compound of formula (II) having water content about 0.2-2.0% as determined by Karl Fischer method.

In yet another embodiment, there is provided crystalline compound of formula (II) having water content in the range 0.2 to 1.0% as determined by Karl Fischer method.

In another embodiment, there is provided crystalline compound of formula (II) having an average particle size ($D_{50}$) less than 100 µm, or preferably less than 50 µm, or more preferably less than 20 µm.

In another embodiment, there is provided crystalline compound of formula (II) having an average particle size ($D_{50}$) less than 100 µm.

In yet another embodiment, there is provided crystalline compound of formula (II) having an average particle size ($D_{50}$) less than 50 µm.

In yet another embodiment, there is provided crystalline compound of formula (II) having an average particle size ($D_{50}$) less than 20 µm.

In yet another embodiment, there is provided crystalline compound of formula (II) having an average particle size ($D_{50}$) less than 10 μm.

In another embodiment, the crystalline compound of formula (II) has about 10% of the particles ($D_{10}$) having size less than 10 μm, or preferably less than 5 μm.

In yet another embodiment, the crystalline compound of formula (II) has about 10% of the particles ($D_{10}$) having size less than 10 μm.

In yet another embodiment, the crystalline compound of formula (II) has about 10% of the particles ($D_{10}$) having size less than 5 μm.

In another embodiment, the crystalline compound of formula (II) has about 90% of the particles ($D_{90}$) having less than 200 μm, or preferably less than 100 μm, or more preferably less than 50 μm.

In yet another embodiment, the crystalline compound of formula (II) has about 90% of the particles ($D_{90}$) having less than 200 μm.

In yet another embodiment, the crystalline compound of formula (II) has about 90% of the particles ($D_{90}$) having less than 100 μm.

In yet another embodiment, the crystalline compound of formula (II) has about 90% of the particles ($D_{90}$) having less than 50 μm.

In yet another embodiment, the crystalline compound of formula (II) has about 90% of the particles ($D_{90}$) having less than 20 μm.

In yet another embodiment, there is provided crystalline compound of formula (II) having surface area of less than about 50 m²/μm, preferably less than 25 m²/μm or more preferably less than 10 m²/μm.

In yet another embodiment, there is provided crystalline compound of formula (II) having surface area of less than about 50 m²/μm.

In yet another embodiment, there is provided crystalline compound of formula (II) having surface area of less than about 25 m²/μm.

In yet another embodiment, there is provided crystalline compound of formula (II) having surface area of less than about 10 m²/μm.

The present invention also relates to the process for the preparation of thienopyrimidinedione compound of formula (II).

BRIEF DESCRIPTION OF THE FIGURES

FIG. 1 is powder X-ray diffraction pattern of crystalline potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as Form I.

FIG. 2 is Infra-Red (IR) spectra of crystalline potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as Form I.

FIG. 3 is powder X-ray diffraction pattern of crystalline potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as Form II.

FIG. 4 is Infra-Red (IR) spectra of crystalline potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as Form II.

FIG. 5 is powder X-ray diffraction pattern of amorphous potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide.

FIG. 6 is powder X-ray diffraction pattern of crystalline sodium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as Form A.

FIG. 7 is Infra-Red (IR) spectra of crystalline sodium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as Form A.

FIG. 8 is powder X-ray diffraction pattern of amorphous sodium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide.

FIG. 9 is Infra-Red (IR) spectra of amorphous sodium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide.

FIG. 10 is powder X-ray diffraction pattern of crystalline lithium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as Form Alpha.

FIG. 11 is Infra-Red (IR) spectra of crystalline lithium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as Form Alpha.

FIG. 12 is powder X-ray diffraction pattern of crystalline N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as Form X.

FIG. 13 is Infra-Red (IR) spectra of crystalline N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as Form X.

FIG. 14 is powder X-ray diffraction pattern of crystalline of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as Form Y.

FIG. 15 is Infra-Red (IR) spectra of crystalline N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as Form Y.

FIG. 16 is powder X-ray diffraction pattern of crystalline N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as Form Z.

FIG. 17 is Infra-Red (IR) spectra of crystalline N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as Form Z.

DETAILED DESCRIPTION OF THE INVENTION

The present application relates to salts of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as compound of formula (II)

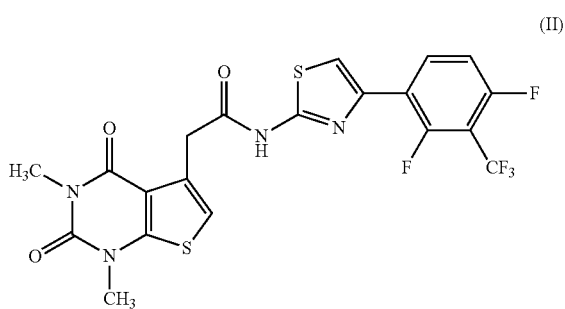 [SMILES: Cn1c(=O)c2c(CC(=O)Nc3nc(-c4ccc(F)c(C(F)(F)F)c4F)cs3)csc2n(C)c1=O]

and process for preparation thereof.

In an embodiment, the present invention relates to potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide.

In another embodiment, the present invention relates to Potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide in crystalline form.

In yet another embodiment, potassium salt of a compound of formula (II) is provided in an amorphous form.

In yet another embodiment, the solid state forms of potassium salt of a compound of formula (II) exist in an anhydrous and/or solvent-free form or as a hydrate and/or a solvate form.

In another embodiment, there is provided a method for treating diseases, conditions and/or disorders modulated by TRPA1; comprising administering a solid state form of potassium salt of compound of formula (II), or a pharmaceutical composition that comprises the solid state form of potassium salt of compound of formula (II) along with pharmaceutically acceptable excipients.

In yet another embodiment, there is provided a method for treating diseases, conditions and/or disorders modulated by TRPA1; comprising administering crystalline potassium salt of compound of formula (II), or a pharmaceutical composition that comprises crystalline potassium salt of compound of formula (II) along with pharmaceutically acceptable excipients.

In an embodiment, there is provided potassium salt of a compound of formula (II) having water content less than about 5%.

In another embodiment, there is provided crystalline potassium salt of a compound of formula (II) having water content less than about 5%.

In another embodiment, there is provided potassium salt of compound of formula (II) having water content about 0.2-2.0% as determined by Karl Fischer method, more preferably in the range 0.2 to 1.0%.

In another embodiment, there is provided potassium salt of compound of formula (II) having water content about 0.2-2.0% as determined by Karl Fischer method.

In another embodiment, there is provided potassium salt of compound of formula (II) having water content in the range of 0.2 to 1.0% as determined by Karl Fischer method.

In another embodiment, there is provided crystalline potassium salt of compound of formula (II) having water content about 0.2-2.0% as determined by Karl Fischer method.

In another embodiment, there is provided crystalline potassium salt of compound of formula (II) having water content in the range of 0.2 to 1.0% as determined by Karl Fischer method.

In another embodiment, there is provided the potassium salt of compound of formula (II) which exhibits the gradual increase of moisture content from initial value of about 0.80% to about 16.0% in 48 hours at 25° C./90% Relative Humidity (RH).

In another embodiment, there is provided crystalline potassium salt of compound of formula (II) which exhibits the gradual increase of moisture content from initial value of about 0.80% to about 16.0% in 48 hours at 25° C./90% Relative Humidity (RH).

In another embodiment, there is provided the potassium salt of compound of formula (II) which exhibits the gradual increase of moisture content from initial value of about 0.80% to about 6.6% in 48 hours at 25° C./80% RH.

In another embodiment, there is provided crystalline potassium salt of compound of formula (II) which exhibits the gradual increase of moisture content from initial value of about 0.80% to about 6.6% in 48 hours at 25° C./80% RH.

In another embodiment, there is provided the potassium salt of compound of formula (II) which exhibits the gradual increase of moisture content from initial value of about 0.80% to about 3.5% in 48 hours at 25° C./60% RH.

In another embodiment, there is provided the crystalline potassium salt of compound of formula (II) which exhibits the gradual increase of moisture content from initial value of about 0.80% to about 3.5% in 48 hours at 25° C./60% RH.

In another embodiment, there is provided the potassium salt of compound of formula (II) which exhibits a moisture content increase of about 15.2% or less when stored under a relative humidity of 90% at a temperature of 25° C. for 48 hrs.

In another embodiment, there is provided the potassium salt of compound of formula (II) which exhibits a moisture content increase of about 5.8% or less when stored under a relative humidity of 80% at a temperature of 25° C. for 48 hrs.

In another embodiment, there is provided the potassium salt of compound of formula (II) which exhibits a moisture content increase of about 2.7% or less when stored under a relative humidity of 60% at a temperature of 25° C. for 48 hrs.

In another embodiment, there is provided the potassium salt of compound of formula (II) which exhibits the gradual increase of moisture content from initial value of 0.80% to 16.0% in 48 hrs at 25° C./90% Relative Humidity (RH).

In another embodiment, there is provided the potassium salt of compound of formula (II) which exhibits the gradual increase of moisture content from initial value of 0.80% to 6.6% in 48 hrs at 25° C./80% RH.

In another embodiment, there is provided the potassium salt of compound of formula (II) which exhibits the gradual increase of moisture content from initial value of 0.80% to 3.5% in 48 hrs at 25° C./60% RH.

In another embodiment, there is provided the potassium salt of compound of formula (II) has an average particle size ($D_{50}$) in the range from about 1 μm to about 100 μm, or about 1 μm to about 50 μm or from about 1 μm to about 20 μm.

In another embodiment, there is provided the potassium salt of compound of formula (II) has an average particle size ($D_{50}$) in the range from about 1 μm to about 100 μm.

In yet another embodiment, there is provided the potassium salt of compound of formula (II) has an average particle size ($D_{50}$) in the range from about 1 μm to about 50 μm.

In yet another embodiment, there is provided potassium salt of compound of formula (II) has an average particle size ($D_{50}$) in the range from about 1 μm to about 20 μm.

In another embodiment, there is provided crystalline potassium salt of compound of formula (II) has an average particle size ($D_{50}$) in the range from about 1 μm to about 100 μm.

In yet another embodiment, there is provided the crystalline potassium salt of compound of formula (II) has an average particle size ($D_{50}$) in the range from about 1 μm to about 50 μm.

In yet another embodiment, there is provided the crystalline potassium salt of compound of formula (II) has an average particle size ($D_{50}$) in the range from about 1 μm to about 20 μm.

In another embodiment, there is provided the potassium salt of compound of formula (II) has about 10% of the particles ($D_{10}$) having size in the range from about 0.3 μm to about 10 μm, or from about 0.5 μm to about 8 μm, preferably from about 0.5 μm to about 5 μm.

In another embodiment, there is provided the potassium salt of compound of formula (II) has about 10% of the particles ($D_{10}$) having size in the range from about 0.3 μm to about 10 μm.

In yet another embodiment, there is provided the potassium salt of compound of formula (II) has about 10% of the particles ($D_{10}$) having size in the range from about 0.5 μm to about 8 μm.

In yet another embodiment, there is provided the potassium salt of compound of formula (II) has about 10% of the particles ($D_{10}$) having size in the range from about 0.5 μm to about 5 μm.

In another embodiment, there is provided the crystalline potassium salt of compound of formula (II) has about 10% of the particles ($D_{10}$) having size in the range from about 0.3 μm to about 10 μm.

In yet another embodiment, there is provided the crystalline potassium salt of compound of formula (II) has about 10% of the particles ($D_{10}$) having size in the range from about 0.5 μm to about 8 μm.

In yet another embodiment, there is provided the crystalline potassium salt of compound of formula (II) has about 10% of the particles ($D_{10}$) having size in the range from about 0.5 μm to about 5 μm.

In another embodiment, the potassium salt of compound of formula (II) has about 90% of the particles ($D_{90}$) having size in the range from about 4 μm to about 300 μm or from about 5 μm to about 250 μm, preferably from about 5 μm to about 200 μm, and more preferably from 5 μm to about 150 μm.

In another embodiment, there is provided the potassium salt of compound of formula (II) has about 90% of the particles ($D_{90}$) having size in the range from about 4 μm to about 300 μm.

In yet another embodiment, there is provided the potassium salt of compound of formula (II) has about 90% of the particles ($D_{90}$) having size in the range from about 5 μm to about 250 μm.

In yet another embodiment, there is provided the potassium salt of compound of formula (II) has about 90% of the particles ($D_{90}$) having size in the range from about 5 μm to about 200 μm.

In yet another embodiment, there is provided the potassium salt of compound of formula (II) has about 90% of the particles ($D_{90}$) having size in the range from about 5 μm to about 150 μm.

In another embodiment, there is provided the crystalline potassium salt of compound of formula (II) has about 90% of the particles ($D_{90}$) having size in the range from about 4 μm to about 300 μm.

In yet another embodiment, there is provided the crystalline potassium salt of compound of formula (II) has about 90% of the particles ($D_{90}$) having size in the range from about 5 μm to about 250 μm.

In yet another embodiment, there is provided the crystalline potassium salt of compound of formula (II) has about 90% of the particles ($D_{90}$) having size in the range from about 5 μm to about 200 μm.

In yet another embodiment, there is provided the crystalline potassium salt of compound of formula (II) has about 90% of the particles ($D_{90}$) having size in the range from about 5 μm to about 150 μm.

The particle size characteristics for potassium salt of compound of formula (II) for some of the batches is provided in Table 1.

TABLE 1

| Batch. | Particle size | | |
|---|---|---|---|
| No | d (0.1) μm | d (0.5) μm | d (0.9) μm |
| 1 | 0.73 | 4.06 | 26.91 |
| 2 | 0.99 | 5.42 | 36.35 |
| 3 | 1.23 | 6.28 | 28.8 |
| 4 | 0.74 | 2.97 | 26.66 |
| 5 | 0.60 | 1.75 | 6.84 |
| 6 | 0.85 | 3.43 | 15.47 |
| 7 | 1.56 | 18.01 | 145.5 |
| 8 | 0.86 | 6.4 | 27.64 |
| 9 | 1.5 | 17.83 | 95.17 |
| 10 | 1.0 | 4.75 | 30.31 |
| 11 | 1.32 | 9.58 | 51.19 |
| 12 | 0.70 | 3.11 | 16.63 |
| 13 | 0.61 | 2.46 | 13.02 |
| 14 | 0.81 | 2.38 | 17.80 |
| 15 | 0.96 | 4.41 | 67.03 |
| 16 | 1.32 | 6.81 | 60.19 |
| 17 | 1.09 | 7.18 | 65.34 |
| 18 | 0.96 | 8.06 | 71.45 |
| 19 | 1.47 | 9.38 | 51.16 |
| 20 | 1.03 | 5.17 | 28.82 |
| 21 | 0.8 | 2.46 | 22.56 |
| 22 | 1.19 | 3.97 | 46.05 |
| 23 | 0.68 | 2.02 | 13.3 |

In another embodiment, the present invention also relates to substantially pure potassium salt of compound of formula (II). For the purposes of this invention, substantially pure is greater than about 90% pure.

In yet another embodiment, the present invention relates to substantially pure potassium salt of compound of formula (II) having purity greater than about 95%.

In yet another embodiment, the present invention relates to substantially pure potassium salt of compound of formula (II) having purity greater than about 98%.

In yet another embodiment, the present invention relates to substantially pure potassium salt of compound of formula (II) having purity greater than about 99%.

In yet another embodiment, the present invention also relates to substantially pure crystalline potassium salt of compound of formula (II). For the purposes of this invention, substantially pure is greater than about 90% pure.

In yet another embodiment, the present invention relates to substantially pure crystalline potassium salt of compound of formula (II) having purity greater than about 95%.

In yet another embodiment, the present invention relates to substantially pure crystalline potassium salt of compound of formula (II) having purity greater than about 98%.

In yet another embodiment, the present invention relates to substantially pure crystalline potassium salt of compound of formula (II) having purity greater than about 99%.

In another embodiment, the present invention relates to crystalline potassium salt of compound of formula (II) and process for the preparation thereof.

In yet another embodiment, the present invention relates to crystalline potassium salt of compound of formula (II).

In yet another embodiment, the present invention relates to crystalline form of potassium salt of compound of formula (II) which is designated as Form I.

In yet another embodiment, Form I is characterized by the X-Ray Powder Diffraction (XRPD) pattern as shown in FIG. 1.

In yet another embodiment, Form I is further characterized by the characteristic X-ray diffraction pattern comprising one or more of the following peaks expressed in terms of 2θ: 15.93, 20.61, 23.63, 24.47 and 25.08±0.2.

In yet another embodiment, Form I is further characterized by the characteristic X-ray diffraction pattern comprising of the following peak expressed in terms of 2θ: 23.63±0.2.

In yet another embodiment, Form I is further characterized by the characteristic X-ray diffraction pattern comprising of the following peak expressed in terms of 2θ: 24.47±0.2.

In yet another embodiment, Form I is further characterized by the characteristic X-ray diffraction pattern comprising one or more of the following peaks expressed in terms of 2θ: 23.63 and 24.47±0.2.

In yet another embodiment, Form I is further characterized by the characteristic X-ray diffraction pattern peaks expressed in terms of 2θ as presented in Table 2.

TABLE 2

Prominent two theta positions and relative intensities of XRPD of Form I

| Angle (2θ ± 0.2) | Relative intensity (%) |
|---|---|
| 5.71 | 13.97 |
| 11.77 | 14.06 |
| 13.44 | 55.35 |
| 15.35 | 17.71 |
| 15.93 | 53.98 |
| 16.97 | 41.34 |
| 18.15 | 24.74 |
| 18.68 | 11.12 |
| 20.61 | 41.50 |
| 23.12 | 17.53 |
| 23.63 | 100.00 |
| 24.47 | 70.32 |
| 25.08 | 28.91 |
| 25.90 | 38.19 |
| 27.01 | 23.79 |
| 28.34 | 10.62 |

In yet another embodiment, Form I is characterized by the Fourier Transform Infrared Spectroscopy (FT-IR) pattern as shown in FIG. 2.

In another embodiment, the present invention relates to another crystalline form of potassium salt of compound of formula (II) which is designated as Form II.

In yet another embodiment, Form II is characterized by the X-Ray Powder Diffraction (XRPD) pattern as shown in FIG. 3.

In yet another embodiment, Form II is further characterized by the characteristic X-ray diffraction pattern comprising one or more of the following peaks expressed in terms of 2θ: 12.07, 12.39, 20.98, 24.01 and 25.69±0.2.

In yet another embodiment, Form II is further characterized by the characteristic X-ray diffraction pattern comprising one or more of the following peaks expressed in terms of 2θ: 24.01 and 25.69±0.2.

In yet another embodiment, Form II is further characterized by the characteristic X-ray diffraction pattern comprising of the following peak expressed in terms of 2θ: 24.01±0.2.

In yet another embodiment, Form II is further characterized by the characteristic X-ray diffraction pattern comprising of the following peak expressed in terms of 2θ: 25.69±0.2.

In yet another embodiment, Form II is further characterized by the characteristic X-ray diffraction pattern peaks expressed in terms of 2θ as presented in Table 3.

TABLE 3

Prominent two theta positions and relative intensities of XRPD of Form II

| Angle (2θ ± 0.2) | Relative intensity (%) |
|---|---|
| 5.77 | 3.22 |
| 10.21 | 4.98 |
| 11.34 | 4.63 |
| 12.07 | 15.68 |
| 12.39 | 19.99 |
| 13.40 | 42.66 |
| 13.95 | 8.63 |
| 16.17 | 49.47 |
| 16.95 | 20.39 |
| 17.96 | 10.03 |
| 18.89 | 10.67 |
| 20.98 | 45.47 |
| 21.60 | 8.33 |
| 23.05 | 11.76 |
| 24.01 | 73.52 |
| 24.68 | 68.88 |
| 25.69 | 100 |
| 26.17 | 15.22 |
| 26.66 | 6.64 |
| 27.88 | 16.62 |
| 28.78 | 17.67 |
| 29.18 | 27.47 |
| 30.50 | 8.88 |
| 32.95 | 10.18 |
| 33.57 | 10.97 |
| 34.70 | 4.11 |
| 36.24 | 5.65 |
| 37.30 | 9.54 |
| 38.13 | 16.24 |
| 40.05 | 9.91 |
| 40.93 | 8.12 |
| 42.74 | 10.60 |
| 43.67 | 7.84 |
| 44.95 | 5.27 |
| 49.11 | 4.82 |

In yet another embodiment, Form II is characterized by the IR pattern as shown in FIG. 4.

In another embodiment, the present invention relates to amorphous potassium salt of compound of formula (II).

In yet another embodiment, the amorphous form of potassium salt of compound of formula (II) is characterized by the X-ray powder diffraction pattern as shown in FIG. 5.

In an embodiment, the present invention relates to crystalline sodium salt of compound of formula (II).

In another embodiment, the present invention relates to crystalline sodium salt of compound of formula (II) which is designated as Form A.

In yet another embodiment, the Form A is characterized by the X-ray powder diffraction pattern as shown in FIG. 6.

In yet another embodiment, Form A is further characterized by the characteristic X-ray powder diffraction pattern peaks expressed in terms of 2θ as presented in Table 4.

TABLE 4

Prominent two theta positions and relative intensities of XRPD of Form A

| Angle (2θ ± 0.2) | Relative intensity (%) |
|---|---|
| 5.57 | 10.73 |
| 9.43 | 31.30 |
| 14.21 | 100.00 |
| 16.06 | 66.36 |
| 18.02 | 15.75 |
| 19.18 | 15.56 |
| 20.61 | 44.62 |
| 24.19 | 79.32 |
| 25.70 | 28.52 |
| 26.43 | 85.40 |
| 27.20 | 66.24 |
| 30.31 | 22.49 |
| 31.61 | 19.27 |
| 32.37 | 31.05 |
| 39.36 | 25.50 |

In yet another embodiment, Form A is characterized by the IR pattern as shown in FIG. 7.

In another embodiment, the present invention relates to amorphous sodium salt of compound of formula (II).

In yet another embodiment, the amorphous form of sodium salt of compound of formula (II) characterized by the X-ray powder diffraction pattern as shown in FIG. 8.

In yet another embodiment, the amorphous form of sodium salt of compound of formula (II) is characterized by the IR pattern shown in FIG. 9.

In another embodiment, the present invention relates to lithium salt of compound of formula (II).

In yet another embodiment, the present invention relates to crystalline lithium salt of compound of formula (II).

In yet another embodiment, the present invention relates to crystalline lithium salt of compound of formula (II) which may be designated as Form alpha.

In yet another embodiment, the Form alpha is characterized by the X-ray powder diffraction pattern as shown in FIG. 10.

In yet another embodiment, the Form alpha is characterized by the IR pattern shown in FIG. 11

In yet another embodiment, the Form alpha is further characterized by the characteristic X-ray diffraction pattern peaks expressed in terms of 2θ as presented in Table 5.

TABLE 5

Prominent two theta positions and relative intensities of XRPD of Form Alpha

| Angle (2θ ± 0.2) | Relative intensity (%) |
|---|---|
| 7.58 | 36.20 |
| 11.83 | 100.00 |
| 13.31 | 16.31 |
| 15.07 | 20.05 |
| 15.27 | 15.45 |
| 17.90 | 8.22 |
| 20.35 | 9.88 |
| 20.76 | 9.10 |
| 22.97 | 26.90 |
| 23.92 | 28.65 |
| 24.71 | 21.25 |
| 25.57 | 19.43 |
| 26.20 | 8.25 |
| 26.86 | 8.31 |

In an embodiment, the present invention relates to process for the preparation of potassium salt of compound of formula (II), which comprises the following steps:

(a) providing a solution or suspension of compound of formula (II) in a suitable solvent or mixture of solvents;

(b) adding a source of potassium cation to the solution or suspension of step (a) or adding the solution or suspension of step (a) to the source of potassium cation; and (c) isolating the desired salt.

Step (a) involves providing a solution or suspension of compound of formula (II) in a suitable solvent or mixture of solvents. The solution or suspension of compound of formula (II) may be obtained by dissolving or suspending compound of formula (II) in a solvent or mixture of solvents, or may be obtained in situ, directly from the reaction in which compound of formula (II) is formed. The suitable solvent can be any solvent which has no adverse effect on the reaction or on the reagents involved and that it can dissolve the compound of formula (II), at least to some extent. The solvent system is preferably selected so as to facilitate the salt formation. Solvent(s) which may be used for dissolving or suspending compound of formula (II) include, but are not limited to, nitriles such as acetonitrile and propionitrile; alcohols, such as methanol, ethanol, isopropyl alcohol, n-propanol and tertiary butanol; ketones, such as acetone, ethyl methyl ketone, and methyl isobutyl ketone; esters such as ethyl acetate, n-propyl acetate, n-butyl acetate, and t-butyl acetate; ethers, such as diethyl ether, dimethyl ether, diisopropyl ether, and 1,4-dioxane; halogenated hydrocarbons, such as dichloromethane, dichloroethane, and chloroform; hydrocarbons such as n-hexane, heptane, n-pentane, cyclopentane, and cyclohexane; or any mixtures thereof. The preferred solvent may include ethanol or n-pentane or combination thereof.

In step (b), the solution or suspension compound of formula (II) is treated with a source of potassium cation. The source of potassium cation can be potassium alkoxide such as potassium tertiary butoxide or potassium ethoxide.

In an embodiment, compound of formula (II) can be treated with potassium tertiary butoxide taken in a suitable solvent such as alcohol. In an embodiment, the reaction can be carried out at a temperature ranging from about −5° C. to about boiling point of the solvent(s). In one embodiment, the reaction can be carried out at about −5° C. to 0° C. The time required for the completion of the reaction may also vary widely, depending on many factors, notably the reaction temperature and the nature of the reagents and solvent employed. However, provided that the reaction is effected under the conditions outlined above; a period of from about 1 hour to about 24 hours or longer is sufficient.

Step (c) involves isolation of desired salt. The potassium salt of compound of formula (II) produced in the reaction can be isolated using techniques including precipitation and/or decantation, filtration by gravity or suction, centrifugation, or evaporation of solvent or the like, and optionally washing the resulting solid with a solvent. In another embodiment, the washing is with the solvent used in the above reaction. Alternatively, the obtained solid may be optionally washed with a suitable solvent such as acetonitrile or diethyl ether. The recovered solid may be optionally further dried. Drying may be carried out in a tray dryer, vacuum oven, air oven, fluidized bed drier, spin flash dryer, flash dryer, or the like. The drying may be carried out at atmospheric pressure or under a reduced pressure at suitable temperatures as long as the product is not degraded in quality. The drying may be carried out for any desired time until the required purity is achieved. For example, it may vary from about 1 to about 10 hours or longer.

In another aspect, the present invention relates to process for the preparation of crystalline potassium salt of compound of formula (II) which is designated as Form I.

The process comprises taking the compound of formula (II) in a mixture of ethanol and n-pentane, preferably under inert atmosphere. The reaction mass may be cooled to about −5 to 0° C. and stirred for about 10 minutes. To the reaction mass, ethanolic solution of potassium tertiary butoxide or potassium ethoxide may be added. The reaction mass may be stirred further at about −5 to 0° C. for about an hour. To the reaction mixture, n-pentane may be added and the reaction mixture may be further stirred at room temperature for suitable period of time such as for 1-2 h. The solid may be collected by methods including decantation, centrifugation, gravity filtration, suction filtration, or any other technique for the recovery of solids. The obtained solid may be further taken in acetonitrile and the whole mass may be stirred at room temperature for suitable period of time such as for 1-2 h. The solid may be collected by methods including decantation, centrifugation, gravity filtration, suction filtration, or any other technique for the recovery of solids. In a preferred embodiment, the solid may be filtered and washed with acetonitrile.

The recovered solid may be optionally further dried. Drying may be carried out in a tray dryer, vacuum oven, air oven, fluidized bed drier, spin flash dryer, flash dryer, or the like. The drying may be carried out at atmospheric pressure or under a reduced pressure at suitable temperatures as long as the potassium salt of compound of formula (II) is not degraded in quality. The drying may be carried out for any desired time until the required purity is achieved. For example, it may vary from about 1 to about 10 hours or longer.

In another embodiment, the present invention relates to another process for the preparation of crystalline potassium salt of compound of formula (II) designated as Form I which process involves taking amorphous form of potassium salt of compound of formula (II) in acetonitrile; stirring the reaction mass for suitable period of time and isolating crystalline Form I. In this embodiment, the mixture of amorphous form of potassium salt of compound of formula (II) and acetonitrile may be stirred for a period such as 1-2 hours at a suitable temperature such as 25-35° C. The solid may be collected by known techniques such as filtration. The obtained solid may be further dried for a suitable period of time at a suitable temperature optionally under reduced pressure. For example the solid may be dried for 3-4 hours at 30-35° C. under vacuum.

In a further embodiment, the present invention relates to process for the preparation of crystalline form of potassium salt of compound of formula (II) designated as Form II which process comprises taking the compound of formula (II) in a mixture of tertiary butanol and n-pentane, preferably under inert atmosphere. The reaction mass may be cooled to about −5 to 0° C. and stirred for about 10 minutes. To the reaction mass, potassium tertiary butoxide in tertiary butanol may be added. The reaction mass may be stirred further at about −5 to 0° C. for about an hour. The solid may be collected by methods including decantation, centrifugation, gravity filtration, suction filtration, or any other technique for the recovery of solids. The solid may be further washed with n-pentane. The obtained solid may be further taken in acetonitrile and the whole mass may be stirred at room temperature for suitable period of time such as for 1-2 h. The solid may be collected by methods including decantation, centrifugation, gravity filtration, suction filtration, or any other technique for the recovery of solids. In a preferred embodiment, the solid may be filtered and washed with acetonitrile.

The recovered solid may be optionally further dried. Drying may be carried out in a tray dryer, vacuum oven, air oven, fluidized bed drier, spin flash dryer, flash dryer, or the like. The drying may be carried out at atmospheric pressure or under a reduced pressure at suitable temperatures as long as the potassium salt of compound of formula (II) is not degraded in quality. The drying may be carried out for any desired time until the required purity is achieved. For example, it may vary from about 1 to about 10 hours or longer.

In an embodiment, the present application also provides a process for the preparation of an amorphous form of potassium salt of compound of formula (II) which comprises heating the potassium salt of compound of formula (II) on heating mental at 300-320° C. The heating may be carried out at a reduced pressure.

In an aspect, the present invention relates to process for the preparation of sodium salt of compound of formula (II), which comprises the following steps:

(a) providing a solution or suspension of compound of formula (II) in a suitable solvent or mixture of solvents;

(b) adding a source of sodium cation to the solution or suspension of step (a) or adding the solution or suspension of step (a) to the source of sodium cation; and (c) isolating the desired salt.

Step (a) involves providing a solution or suspension of compound of formula (II) in a suitable solvent or mixture of solvents. The solution or suspension of compound of formula (II) may be obtained by dissolving or suspending compound of formula (II) in a solvent or mixture of solvents, or may be obtained in situ, directly from the reaction in which compound of formula (II) is formed. The suitable solvent can be any solvent which has no adverse effect on the reaction or on the reagents involved and that it can dissolve the compound of formula (II), at least to some extent. The solvent system is preferably selected so as to facilitate the salt formation. Solvent(s) which may be used for dissolving or suspending compound of formula (II) include, but are not limited to, nitriles such as acetonitrile and propionitrile; alcohols, such as methanol, ethanol, iso-propyl alcohol, and n-propanol; ketones, such as acetone, ethyl methyl ketone, and methyl isobutyl ketone; esters such as ethyl acetate, n-propyl acetate, n-butyl acetate, and t-butyl acetate; ethers, such as diethyl ether, dimethyl ether, diisopropyl ether, and 1,4-dioxane; halogenated hydrocarbons, such as dichloromethane, dichloroethane, and chloroform; hydrocarbons such as n-hexane, heptane, n-pentane, cyclopentane, and cyclohexane; or any mixtures thereof. The preferred solvent is ethanol.

In step (b), the solution or suspension compound of formula (II) is treated with a source of sodium cation. The source of sodium cation can be selected from sodium methoxide, sodium ethoxide and sodium tert-butoxide. In an embodiment, the reaction can be carried out at a temperature ranging from about −5° C. to about boiling point of the solvent(s). In one embodiment, the reaction can be carried out at about −5° C. to 0° C. The time required for the completion of the reaction may also vary widely, depending on many factors, notably the reaction temperature and the nature of the reagents and solvent employed. However, provided that the reaction is effected under the conditions outlined above; a period of from about 1 hour to about 24 hours or longer is sufficient.

Step (c) involves isolation of desired salt. The sodium salt of compound of formula (II) produced in the reaction can be isolated using techniques such as decantation, filtration by gravity or suction, centrifugation, or evaporation of solvent or the like, and optionally washing the resulting solid with a solvent or mixture of solvents.

The recovered solid may be optionally further dried. Drying may be carried out in a tray dryer, vacuum oven, air oven, fluidized bed drier, spin flash dryer, flash dryer, or the like. The drying may be carried out at atmospheric pressure or under a reduced pressure at suitable temperatures as long as the product is not degraded in quality. The drying may be carried out for any desired time until the required purity is achieved. For example, it may vary from about 1 to about 10 hours or longer.

In another aspect, the present invention relates to process for the preparation of crystalline sodium salt of compound of formula (II) designated as Form A.

In a preferred embodiment, the compound of formula (II) may be taken in ethanol, preferably in absolute ethanol, preferably under inert atmosphere. The reaction mass may be cooled to temperature of −5 to 0° C. To the reaction mass, ethanolic solution of sodium methoxide may be added. Preferably, the addition may be carried out at the temperature of −5 to 0° C. and the reaction mass may be maintained at that temperature for about an hour. The solid may be collected by various techniques. The isolation of solid may be effected by methods including removal of solvent, concentrating the reaction mass, or any other suitable techniques. Suitable techniques that may be used for the removal of solvent include and are not limited to rotational distillation using a device, such as, for example, a Buchi® Rotavapor®. In one embodiment, the solvent may be removed under reduced pressure.

The recovered solid may be optionally further dried. The dried solid may be further stirred with acetonitrile for a period of 1 to 2 hours. The solid may be collected by known techniques such as filtration, centrifugation, or decantation.

The recovered solid may be optionally further dried. Drying may be carried out in a tray dryer, vacuum oven, air oven, fluidized bed drier, spin flash dryer, flash dryer, or the like. The drying may be carried out at atmospheric pressure or under a reduced pressure at suitable temperatures as long as the sodium salt of compound of formula (II) is not degraded in quality. The drying may be carried out for any desired time until the required purity is achieved. For example, it may vary from about 1 to about 10 hours or longer.

In another embodiment, the present invention relates to another process for the preparation of crystalline sodium salt of compound of formula (II) designated as Form A which process involves taking amorphous form of sodium salt of compound of formula (II) in acetonitrile; stirring the reaction mass for suitable period of time and isolating crystalline Form A. In this embodiment, the mixture of amorphous form of sodium salt of compound of formula (II) and acetonitrile may be stirred for a period such as 1-2 hours at a suitable temperature such as 25-35° C. The solid may be collected by known techniques such as filtration. The obtained solid may be further dried for a suitable period of time at a suitable temperature optionally under reduced pressure. For example the solid may be dried for 3-4 hours at 30-35° C. under vacuum.

In an embodiment, the present application provides a process for the preparation of an amorphous form of sodium salt of compound of formula (II), comprising:

(a) providing solution or suspension of sodium salt of compound of formula (II) in a solvent or mixture of solvents; and (b) isolating an amorphous form of sodium salt of compound of formula (II).

In a preferred embodiment, the compound of formula (II) may be taken in an alcohol for example in ethanol and ethanolic solution of sodium tertiary butoxide may be added at an appropriate temperature. For example the addition may be carried out at a temperature range of −5 to 0° C. The reaction mixture may be stirred at −5 to 0° C. for about 1 hr.

Step b) involves isolation of an amorphous form of sodium salt of compound of formula (II).

In preferred embodiment, the isolation step (b) may be carried out by removing solvent. Suitable techniques which may be used for the removal of solvent include using a rotational distillation device such as a Buchi® Rotavapor®, spray drying, agitated thin film drying, freeze drying (lyophilization), or any other suitable technique.

The solvent may be removed, optionally under reduced pressure, at temperatures less than about 60° C., less than about 40° C., less than about 20° C., or any other suitable temperatures.

The compound obtained from step (b) may be collected using techniques such as by scraping, or other techniques specific to the equipment used.

The product thus isolated may be optionally further dried to afford an amorphous form of sodium salt of compound of formula (II). Drying may be suitably carried out in a tray dryer, vacuum oven, Buchi® Rotavapor®, air oven, fluidized bed dryer, spin flash dryer, flash dryer, or the like. The drying may be carried out at atmospheric pressure or under reduced pressures at suitable temperatures. The drying may be carried out for any time period required for obtaining a desired quality, such as from about 15 minutes to several hours.

In an aspect, the present invention relates to process for the preparation of lithium salt of compound of formula (II) which comprises the following steps:

(a) providing a solution or suspension of compound of formula (II) in a suitable solvent or mixture of solvents;

(b) adding a source of lithium cation to the solution or suspension of step (a) or adding the solution or suspension of step (a) to the source of lithium cation; and (c) isolating the desired salt.

Step (a) involves providing a solution or suspension of compound of formula (II) in a suitable solvent or mixture of solvents. The solution or suspension of compound of formula (II) may be obtained by dissolving or suspending compound of formula (II) in a solvent or mixture of solvents, or may be obtained in situ, directly from the reaction in which compound of formula (II) is formed. The suitable solvent can be any solvent which has no adverse effect on the reaction or on the reagents involved and that it can dissolve the compound of formula (II), at least to some extent. The solvent system is preferably selected so as to facilitate the salt formation. Solvent(s) which may be used for dissolving or suspending compound of formula (II) include, but are not limited to, nitriles such as acetonitrile and propionitrile; alcohols, such as methanol, ethanol, isopropyl alcohol, and n-propanol; ketones, such as acetone, ethyl methyl ketone, and methyl isobutyl ketone; esters such as ethyl acetate, n-propyl acetate, n-butyl acetate, and t-butyl acetate; ethers, such as diethyl ether, dimethyl ether, diisopropyl ether, and 1,4-dioxane; halogenated hydrocarbons, such as dichloromethane, dichloroethane, and chloroform;

hydrocarbons such as n-hexane, heptane, n-pentane, cyclopentane, and cyclohexane; or any mixtures thereof. The preferred solvent is ethanol.

In step (b), the solution or suspension compound of formula (II) is treated with a source of lithium cation. The source of lithium cation can be lithium hydroxide or lithium hydroxide monohydrate. In an embodiment, compound of formula (II) is treated with lithium hydroxide monohydrate taken in a suitable solvent such as alcohol. In an embodiment, the reaction can be carried out at a temperature ranging from about −5° C. to about boiling point of the solvent(s). In one embodiment, the reaction can be carried out at about −5° C. to 0° C. The time required for the completion of the reaction may also vary widely, depending on many factors, notably the reaction temperature and the nature of the reagents and solvent employed. However, provided that the reaction is effected under the conditions outlined above; a period of from about 1 hour to about 24 hours or longer is sufficient. In step (b), generally a solution of lithium hydroxide monohydrate in ethanol may be added to the solution or suspension or compound of formula (II).

Step (c) involves isolation of desired salt. The lithium salt of compound of formula (II) produced in the reaction can be isolated using techniques such as decantation, filtration by gravity or suction, centrifugation, or evaporation of solvent or the like, and optionally washing the resulting solid with a solvent.

In preferred embodiment the reaction mixture of step (b) is subjected to evaporation under reduced pressure. The obtained solid may be further optionally taken in a suitable solvent such as acetonitrile or diethyl ether and stirred for a suitable period of time. The solid may be collected by filtration. The recovered solid may be further dried. Drying may be carried out in a tray dryer, vacuum oven, air oven, fluidized bed drier, spin flash dryer, flash dryer, or the like. The drying may be carried out at atmospheric pressure or under a reduced pressure at suitable temperatures as long as the product is not degraded in quality. The drying may be carried out for any desired time until the required purity is achieved. For example, it may vary from about 1 to about 10 hours or longer.

In another embodiment, the present invention relates to process for the preparation of crystalline lithium salt of compound of formula (II) which is designated as Form Alpha.

In a preferred embodiment, the compound of formula (II) may be taken in ethanol, for example in absolute ethanol preferably under inert atmosphere. The reaction mass may be cooled to a temperature of −5 to 0° C. To the reaction mass, lithium hydroxide monohydrate may be added. Preferably, the addition may be carried out at the temperature of −5 to 0° C. and the reaction mass may be maintained at that temperature for about an hour.

The solid may be collected by various techniques. The isolation of solid may be effected by methods including removal of solvent, concentrating the reaction mass, or any other suitable techniques. Suitable techniques that may be used for the removal of solvent include and are not limited to rotational distillation using a device, such as, for example, a Buchi® Rotavapor®. In preferred embodiment, removal of solvent may be effected by methods including removal of solvent under reduced pressure.

The recovered solid may be optionally further dried. The dried solid may be further stirred with a suitable solvent such as diethyl ether for a period of 1 to 2 hours. The solid may be collected by known techniques such as filtration, centrifugation, or decantation.

The recovered solid may be optionally further dried. Drying may be carried out in a tray dryer, vacuum oven, air oven, fluidized bed drier, spin flash dryer, flash dryer, or the like. The drying may be carried out at atmospheric pressure or under a reduced pressure at suitable temperatures as long as the lithium salt of compound of formula (II) is not degraded in quality. The drying may be carried out for any desired time until the required purity is achieved. For example, it may vary from about 1 to about 10 hours or longer.

In another embodiment, the present invention relates to process for the preparation of crystalline lithium salt of compound of formula (II) designated as Form alpha which process involves taking amorphous form of lithium salt of compound of formula (II) in diethyl ether or any other suitable solvent such as acetonitrile; stirring the reaction mass for suitable period of time and isolating crystalline Form alpha. In this embodiment, the mixture of amorphous form of lithium salt of compound of formula (II) and diethyl ether may be stirred for a period such as 1-2 hours. The solid may be collected by known techniques such as filtration. The obtained solid may be further dried for a suitable period of time at a suitable temperature optionally under reduced pressure. For example the solid may be dried for 3-4 hours at 30-35° C. under vacuum.

In another embodiment, the present invention relates to a pharmaceutical composition comprising an excipients, carriers, diluents or mixture thereof, and therapeutically acceptable amount of potassium salt of compound of formula (II).

The present application also relates to crystalline forms of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as compound of formula (II):

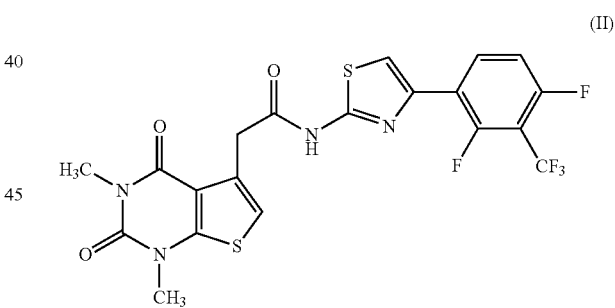

and process for preparation thereof.

In another embodiment, the crystalline forms of compound of formula (II) of the present invention exist in an anhydrous and/or solvent-free form or as a hydrate and/or a solvate form.

In another embodiment, there is provided crystalline compound of formula (II) having water content less than about 5%.

In another embodiment, there is provided crystalline compound of formula (II) having water content about 0.2-2.0% as determined by Karl Fischer method, more preferably in the range 0.2 to 1.0%.

In yet another embodiment, there is provided crystalline compound of formula (II) having surface area of less than about 50 m$^2$/gm, preferably less than 25 m$^2$/gm or more preferably less than 10 m$^2$/gm.

In yet another embodiment, there is provided crystalline compound of formula (II) having surface area of less than about 50 m²/gm.

In yet another embodiment, there is provided crystalline compound of formula (II) having surface area of less than about 25 m²/gm.

In yet another embodiment, there is provided crystalline compound of formula (II) having surface area of less than about 10 m²/gm.

In another embodiment, there is provided crystalline compound of formula (II) having an average particle size ($D_{50}$) less than 100 μm, or preferably less than 50 μm, or more preferably less than 20 μm.

In another embodiment, there is provided crystalline compound of formula (II) having an average particle size ($D_{50}$) less than 100 μm.

In yet another embodiment, there is provided crystalline compound of formula (II) having an average particle size ($D_{50}$) less than 50 μm.

In yet another embodiment, there is provided crystalline compound of formula (II) having an average particle size ($D_{50}$) less than 20 μm.

In yet another embodiment, there is provided crystalline compound of formula (II) having an average particle size ($D_{50}$) less than 10 μm.

In another embodiment, the crystalline compound of formula (II) has about 10% of the particles ($D_{10}$) having size less than 10 μm, or preferably less than 5 μm.

In yet another embodiment, the crystalline compound of formula (II) has about 10% of the particles ($D_{10}$) having size less than 10 μm.

In yet another embodiment, the crystalline compound of formula (II) has about 10% of the particles ($D_{10}$) having size less than 5 μm.

In another embodiment, the crystalline compound of formula (II) has about 90% of the particles ($D_{90}$) having less than 200 μm, or preferably less than 100 μm, or more preferably less than 50 μm.

In yet another embodiment, the crystalline compound of formula (II) has about 90% of the particles ($D_{90}$) having less than 200 μm.

In yet another embodiment, the crystalline compound of formula (II) has about 90% of the particles ($D_{90}$) having less than 100 μm.

In yet another embodiment, the crystalline compound of formula (II) has about 90% of the particles ($D_{90}$) having less than 50 μm.

In yet another embodiment, the crystalline compound of formula (II) has about 90% of the particles ($D_{90}$) having less than 20 μm.

In another embodiment, the present invention relates to crystalline form of compound of formula (II) which is designated as Form X.

In another embodiment, Form X is characterized by the X-Ray Powder Diffraction (XRPD) pattern as shown in FIG. 12.

In another embodiment, Form X is characterized by the IR pattern as shown in FIG. 13.

In another embodiment, Form X is further characterized by the characteristic X-ray diffraction pattern comprising one or more of the following peaks expressed in terms of 2θ: 11.06, 12.84 and 13.37±0.2.

In yet another embodiment, Form X is further characterized by the characteristic X-ray diffraction pattern comprising one or more of the following peaks expressed in terms of 2θ: 19.93 and 24.94±0.2.

In yet another embodiment, Form X is further characterized by the characteristic X-ray diffraction pattern comprising one or more of the following peaks expressed in terms of 2θ: 11.06, 12.84, 13.34, 19.93 and 24.94±0.2.

In another embodiment, Form X is further characterized by the characteristic X-ray diffraction pattern peaks expressed in terms of 2θ as presented in Table 6.

TABLE 6

Prominent two theta positions and relative intensities of XRPD of Form X

| Angle (2θ ± 0.2) | Relative intensity (%) |
|---|---|
| 9.45 | 32.13 |
| 11.06 | 9.43 |
| 12.84 | 9.31 |
| 13.37 | 10.30 |
| 14.13 | 100.00 |
| 16.24 | 27.30 |
| 16.33 | 33.96 |
| 18.24 | 18.75 |
| 18.81 | 6.72 |
| 19.93 | 4.86 |
| 21.14 | 5.72 |
| 21.84 | 5.21 |
| 22.58 | 13.09 |
| 23.60 | 9.22 |
| 24.13 | 14.08 |
| 24.58 | 15.39 |
| 24.94 | 9.18 |
| 25.66 | 8.65 |
| 27.14 | 29.38 |
| 27.55 | 14.01 |
| 31.85 | 8.52 |
| 43.25 | 17.52 |
| 46.45 | 6.32 |

In another embodiment, the present invention relates to another crystalline form of compound of formula (II) which is designated as Form Y.

In another embodiment, Form Y is characterized by the X-Ray Powder Diffraction (XRPD) pattern as shown in FIG. 14.

In another embodiment, Form Y is characterized by the Fourier Transform Infrared Spectroscopy (FT-IR) pattern as shown in FIG. 15.

In another embodiment, crystalline N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl) acetamide designated as Form Y characterised by the Fourier Transform Infrared Spectroscopy (FT-IR) pattern wherein the ratio between the intensity of the absorption bands at wavelengths 1500 cm$^{-1}$ and 1480 cm$^{-1}$ is from 1:1.7 to 1:2.4.

In another embodiment, Form Y is further characterized by the characteristic X-ray diffraction pattern comprising one or more of the following peaks expressed in terms of 2θ: 4.72 and 9.40±0.2.

In yet another embodiment, Form Y is further characterized by the characteristic X-ray diffraction pattern comprising one or more of the following peaks expressed in terms of 2θ: 21.04, 25.87 and 31.73±0.2.

In yet another embodiment, Form Y is further characterized by the characteristic X-ray diffraction pattern comprising one or more of the following peaks expressed in terms of 2θ: 4.72, 9.40, 21.04, 25.87 and 31.73±0.2.

In another embodiment, Form Y is further characterized by the characteristic X-ray diffraction pattern peaks expressed in terms of 2θ as presented in Table 7.

TABLE 7

Prominent two theta positions and relative intensities of XRPD of Form Y

| Angle (2θ ± 0.2) | Relative intensity (%) |
|---|---|
| 4.72 | 8.68 |
| 9.40 | 50.36 |
| 14.08 | 100.00 |
| 16.29 | 25.71 |
| 18.22 | 16.86 |
| 18.81 | 6.22 |
| 21.04 | 2.08 |
| 22.59 | 12.31 |
| 23.57 | 11.20 |
| 24.08 | 5.56 |
| 24.52 | 7.41 |
| 25.87 | 0.77 |
| 27.12 | 25.95 |
| 31.73 | 6.32 |
| 41.39 | 8.35 |
| 43.08 | 16.38 |
| 46.31 | 5.09 |

In another embodiment, the present invention relates to yet another crystalline form of compound of formula (II) which is designated as Form Z.

In another embodiment, Form Z is characterized by the X-Ray Powder Diffraction (XRPD) pattern as shown in FIG. 16.

In another embodiment, Form Z is characterized by the Fourier Transform Infrared (FT-IR) pattern as shown in FIG. 17.

In another embodiment, crystalline N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as Form Z characterised by the Fourier Transform Infrared (FT-IR) Spectroscopy pattern wherein the ratio between the intensity of the absorption bands at wavelengths 1500 cm$^{-1}$ and 1480 cm$^{-1}$ is from 1:2.5 to 1:2.9.

In another embodiment, Form Z is further characterized by the characteristic X-ray diffraction pattern comprising one or more of the following peaks expressed in terms of 2θ: 10.63 and 19.25±0.2.

In yet another embodiment, Form Z is further characterized by the characteristic X-ray diffraction pattern comprising one or more of the following peaks expressed in terms of 2θ: 22.11, 22.76 and 27.27±0.2.

In another embodiment, Form Z is further characterized by the characteristic X-ray diffraction pattern comprising one or more of the following peaks expressed in terms of 2θ: 10.63, 19.25, 22.11, 22.76 and 27.27±0.2.

In another embodiment, Form Z is further characterized by the characteristic X-ray powder diffraction pattern peaks expressed in terms of 2θ as presented in Table 8.

TABLE 8

Prominent two theta positions and relative intensities of XRPD of Form Z

| Angle (2θ ± 0.2) | Relative intensity (%) |
|---|---|
| 9.50 | 24.43 |
| 10.63 | 4.76 |
| 14.30 | 86.08 |
| 15.65 | 14.53 |
| 16.28 | 81.14 |
| 18.12 | 16.17 |
| 19.25 | 28.21 |
| 21.06 | 14.40 |
| 22.11 | 10.17 |
| 22.76 | 16.87 |
| 24.26 | 100.00 |
| 24.58 | 77.94 |
| 27.27 | 60.58 |
| 27.63 | 33.57 |
| 30.01 | 20.91 |
| 31.01 | 12.12 |
| 31.84 | 5.52 |
| 33.33 | 10.66 |
| 36.98 | 5.94 |
| 41.53 | 8.20 |
| 43.09 | 14.82 |
| 46.47 | 5.62 |

In another embodiment the crystalline forms of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide, forms X, Y and Z, can be independently or additionally distinguished by the ratio of the intensities of the absorption bands at wavelengths 1500 cm$^{-1}$ and 1480 cm$^{-1}$, being the highest for form X and lowest for Form Z as presented in Table 9.

TABLE 9

The ratio between the intensity of absorption bands at wavelength 1500 cm$^{-1}$ and 1480 cm$^{-1}$ depending on crystalline form of compound of formula (II)

| Form | The ratio between the intensity of absorption bands at 1500 cm$^{-1}$ and 1480 cm$^{-1}$ |
|---|---|
| Form X | from 1:3.0 to 1:4.0 |
| Form Y | from 1:1.7 to 1:2.4 |
| Form Z | from 1:2.5 to 1:2.9 |

In another embodiment, the present invention provides compound of formula (II) having purity greater than about 99.0%.

In another embodiment, the present invention provides compound of formula (II) having purity greater than about 99.5%.

In another embodiment, the present invention provides compound of formula (II) having less than about 0.1% (by HPLC) of the compound of formula (III):

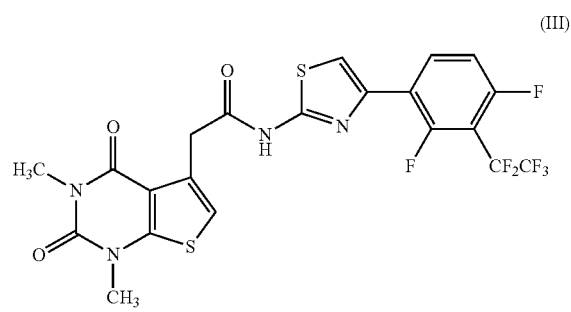

In another embodiment, the present invention provides crystalline compound of formula (II) having purity greater than about 99.8%.

In another embodiment, the present invention provides compound of formula (III)

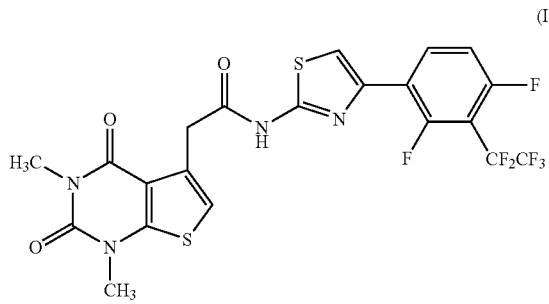

(III)

or a pharmaceutically acceptable salt thereof.

In another aspect, the present invention relates to process for the preparation of crystalline form of compound of formula (II) which is designated as Form X, which process involves the following steps:
I. taking the compound of formula (II) in an alcoholic solvent and stirring the mixture; and
II. isolating the solid.

In step I, the compound of formula (II) is taken in an alcohol, preferably methanol or isopropanol. In a preferred embodiment, the solvent is methanol. The mixture may be stirred at suitable temperature. In a preferred embodiment, the mixture may be stirred at 25-30° C. for suitable period of time. The suitable period may be in the range from 1 hour to 24 hours.

In step II, the desired form is isolated. The isolation of the solid may be effected by techniques known in the art, including but not limited to, decantation, filtration by gravity or suction, centrifugation, or evaporation of solvent or the like, and optionally washing the resulting solid with a solvent. The recovered solid may be optionally further dried. Drying may be carried out in a tray dryer, vacuum oven, air oven, fluidized bed drier, spin flash dryer, flash dryer, or the like. The drying may be carried out at atmospheric pressure or under a reduced pressure at suitable temperatures as long as the compound of formula (II) is not degraded in quality. The drying may be carried out for any desired time until the required purity is achieved. For example, it may vary from about 1 to about 10 hours or longer.

The compound of formula (II) of step I may be obtained by the coupling of (1,3-dimethyl-2,4-dioxo-1,2,3,4-tetrahydrothieno[2,3-d]pyrimidin-5-yl) acetic acid with 4-[2,4-difluoro-3-(trifluoromethyl)phenyl]-1,3-thiazol-2-amine using a suitable coupling agent, in the presence of a suitable base in a suitable solvent. The coupling agent used may be hydroxybenzotriazole (HOBt) or (1-(3-Dimethylaminopropyl)-3-ethylcarbodiimide) or mixtures thereof. The base used for the coupling may be 4-dimethylaminopyridine. The solvent used may be 1,2-dichloroethane.

In another aspect, the present invention relates to process for the preparation of crystalline form of compound of formula (II) which is designated as Form Y, which process involves the following steps:
(I) taking the compound of formula (II) in a halogenated solvent; and
(II) isolating the solid.

In step I, the halogenated solvent may be dichloromethane.

In step II, the desired form is isolated. The isolation of the solid may be effected by techniques known in the art, including but not limited to, decantation, filtration by gravity or suction, centrifugation, or evaporation of solvent or the like, and optionally washing the resulting solid with a solvent. The recovered solid may be optionally further dried. Drying may be carried out in a tray dryer, vacuum oven, air oven, fluidized bed drier, spin flash dryer, flash dryer, or the like. The drying may be carried out at atmospheric pressure or under a reduced pressure at suitable temperatures as long as the compound of formula (II) is not degraded in quality. The drying may be carried out for any desired time until the required purity is achieved. For example, it may vary from about 1 to about 10 hours or longer.

The compound of formula (II) of step I may be obtained by the coupling of (1,3-dimethyl-2,4-dioxo-1,2,3,4-tetrahydrothieno[2,3-d]pyrimidin-5-yl) acetic acid with 4-[2,4-difluoro-3-(trifluoromethyl)phenyl]-1,3-thiazol-2-amine using a suitable coupling agent, in the presence of a suitable base in a suitable solvent. The coupling agent used may be hydroxybenzotriazole (HOBt) or (1-(3-Dimethylaminopropyl)-3-ethylcarbodiimide) or mixtures thereof. The base used for the coupling may be N-methyl morpholine. The solvent used may be dichloromethane.

In another aspect, the present invention relates to process for the preparation of crystalline form of compound of formula (II) which is designated as Form Z, which process involves the following steps:
(I) taking the compound of formula (II) in polar solvent and stirring the mixture;
(II) adding water to the mixture and
(III) isolating the solid.

In step I, the compound of formula (II) is taken in polar solvent. In a preferred embodiment, the solvent is DMSO. The mixture may be stirred at suitable temperature. In a preferred embodiment, the mixture may be stirred at 50-60° C. for suitable period of time. The suitable period may be till a clear solution of the mixture was observed. Charcoal may be further added to the mixture and the mixture may be filtered prior to addition of water.

In step III, the desired form is isolated. The isolation of the solid may be effected by techniques known in the art, including but not limited to, decantation, filtration by gravity or suction, centrifugation, or evaporation of solvent or the like, and optionally washing the resulting solid with a solvent. The recovered solid may be optionally further dried. Drying may be carried out in a tray dryer, vacuum oven, air oven, fluidized bed drier, spin flash dryer, flash dryer, or the like. The drying may be carried out at atmospheric pressure or under a reduced pressure at suitable temperatures as long as the compound of formula (II) is not degraded in quality. The drying may be carried out for any desired time until the required purity is achieved. For example, it may vary from about 1 to about 10 hours or longer.

The crystalline form Z of compound of formula (II) may also be obtained from Form Y of the compound of formula (II).

In another embodiment, the present invention relates to a pharmaceutical composition comprising an excipients, carriers, diluents or mixture thereof, and therapeutically acceptable amount of crystalline compound of formula (II) designated as Form Y.

In another embodiment, the present invention pertains to a method of treating diseases or conditions or disorders associated with TRPA1 function in a subject in need thereof by administering to the subject an effective amount of potassium salt of compound of formula (II).

In another embodiment, there is provided a method for treating diseases, conditions and/or disorders modulated by TRPA1; comprising administering potassium salt of compound of formula (II) which exhibits the gradual increase of moisture content from initial value of about 0.80% to about 16.0% in 48 hrs at 25° C./90% RH, or a pharmaceutical composition that comprises the said potassium salt of compound of formula (II) along with pharmaceutically acceptable excipients.

In another embodiment, there is provided a method for treating diseases, conditions and/or disorders modulated by TRPA1; comprising administering potassium salt of compound of formula (II) which exhibits the gradual increase of moisture content from initial value of about 0.80% to about 6.6% in 48 hrs at 25° C./80% RH, or a pharmaceutical composition that comprises the said potassium salt of compound of formula (II) along with pharmaceutically acceptable excipients.

In another embodiment, there is provided a method for treating diseases, conditions and/or disorders modulated by TRPA1; comprising administering potassium salt of compound of formula (II) which exhibits the gradual increase of moisture content from initial value of about 0.80% to about 3.5% in 48 hrs at 25° C./60% RH, or a pharmaceutical composition that comprises the said potassium salt of compound of formula (II) along with pharmaceutically acceptable excipients.

In another embodiment, there is provided a method for treating diseases, conditions and/or disorders modulated by TRPA1; comprising administering a solid state form of potassium salt of compound of formula (II), or a pharmaceutical composition that comprises the solid state form of potassium salt of compound of formula (II) along with pharmaceutically acceptable excipients.

In another embodiment, there is provided a method for treating diseases, conditions and/or disorders modulated by TRPA1; comprising administering Form I or Form II or amorphous form of potassium salt of compound of formula (II), or a pharmaceutical composition that comprises the Form I or Form II or amorphous form of potassium salt of compound of formula (II) along with pharmaceutically acceptable excipients.

In another embodiment, the present invention pertains to a pharmaceutical composition comprising an excipients, carriers, diluents or mixture thereof, and therapeutically acceptable amount of sodium salt of compound of formula (II).

In another embodiment, the present invention pertains to a method of treating diseases or conditions or disorders associated with TRPA1 function in a subject in need thereof by administering to the subject an effective amount of sodium salt of compound of formula (II).

In another embodiment, there is provided a method for treating diseases, conditions and/or disorders modulated by TRPA1; comprising administering a solid state form of sodium salt of compound of formula (II), or a pharmaceutical composition that comprises the solid state form of sodium salt of compound of formula (II) along with pharmaceutically acceptable excipients.

In another embodiment, there is provided a method for treating diseases, conditions and/or disorders modulated by TRPA1; comprising administering a amorphous form of sodium salt of compound of formula (II), or a pharmaceutical composition that comprises the amorphous form of sodium salt of compound of formula (II) along with pharmaceutically acceptable excipients.

In another embodiment, there is provided a method for treating diseases, conditions and/or disorders modulated by TRPA1; comprising administering a crystalline form A of sodium salt of compound of formula (II), or a pharmaceutical composition that comprises the crystalline form A of sodium salt of compound of formula (II) along with pharmaceutically acceptable excipients.

In another embodiment, the present invention pertains to a pharmaceutical composition comprising an excipients, carriers, diluents or mixture thereof, and therapeutically acceptable amount of lithium salt of compound of formula (II).

In another embodiment, the present invention pertains to a method of treating diseases or conditions or disorders associated with TRPA1 function in a subject in need thereof by administering to the subject an effective amount of lithium salt of compound of formula (II).

In another embodiment, there is provided a method for treating diseases, conditions and/or disorders modulated by TRPA1; comprising administering a solid state form of lithium salt of compound of formula (II), or a pharmaceutical composition that comprises the solid state form of lithium salt of compound of formula (II) along with pharmaceutically acceptable excipients.

In another embodiment, there is provided a method for treating diseases, conditions and/or disorders modulated by TRPA1; comprising administering a crystalline form of lithium salt of compound of formula (II), or a pharmaceutical composition that comprises the crystalline form of lithium salt of compound of formula (II) along with pharmaceutically acceptable excipients.

In another embodiment, the present invention pertains to a method of treating diseases or conditions or disorders associated with TRPA1 which are selected from pain, chronic pain, complex regional pain syndrome, neuropathic pain, postoperative pain, rheumatoid arthritic pain, osteoarthritic pain, back pain, visceral pain, cancer pain, algesia, neuralgia, migraine, neuropathies, diabetic neuropathy, sciatica, HIV-related neuropathy, post-herpetic neuralgia, fibromyalgia, nerve injury, ischaemia, neurodegeneration, stroke, post stroke pain, multiple sclerosis, respiratory diseases, asthma, cough, COPD, inflammatory disorders, oesophagitis, gastroeosophagal reflux disorder (GERD), irritable bowel syndrome, inflammatory bowel disease, pelvic hypersensitivity, urinary incontinence, cystitis, burns, psoriasis, eczema, emesis, stomach duodenal ulcer and pruritus by administering potassium, lithium or sodium salt of N-{4-[2,4-Difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide.

In an embodiment, there is provided a method for treating diseases, conditions and/or disorders modulated by TRPA1; comprising administering a salt of compound of formula (II), or a pharmaceutical composition that comprises the salt of compound of formula (II) along with pharmaceutically acceptable excipients, wherein the salt of compound of formula (II) is a potassium salt, a sodium salt, or a lithium salt.

In an embodiment, there is provided a method for treating diseases, conditions and/or disorders modulated by TRPA1; comprising administering a solid state forms of salt of compound of formula (II), or a pharmaceutical composition that comprises the solid state forms of salt of compound of formula (II) along with pharmaceutically acceptable excipients, wherein the salt of compound of formula (II) is a potassium salt, a sodium salt, or a lithium salt.

In another embodiment, the present invention pertains to a method of treating diseases or conditions or disorders associated with TRPA1 function in a subject in need thereof by administering to the subject an effective amount of crystalline compound of formula (II) designated as Form Y.

In another embodiment, there is provided a method for treating diseases, conditions and/or disorders modulated by TRPA1; comprising administering Form X of compound of formula (II), or a pharmaceutical composition that comprises Form X of compound of formula (II) along with pharmaceutically acceptable excipients.

In another embodiment, there is provided a method for treating diseases, conditions and/or disorders modulated by TRPA1; comprising administering Form Y of compound of formula (II), or a pharmaceutical composition that comprises Form Y of compound of formula (II) along with pharmaceutically acceptable excipients.

In another embodiment, there is provided a method for treating diseases, conditions and/or disorders modulated by TRPA1; comprising administering Form Z of compound of formula (II), or a pharmaceutical composition that comprises Form Z of compound of formula (II) along with pharmaceutically acceptable excipients.

In another embodiment, the present invention pertains to a method of treating diseases or conditions or disorders associated with TRPA1 which are selected from pain, chronic pain, complex regional pain syndrome, neuropathic pain, postoperative pain, rheumatoid arthritic pain, osteoarthritic pain, back pain, visceral pain, cancer pain, algesia, neuralgia, migraine, neuropathies, diabetic neuropathy, sciatica, HIV-related neuropathy, post-herpetic neuralgia, fibromyalgia, nerve injury, ischaemia, neurodegeneration, stroke, post stroke pain, multiple sclerosis, respiratory diseases, asthma, cough, COPD, inflammatory disorders, oesophagitis, gastroeosophagal reflux disorder (GERD), irritable bowel syndrome, inflammatory bowel disease, pelvic hypersensitivity, urinary incontinence, cystitis, burns, psoriasis, eczema, emesis, stomach duodenal ulcer and pruritus by administering Form X, Form Y or Form Z of N-{4-[2,4-Difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide.

Methods of Preparation

The compounds described herein, including compounds of general formula (I), or Compound of formula (II) and specific examples can be prepared using techniques known to one skilled in the art through the reaction sequences depicted in scheme below as well as by other methods. Furthermore, in the following schemes, where specific acids, bases, reagents, coupling agents, solvents, etc. are mentioned, it is understood that other suitable acids, bases, reagents, coupling agents etc. may be used and are included within the scope of the present invention. Modifications to reaction conditions, for example, temperature, duration of the reaction or combinations thereof, are envisioned as part of the present invention. The compounds obtained by using the general reaction sequences may be of insufficient purity. These compounds can be purified by using any of the methods for purification of organic compounds known to persons skilled in the art, for example, crystallization or silica gel or alumina column chromatography using different solvents in suitable ratios. All possible geometrical isomers and stereo isomers are envisioned within the scope of this invention.

In an embodiment, there is provided process for the preparation of compound of formula (II) and its pharmaceutically acceptable salt, which process comprises following steps as shown in the below scheme 1.

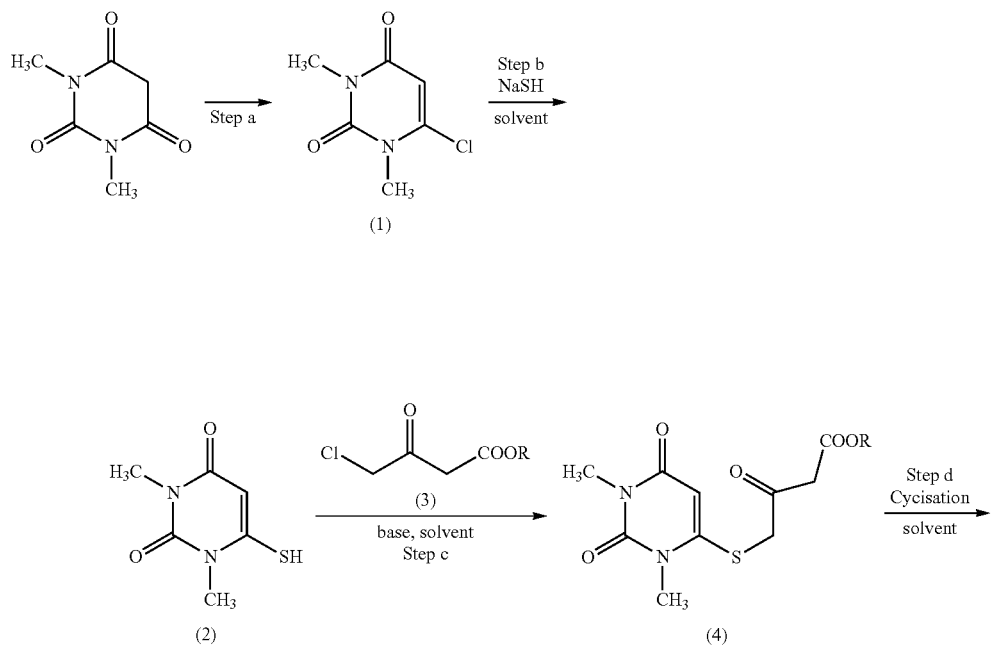

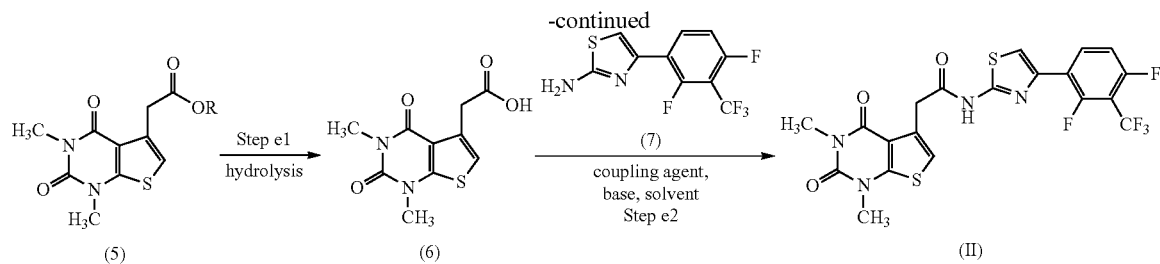

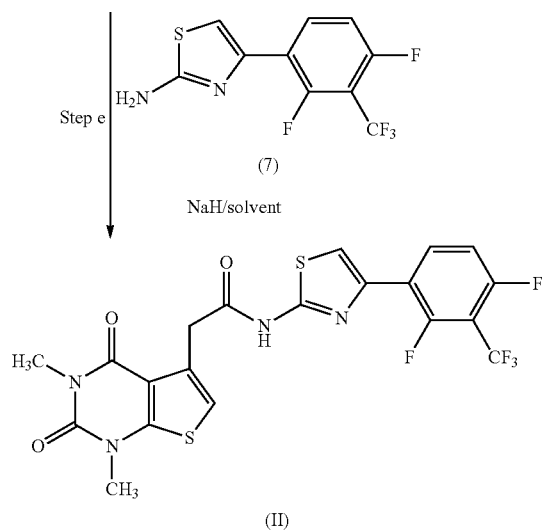

The process comprises following steps:
a) treating dimethylbarbituric acid with a suitable chlorinating agent to afford 6-chloro-1,3-dimethyluracil of formula (1);
b) treating 6-chloro-1,3-dimethyluracil of formula (1) with sodium hydrosulphide hydrate to give 6-mercapto-1,3-dimethyluracil of the formula (2);
c) treating 6-mercapto-1,3-dimethyluracil of the formula (2) with the compound of formula (3) to give ester compound of formula (4);
d) cyclising keto ester of the formula (4) to obtain thieno-pyrimidinyl ester of the formula (5);
e) reacting thieno-pyrimidinyl ester of the formula (5) with thiazole amine of the formula (7) to give compound of formula (II). Alternatively, hydrolysing compound of formula (5) to give thieno-pyrimidinyl acetic acid of the formula (6), followed by reacting compound of the formula (6) with thiazole amine of the formula (7).

Step (a) involves reacting dimethylbarbituric acid with chlorinating agent. The chlorinating agent comprises phosphorous trichloride, phosphorous pentachloride or phosphorous oxychloride. The reaction may be carried out in a suitable solvent such as water at a suitable temperature which involves heating the reaction mixture at reflux temperature.

Step (b) involves treating compound of formula (1) with sodium hydrosulphide hydrate to give compound of the formula (2). The reaction may be carried out in a suitable solvent. The suitable solvent comprises $C_1$-$C_6$ alcohols, chlorinating solvent, water and/or mixtures thereof. Preferably the suitable solvent(s) may be used in step (b) are ethanol, chloroform and/or combination thereof. The reaction is preferably carried out a temperature range of 0-5° C. Preferably, the reaction may be carried out using ethanol as solvent followed by stirring the reaction mixture at room temperature overnight. The reaction mixture was evaporated to dryness under vacuum and the residue obtained was dissolved in water and extracted with dichloromethane. The aqueous layer was separated and acidified with 1 N HCl. The precipitated solid was filtered, washed with water and dried to obtain the compound of formula (2).

Step (c) involves reacting compound of formula (2) with the compound of formula (3, wherein R is ($C_1$-$C_4$)alkyl, e.g. methyl or ethyl) to give ester compound of formula (4, wherein R is ($C_1$-$C_4$)alkyl). The reaction may be optionally carried out in the presence of suitable base and suitable solvent(s). Bases that are useful in the reaction include, but are not limited to, organic bases, such as, tertiary amines, e.g., triethylamine, N,N-diisopropylethylamine, N,N-diethylethanamine, N-(1-methylethyl)-2-propanamine, 4-ethylmorpholine, 1,4-diazabicyclo[2.2.2]-octane, N-methylmorpholine, pyridine, and the like; or any mixtures thereof.

The reaction may be carried out in a suitable solvent or mixture of solvents. In one of the embodiments the reaction is carried out in a chlorinating solvent. The chlorinating solvent includes dichloromethane, 1,2-dichloroethane, chloroform, and carbon tetrachloride. Other suitable solvent may also be used.

The reaction may be carried out at a suitable temperature, preferably at room temperature (~25 to 30° C.).

Step (d) involves cyclising ester compound of formula (4) to obtain thieno[2,3-d]pyrimidinyl ester of the formula (5). The cyclization step may be carried out using a suitable dehydrating agent such as polyphosphoric acid, phosphorous pentoxide, zinc chloride, sulphuric acid, boron trifluoride or $Pd_2(dba)_3$ and xantphos. The reaction may be carried out in a suitable solvent or it may be carried out in the absence of a solvent. Advantageously, the reaction may be carried out at an elevated temperature such as 60-70° C. or it may be carried out at a reflux temperature of the solvent employed in the reaction.

Step (e) involves reacting the compound of formula (5) with amine of the formula (7) in the presence of a suitable base and suitable solvent to give compound of formula (II). The reaction may be carried out in the presence of suitable base. The suitable base includes inorganic and organic bases such as, for example sodium hydride. The suitable solvent may include, but not limited to, hydrocarbon solvents such as toluene, xylene, n-heptane, cyclohexane and n-hexane. The reaction may be carried out at an elevated temperature such as reflux temperature of the solvent or mixture of solvents employed. Preferably, the base used in step (e) is sodium hydride and solvent such as toluene.

In an alternate pathway, Step (e1) involves ester hydrolysis of the compound of formula (5) to obtain compound of formula (6). In this step the ester hydrolysis can be carried out using acid (e.g. $H_2SO_4$ or HCl) or base (e.g., sodium hydroxide, potassium hydroxide or lithium hydroxide) under suitable condition (e.g. at reflux temperature) in the presence of suitable solvent such as alcohol, water or 1,4-dioxane and/or combination thereof. Preferably the ester hydrolysis can be carried out using 3N or 6N $H_2SO_4$ in 1,4-dioxane at reflux temperature.

In next Step (e2), the compound of formula (6) may be coupled with compound of formula (7) in the presence of coupling reagent. The suitable coupling reagents include but are not limited to N-hydroxybenzotriazole (HOBT), 4,5-dicyanoimidazole, dicyclohexylcarbodiimide (DCC), dicyclopentylcarbodiimide, diisopropylcarbodiimide, 1-ethyl-3-(3-dimethylaminopropyl)carbodiimide hydrochloride (EDCI.HCl), 1,1'-carbonyldiimidazole, cyclohexylisopropylcarbodiimide (CIC), bis[[4-(2,2-dimethyl-1,3-dioxolyl)]-methyl]carbodiimide, N,N'-bis(2-oxo-3-oxazolidinyl)-phosphinic chloride (BOP-Cl). The coupling may be carried out in the presence of suitable base and a suitable solvent. Alternatively, the acid group of compound of formula (6) can be converted to its acid chloride by treating it with chlorinating agent such as oxalyl chloride or thionyl chloride in suitable solvent, followed by treating the acid chloride derivative with compound of formula (7) in the presence of base such as triethylamine, pyridine or diisopropyl amine in suitable solvent to give compound of formula (II).

In another embodiment, there is provided process for the preparation of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide or pharmaceutically acceptable salt thereof, which process comprises the step of
  (a) treating dimethylbarbituric acid with a suitable chlorinating agent to afford 6-chloro-1,3-dimethyluracil of formula (1); and

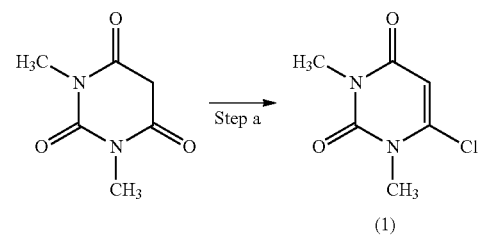

(b) treating 6-chloro-1,3-dimethyluracil of formula (1) with sodium hydrosulphide hydrate to give 6-mercapto-1,3-dimethyluracil of the formula (2).

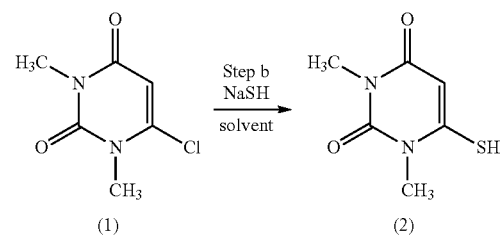

(c) treating 6-mercapto-1,3-dimethyluracil of the formula (2) with the compound of formula (3) wherein R is $(C_1-C_4)$alkyl, to give ester compound of formula (4); and

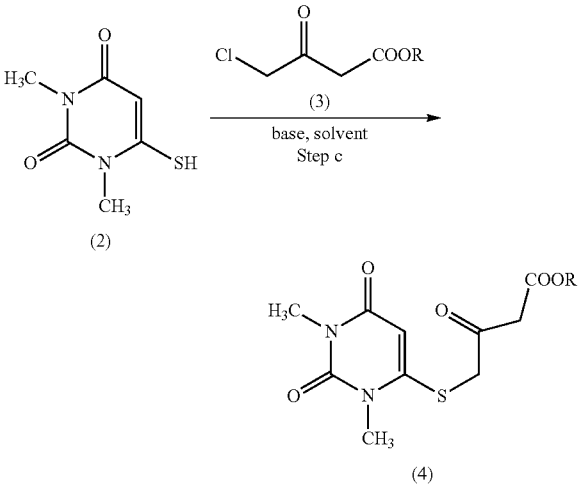

(d) cyclising keto ester of the formula (4) to obtain thieno-pyrimidinyl ester of the formula (5)

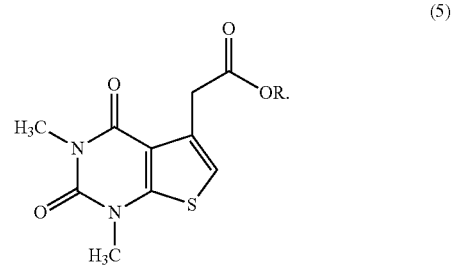

Step (a) involves reacting dimethylbarbituric acid with chlorinating agent. The chlorinating agent comprises phosphorous trichloride, phosphorous pentachloride or phosphorous oxychloride. The reaction may be carried out in a suitable solvent such as water at a suitable temperature which involves heating the reaction mixture at reflux temperature.

Step (b) involves treating compound of formula (1) with sodium hydrosulphide hydrate to give compound of the formula (2). The reaction may be carried out in a suitable solvent. The suitable solvent comprises $C_1$-$C_6$ alcohols, chlorinating solvent, water and/or mixtures thereof. Preferably the suitable solvent(s) may be used in step (b) are ethanol, chloroform and/or combination thereof. The reaction is preferably carried out a temperature range of 0-5° C. Preferably, the reaction may be carried out using ethanol as solvent followed by stirring the reaction mixture at room temperature overnight. The reaction mixture was evaporated to dryness under vacuum and the residue obtained was dissolved in water and extracted with dichloromethane. The aqueous layer was separated and acidified with 1 N HCl. The precipitated solid was filtered, washed with water and dried to obtain the compound of formula (2).

Step (c) involves reacting compound of formula (2) with the compound of formula (3, wherein R is ($C_1$-$C_4$)alkyl, e.g. methyl or ethyl) to give ester compound of formula (4, wherein R is ($C_1$-$C_4$)alkyl). The reaction may be optionally carried out in the presence of suitable base and suitable solvent(s). Bases that are useful in the reaction include, but are not limited to, organic bases, such as, tertiary amines, e.g., triethylamine, N,N-diisopropylethylamine, N,N-diethylethanamine, N-(1-methylethyl)-2-propanamine, 4-ethylmorpholine, 1,4-diazabicyclo[2.2.2]-octane, N-methylmorpholine, pyridine, and the like; or any mixtures thereof.

The reaction may be carried out in a suitable solvent or mixture of solvents. In one of the embodiments the reaction is carried out in a chlorinating solvent. The chlorinating solvent includes dichloromethane, 1,2-dichloroethane, chloroform, and carbon tetrachloride. Other suitable solvent may also be used.

The reaction may be carried out at a suitable temperature, preferably at room temperature (~25 to 30° C.).

In another embodiment of the present invention there is provided process for the preparation of compound of formula (II) and its pharmaceutically acceptable salt, comprising the steps of:
f) reacting thioglycolic ester of the formula (4) with amine of the formula (7) to afford thioglycolic amide of formula (8); and
g) cyclising thioglycolic amide of formula (8)

The steps (f) and (g) mentioned above are depicted in Scheme 2

Scheme 2:

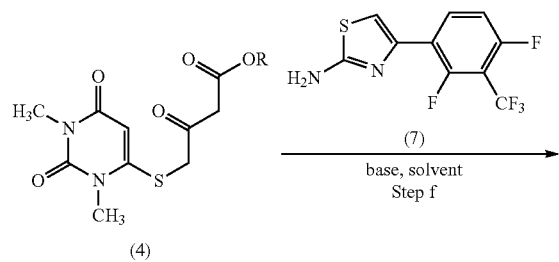

(4)

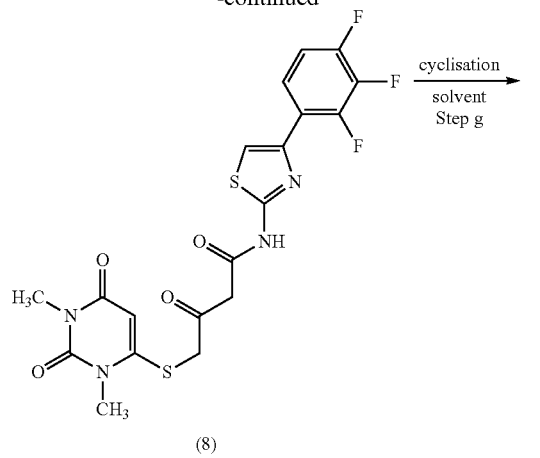

(8)

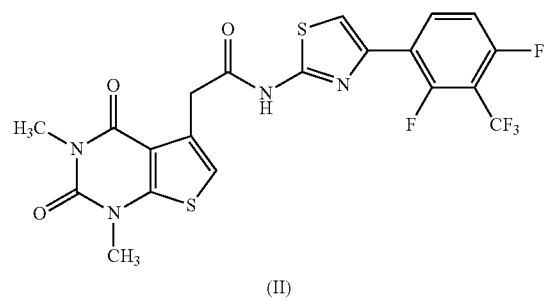

(II)

In step (f), thioglycolic ester of the formula (4) (wherein R is ($C_1$-$C_4$)alkyl e.g. methyl or ethyl) is reacted with amine of the formula (7) in the presence of a suitable base and suitable solvent to give thioglycolic amide of the formula (8). The suitable base may include organic or inorganic base. In one of the embodiments, the base used is sodium hydride. The suitable solvent may include, but does not limit to, hydrocarbon solvents such as toluene, xylene, n-heptane, cyclohexane and n-hexane. In the next step (g), the compound of formula (8) is cyclized to obtain the compound of formula (II). The cyclization may be carried out using dehydrating agent. The suitable dehydrating agents are such as polyphosphoric acid, phosphorous pentoxide, zinc chloride, sulphuric acid and boron trifluoride. The reaction may be carried out in a suitable solvent. The suitable solvent may include, but are not limited to, hydrocarbon solvents such as toluene, xylene, n-heptane, cyclohexane and n-hexane or it may be carried out in the absence of a solvent. Advantageously, the reaction may be carried out at an elevated temperature such as 60-70° C. or it may be carried out at a reflux temperature of the solvent employed in the reaction.

In another embodiment, the present invention pertains to process for the preparation of compound of formula (II) and its pharmaceutically acceptable salt, which comprises the following steps:
h) reacting thieno[2,3-d]pyrimidinyl acetic acid of the formula (6) with 1H-1,2,3-benzotriazole (9) to get N-acylbenzotrazole derivative of the formula (10); and
i) reacting N-acylbenzotrazole derivative of the formula (10) with amine compound of formula (7) to afford the compound of the formula (II).

The steps (h) and (i) mentioned above are depicted in Scheme 3.

Scheme 3:

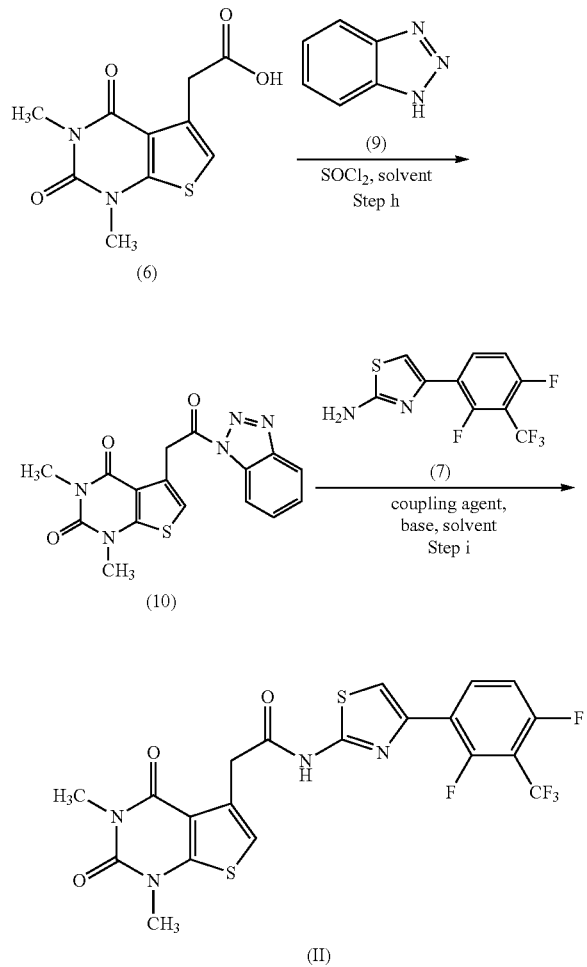

The steps (j), (k) and (l) mentioned above are depicted in Scheme 4.

Scheme 4:

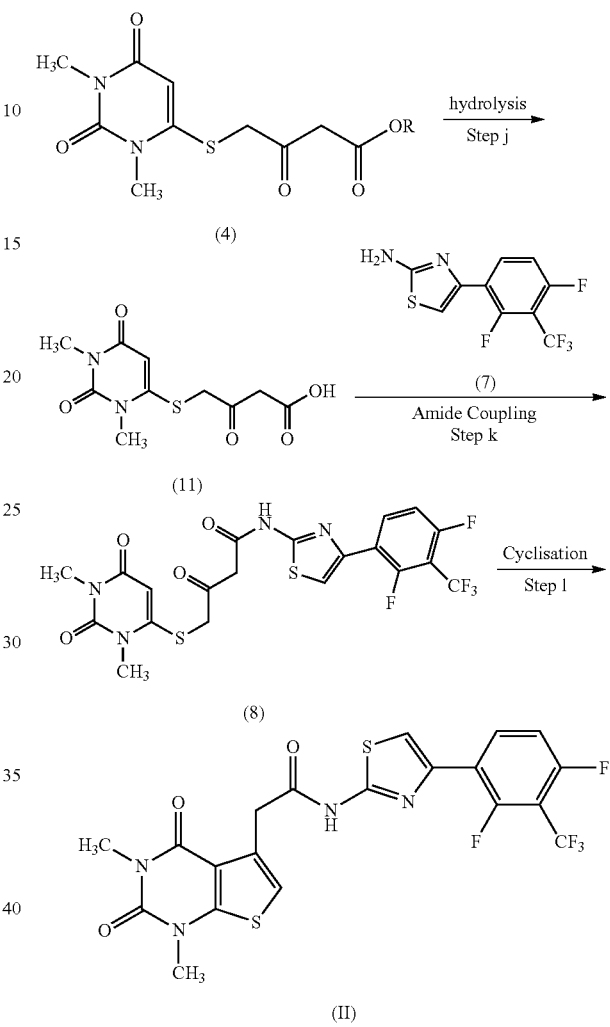

In this approach, in step (h) thieno[2,3-d]pyrimidinyl acetic acid of the formula (6) is converted to N-acylbenzotriazole derivative of the formula (10) by the reaction of compound of formula (6) with 1H-1,2,3-benzotriazole (9) in the presence of $SOCl_2$ and in a suitable solvent. In one of the embodiments the suitable solvent is chlorinated solvent for example dichloromethane. In next step (i), reaction of N-acylbenzotrazole derivative of the formula (10) with amine compound of the formula (7) may be carried out in the presence of suitable base to afford the compound of the formula (II).

In another embodiment, there is provided another process for the preparation of compound of formula (II) and its pharmaceutically acceptable salt, which comprises the following steps:

j) hydrolyzing the compound of formula (4) to get the corresponding acid compound of formula (11);

k) reacting the compound of formula of (11) with the compound of formula (7) to get the compound of formula (8); and l) cyclising compound of the formula (8) to afford the compound of the formula (II).

In this approach, hydrolysis of thioglycolic ester of the formula (4) (wherein R is ($C_1$-$C_4$)alkyl, e.g. methyl or ethyl) in the presence of suitable base or acid gives thioglycolic acid of the formula (11). The coupling of compound of formula (11) with compound of formula (7) in the presence of suitable coupling agent and a suitable solvent gives thioglycolic amide compound of formula (8). The cyclization of thioglycolic amide compound of (8) in the presence of dehydrating agent as described in Scheme 1 affords desired compound of the formula (II).

In a further embodiment, there is provided process for the preparation of compound of formula (5) which comprises the following steps:

m) reacting compound of formula (12) with sodium sulfide hydrate and ethyl cyano acetate to get compound of formula (13);

n) brominating the compound of formula (13) to get compound of formula (14); and o) converting compound of formula (14) to compound of formula (5). The steps (m), (n) and (o) mentioned above are depicted in Scheme 5.

Scheme 5:

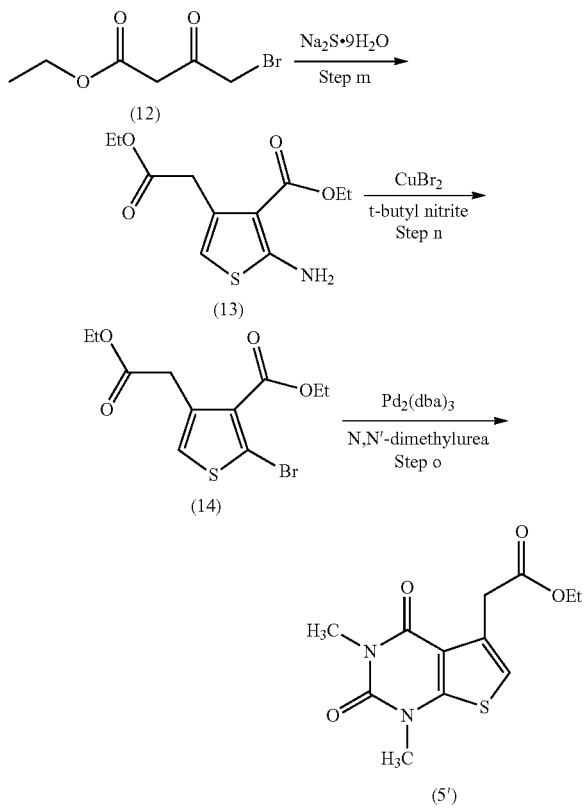

Herein ethyl 4-bromoacetoacetate and ethylcyanoacetate can be coupled in the presence of sodium sulfide hydrate to give amino compound of formula (13). The obtained product may be treated with t-butyl nitrite followed by copper bromide to afford bromo compound of formula (14). The cyclization of (14) using N,N-dimethylurea in presence of palladium reagent such as tris(dibenzylideneacetone)dipalladium(0) (Pd$_2$(dba)$_3$) provides the desired ester compound of formula (5').

In a further embodiment, there is provided process for the preparation of compound of formula (7) which comprises treating a solution of 1-[2,4-difluoro-3-(trifluoromethyl)phenyl]ethanone (16) in glacial acetic acid with liquid bromine to obtain the crude bromo derivative. The crude bromo derivative, without further purification can be treated with thiourea to afford the 2-amino-4-aryl-thiazole compound (7). Alternatively, 1-[2,4-difluoro-3-(trifluoromethyl)phenyl]ethanone (16), iodine and thiourea in ethanol can be refluxed to afford the 4-[2,4-difluoro-3-(trifluoromethyl)phenyl]-1,3-thiazol-2-amine compound (7).

Scheme 6:

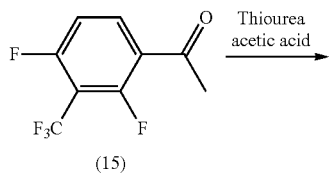

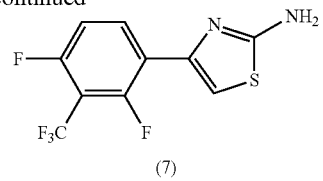

Pharmaceutical Compositions

The compounds of the invention are typically administered in the form of a pharmaceutical composition. Such compositions can be prepared using procedures well known in the pharmaceutical art and comprise at least one compound of the invention. The pharmaceutical composition of the present patent application comprises one or more compounds described herein and one or more pharmaceutically acceptable excipients. Typically, the pharmaceutically acceptable excipients are approved by regulatory authorities or are generally regarded as safe for human or animal use. The pharmaceutically acceptable excipients include, but are not limited to, carriers, diluents, glidants and lubricants, preservatives, buffering agents, chelating agents, polymers, gelling agents, viscosifying agents, solvents and the like.

Examples of suitable carriers include, but are not limited to, water, salt solutions, alcohols, polyethylene glycols, peanut oil, olive oil, gelatin, lactose, terra alba, sucrose, dextrin, magnesium carbonate, sugar, amylose, magnesium stearate, talc, gelatin, agar, pectin, acacia, stearic acid, lower alkyl ethers of cellulose, silicic acid, fatty acids, fatty acid amines, fatty acid monoglycerides and diglycerides, fatty acid esters, and polyoxyethylene.

The pharmaceutical composition may also include one or more pharmaceutically acceptable auxiliary agents, wetting agents, suspending agents, preserving agents, buffers, sweetening agents, flavoring agents, colorants or any combination of the foregoing.

The pharmaceutical compositions may be in conventional forms, for example, capsules, tablets, solutions, suspensions, injectables or products for topical application. Further, the pharmaceutical composition of the present invention may be formulated so as to provide desired release profile.

Administration of the compounds of the invention, in pure form or in an appropriate pharmaceutical composition, can be carried out using any of the accepted routes of administration of pharmaceutical compositions. The route of administration may be any route which effectively transports the active compound of the patent application to the appropriate or desired site of action. Suitable routes of administration include, but are not limited to, oral, nasal, buccal, dermal, intradermal, transdermal, parenteral, rectal, subcutaneous, intravenous, intraurethral, intramuscular, or topical.

Solid oral formulations include, but are not limited to, tablets, capsules (soft or hard gelatin), dragees (containing the active ingredient in powder or pellet form), troches and lozenges.

Liquid formulations include, but are not limited to, syrups, emulsions, and sterile injectable liquids, such as suspensions or solutions.

Topical dosage forms of the compounds include ointments, pastes, creams, lotions, powders, solutions, eye or ear drops, impregnated dressings, and may contain appropriate conventional additives such as preservatives, solvents to assist drug penetration.

The pharmaceutical compositions of the present patent application may be prepared by conventional techniques, e.g., as described in *Remington: The Science and Practice of Pharmacy*, 20th Ed., 2003 (Lippincott Williams & Wilkins).

Suitable doses of the compounds for use in treating the diseases and disorders described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects. Mode of administration, dosage forms, and suitable pharmaceutical excipients can also be well used and adjusted by those skilled in the art. All changes and modifications are envisioned within the scope of the present patent application.

DEFINITIONS

The term "crystalline" as used herein, means having a regularly repeating arrangement of molecules or external face planes.

The term "amorphous" as used herein, means essentially without regularly repeating arrangement of molecules or external face planes.

Unless stated otherwise, percentages stated throughout this specification are weight/weight (w/w) percentages.

The term "mixture" as used herein, means a combination of at least two substances, in which one substance may be completely soluble, partially soluble or essentially insoluble in the other substance.

The term "treating" or "treatment" of a state, disorder or condition includes; (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; or (c) relieving the disease, i.e., causing regression of the state, disorder or condition or at least one of its clinical or subclinical symptoms.

The term "subject" includes mammals (especially humans) and other animals, such as domestic animals (e.g., household pets including cats and dogs) and non-domestic animals (such as wildlife).

All powder X-ray diffraction patterns were obtained using: Panalytical X'PERT-PRO diffractometer model and measured with Cu-Kα1 radiation at wavelength of 1.54060 A°. The obtained powder X-ray diffraction profiles were integrated using X'Pert High Score Plus Software.

It is meant to be understood that peak heights in a powder x-ray diffraction pattern may vary and will be dependent on variables such as the temperature, crystal size, crystal habit, sample preparation or sample height in the analysis well of the Scintagx2 Diffraction Pattern System.

All FTIR spectra were recorded using KBr on Perkin-Elmer instrument (Model: Spectrum One). The data was processed using Spectrum One Software.

As used herein, the term "average particle size" (or synonymously, "mean particle size") refers to the distribution of particles, wherein about 50 volume percent of all the particles measured have a size less than the defined average particle size value and about 50 volume percent of all measurable particles measured have a particle size greater than the defined average particle size value. This can be identified by the term "$D_{50}$" or "d (0.5)".

The term "$D_{10}$" refers to the distribution of particles, wherein about 10 volume percent of all the particles measured have a size less than the defined particle size value. This can be identified by the term "d(0.1)" as well. Similarly, as used herein, the term "$D_{90}$" refers to the distribution of particles, wherein about 90 volume percent of all the particles measured have a size less than the defined particle size value. This can be identified by the term or "d (0.9)" as well.

The average particle size can be measured using various techniques like laser diffraction, photon correlation spectroscopy and Coulter's principle. Typically, instruments like ZETASIZER® 3000 HS (Malvern® Instruments Ltd., Malvern, United Kingdom), NICOMP 388™ ZLS system (PSS-Nicomp Particle Sizing Systems, Santa Barbara, Calif., USA), or Coulter Counter are generally used to determine the mean particle size. Preferably, Mastersizer 2000 (Malvern® Instruments Ltd., Malvern, United Kingdom) is used to determine the particle size of the particles.

EXPERIMENTAL

Unless otherwise stated, work-up includes distribution of the reaction mixture between the organic and aqueous phase indicated within parentheses, separation of layers and drying the organic layer over sodium sulphate, filtration and evaporation of the solvent. Purification, unless otherwise mentioned, includes purification by silica gel chromatographic techniques, generally using ethyl acetate/petroleum ether mixture of a suitable polarity as the mobile phase. Use of a different eluent system is indicated within parentheses. The following abbreviations are used in the text: DMSO-$d_6$: Hexadeuterodimethyl sulfoxide; AcOEt: ethyl acetate; equiv. or eq.: equivalents; h: hour(s); L: liters; $CDCl_3$: deuterated chloroform; $CHCl_3$: chloroform; EtOAc or EA: ethyl acetate; DCM: dichloromethane; DMSO: dimethyl sulfoxide; DMF: N,N-dimethylformamide; DSC: Differential scanning calorimetry; EDCI: 1-ethyl-3-(3-dimethylaminopropyl)carbodiimide); HOBt: hydroxybenzotriazole; $Cs_2CO_3$: Cesium carbonate; $K_2CO_3$: potassium carbonate; MeOH: methanol; EtOH: ethanol; $NaHCO_3$: sodium bicarbonate; $Na_2CO_3$: sodium carbonate; NaOtBu: sodium tertiarybutoxide; KOtBu: potassium tertiarybutoxide; $PCl_5$: phosphorous pentachloride; $POCl_3$: phosphorous oxychloride; THF: tetrahydrofuran; TEA: triethylamine; TBAF: tetra-n-butylammonium fluoride; J: Coupling constant in units of Hz; RT or rt: room temperature (22-26° C.); q.s.: quantity sufficient; aq.: aqueous; equiv. or eq.: equivalents; conc.: concentrated; min: minutes; i.e.: that is; h or hrs: hours.

The parameters mentioned in the description which characterize the polymorphic nature, moisture content, particle size, stability studies by the measuring techniques and methods described below:

Hygroscopicity Study:

Hygroscopicity study was performed under the following conditions: The material was exposed to relative humidity (for example 60%, 80%, 90%) at 25° C. condition. The material was thinly spread in dried and pre-weighed Petri plate. The plate was exposed to the relative humidity conditions at 25° C. The Petri plate was withdrawn at regular intervals and weighed. Withdrawn samples were tested for description and moisture content by Karl Fischer method.

Particle Size Distribution Studies:

The particle size distribution was measured using Mastersizer 2000 (Malvern® instruments Ltd., Malvern, United Kingdom) with following measuring equipment and settings:

Instrument: Malvern Mastersizer 2000

Sample Handling Unit: Hydro 2000S (A)

Dispersant RI: 1.375

Dispersant: 0.1% w/v Dioctyl sulfosuccinate sodium salt in n-Hexane

Sample quantity: 100 mg

Measurement time: 5.0 sec

Powder X-Ray Diffraction Studies:

All powder X-ray diffraction patterns were obtained using: Panalytical X'PERT-PRO diffractometer model and measured with Cu-Kα1 radiation at wavelength of 1.54060 A°. The obtained powder X-ray diffraction profiles were integrated using X'Pert High Score Plus Software.

Stability Test Methods:

The salts of compound of formula II were stored under conditions as shown in Table 11 and a total amount of degradation products (related substances) and single maximum impurity formed during storage was estimated according to following protocol:

HPLC Conditions:

Apparatus: A High Performance Liquid Chromatograph equipped with quaternary gradient pumps, variable wavelength UV detector attached with data recorder and Integrator software or equivalent.

Column: Phenomenex Prodigy, 250 mm×4.6 mm, 5.0 or equivalent

Mobile phase: A: Buffer B: Acetonitrile (for sodium salt), acetonitrile:methanol (6:4) for potassium salt Buffer: 0.1% Formic acid in water Diluent: Acetonitrile Flow Rate: 1.0 mL/minute Detection wavelength: UV 265 nm Column temperature: 40° C.

Injection volume: 20 μl

Run time: 60 min

Test Solution:

10 mg of compound was weighed and transferred it into a 20 mL volumetric flask. Dimethylsulfoxide was added and it was sonicated to dissolve. The diluent was added to make up the solution to the mark of the flask.

Procedure:

The equal volumes of blank (diluent) and test solution were separately injected into the liquid chromatograph. The responses were recorded eliminating the peaks due to blank and the chromatographic purity by area was calculated by normalization method.

The following examples are presented to provide what is believed to be the most useful and readily understood description of procedures and conceptual aspects of this invention. The examples provided below are merely illustrative of the invention and are not intended to limit the same to disclosed embodiments. Variations and changes obvious to one skilled in the art are intended to be within the scope and nature of the invention.

Intermediate 1

Preparation of 4-[2,4-difluoro-3-(trifluoromethyl)phenyl]-1,3-thiazol-2-amine

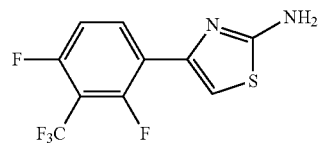

Method A:

Step 1: Synthesis of 1-bromo-2,4-difluro-3-(trifluoromethyl)benzene

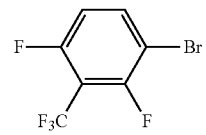

A mixture of 2,6-difluorobenzotrifluoride (100 g, 0.55 mol) and iron powder (20 g, 0.36 mol) was heated to 50-55° C. and the reaction mixture was stirred for 5 min. Bromine (124 g, 0.77 mol) was added slowly to the reaction mixture at 50-55° C. and it was further stirred for 2.0 h at 65-70° C. After completion of the reaction, it was cooled to room temperature and diluted with dichloromethane (800 ml). The reaction mixture was filtered through a hyflo bed and washed with dichloromethane (200 ml). The filtrate obtained was washed with 10% sodium thiosulphate solution (200 ml) followed by water (200 ml) and saturated solution of brine (100 ml). The organic extract was separated, dried ($Na_2SO_4$) and concentrated to obtain 130 g of the product.
$^1$H NMR (300 MHz, $CDCl_3$): δ 7.40 (t, 1H), 8.16 (q, 1H).

Step 2:—Synthesis of 1-(2,4-difluoro-3-(trifluoromethyl)phenyl)ethanone

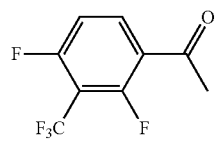

To a solution of 1-bromo-2,4-difluoro-3-(trifluoromethyl)benzene (10 g, 0.038 mol) in dry tetrahydrofuran (325 ml) was added magnesium metal (7.8 g, 0.33 mol) and the mixture was heated to 60-65° C. to initiate the reaction. Again 1-bromo-2,4-difluoro-3-(trifluoromethyl)benzene (55 g, 0.21 mol) was added carefully and mixture was further stirred at 60-65° C. for 1.0 h. The reaction mixture was cooled to 25-30° C. and cadmium chloride (6.5 g, 0.035 mol) was added and stirred for 30 min. Acetic anhydride (32.3 g, 0.32 mol) was added slowly and the mixture was stirred for 1 h at room temperature. The mixture was quenched with dilute hydrochloric acid and extracted with ethyl acetate. The combined organic extract was washed with water, brine and dried (Na$_2$SO$_4$). The solvent was evaporated under reduced pressure to obtain 65 g of the product as oily mass. The product was purified by high vacuum distillation to give 41 g of the title product. $^1$H NMR (300 MHz, CDCl$_3$): δ 8.14 (q, 1H), 7.11 (t, 1H), 2.66 (d, 3H).

Step 3: Synthesis of 4-[2,4-difluoro-3-(trifluoromethyl)phenyl]-1,3-thiazol-2-amine

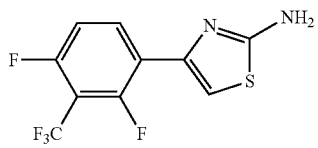 [SMILES: Nc1nc(-c2ccc(F)c(C(F)(F)F)c2F)cs1]

To a solution of 1-[2,4-difluoro-3-(trifluoromethyl)phenyl]ethanone (20 g, 0.089 mol) in acetic acid (80 mL) was slowly added bromine (18 g, 0.11 mol) in acetic acid (80 mL) at 25-30° C. The reaction mixture was heated to 55-60° C. and further stirred for 30 min. Thiourea (15 g, 0.19 mol) was added in one lot and temperature was raised to 85-90° C. The reaction mass was stirred at 85-90° C. till the completion of the reaction. Acetic acid was evaporated under reduce pressure and diluted with water (200 mL) and pH of the solution was adjusted to 9-10 by the addition of 30% sodium hydroxide solution. The reaction mass was stirred for 1.0 h at 25-30° C. and the precipitated product was collected by filtration. The product was washed with water and the wet cake was dissolved in ethyl acetate (200 ml) and dried over anhydrous sodium sulphate (Na$_2$SO$_4$). Activated charcoal (2 g) was added to the solution and stirred for 30 min. The reaction mixture was filtered through hyflo bed to remove charcoal. The filtrate was evaporated under reduce pressure. Hexane (40 ml) was added to the residue. The reaction mass was stirred for 1.0 h and product was collected by filtration. The solid was washed with hexane (40 ml) and dried at 45-50° C. to obtain 19.5 g of the title product. $^1$H NMR (300 MHz, CDCl$_3$): δ 8.28 (q 1H), 7.41 (t 1H), 7.19 (s, 2H), 7.05 (d, 1H).
Method B:

Step 1: Synthesis of 2,4-difluoro-3-(trifluoromethyl)benzoic acid

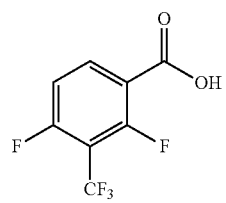 [SMILES: O=C(O)c1ccc(F)c(C(F)(F)F)c1F]

To a stirred solution of 2,6-difluorobenzotrifluoride (250 g, 1.37 mol) in a mixture of THF (1.5 L) and diethyl ether (1.5 L) was added drop wise n-butyllithium (1.0 L, 1.60 mol) at −65° C. to −70° C. and the resulting mixture was stirred for 1 h. Dry carbon dioxide gas was purged in to reaction mass and the temperature was allowed to warm from −65° C. to 30° C. during 5 h. The reaction mixture was quenched into 3N hydrochloric acid and pH was adjusted to about 2. The reaction mixture was extracted with ethyl acetate and layers were separated. The organic layer was washed with water followed by brine. The organic layer was distilled off and the viscous residue was diluted with hexane (500 ml). The precipitated solid was collected by filtration and dried to obtain 225 g of the title product (72%).

Step 2: Synthesis of 2,4-difluoro-N-methoxy-N-methyl-3-(trifluoromethyl)benzamide

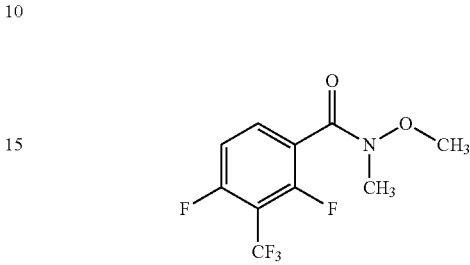

To a stirred solution of 2,4-difluoro-3-(trifluoromethyl) benzoic acid (150 g, 0.66 mol) in dichloromethane (1.5 L) was added DMF (15 ml) followed by drop wise addition of oxalyl chloride (76.5 ml, 0.88 mol) at room temperature and the resulting mixture was stirred for 3 to 7 h at same temperature. After completion of the reaction, dichloromethane was distilled out under vacuum. The acid chloride obtained was dissolved in dichloromethane (750 ml) and the solution was used for the next step. To a stirred solution of N,O-dimethyl hydroxyl amine hydrochloride (70.5 g, 0.72 mol) in dichloromethane (750 ml) was added triethylamine (225 ml) and the resulting mixture was stirred for 1 h to result a white slurry. The above acid chloride in dichloromethane was added and the reaction mixture was stirred for 2 h. The mixture was quenched with water (1.5 L) and extracted with dichloromethane (2×350 mL). The combined extract was washed with water followed by brine. The organic phase was dried over Na$_2$SO$_4$ and the solvent was distilled off under vacuum to obtain 175 g (97%) of the title compound.

Step 3: Synthesis of 1-[2,4-difluoro-3-(trifluoromethyl)phenyl]ethanone

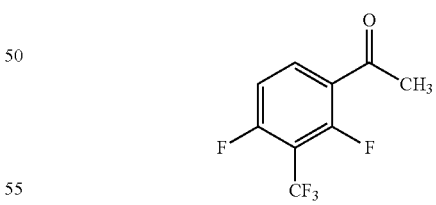

A solution of 2,4-difluoro-N-methoxy-N-methyl-3-(trifluoromethyl)benzamide (165 g, 0.61 mol) in dry THF (825 ml) was added to a stirred 1.4 M solution of methyl magnesium bromide in dry THF (561 ml, 0.78 mol) and the resulting mixture was stirred at room temperature for 2 h. The reaction mixture was quenched with 10% aqueous solution of ammonium chloride (1.65 L) and extracted with ethyl acetate (2×825 ml). The combined organic layers were dried over Na$_2$SO$_4$ and the solvent was distilled off under vacuum to give 105 g (76%) of the title compound.

Step 4: Synthesis of 4-[2,4-difluoro-3-(trifluoromethyl)phenyl]-1,3-thiazol-2-amine

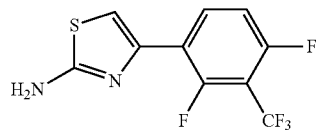

To a stirred solution of 1-[2,4-difluoro-3-(trifluoromethyl)phenyl]ethanone (664 g, 2.96 mol) in acetic acid (3.4 L) was drop wise added a solution of bromine (193 ml, 3.76 mol) in acetic acid (2.6 L) at room temperature and the resulting mixture was stirred at 55-60° C. for 30 min. Thiourea (477 g, 6.22 mol) was added and mixture was stirred at 85-90° C. for 3 h. After completion of reaction, acetic acid was evaporated under vacuum. The reaction mixture was cooled to room temperature, diluted with water (6.6 L). The pH of the mixture was adjusted to 9-10 using 30% sodium hydroxide solution and was stirred for 3 h. The mixture was filtered and product was washed with water. The wet material was dissolved in ethyl acetate (4.0 L) and 60 g charcoal was added and it was stirred for 30 min. The mixture was filtered through celite and the filtrate was dried over $Na_2SO_4$. Eethyl acetate was evaporated and residue obtained was stirred in hexane (1.3 L) for 1 h. The solid product separated out was collected by filtration to obtain 640 g (76%) of title product.

Purification of 4-[2,4-difluoro-3-(trifluoromethyl)phenyl]-1,3-thiazol-2-amine Method I:

Step-1: Preparation of malonate salt of 4-[2,4-difluoro-3-(trifluoromethyl)phenyl]-1,3-thiazol-2-amine To a stirred solution of 4-[2,4-difluoro-3-(trifluoromethyl)phenyl]-1,3-thiazol-2-amine (5.0 g, 0.017 mol) in ethyl acetate (20 ml) was added malonic acid (2.25 g, 0.021 mol) and the reaction mixture was stirred for 1 h. Hexane (40 ml) was added to the mixture and precipitated salt was collected by filtration and dried to yield 6.3 g (91%) of the product. $^1H$ NMR (300 MHz, $CDCl_3$): δ 12.6 (b 2H), 8.2 (q, 1H), 7.4 (t, 1H), 7.2 (s, 2H), 7.0 (d, 1H), 3.2 (s, 2H).

Step 2: Preparation of 4-[2,4-difluoro-3-(trifluoromethyl)phenyl]-1,3-thiazol-2-amine To a stirred solution of malonate salt of 4-[2,4-difluoro-3-(trifluoromethyl)phenyl]-1,3-thiazol-2-amine in ethyl acetate or dichloromethane was added aqueous solution of sodium hydroxide followed by workup to obtain 4-[2,4-difluoro-3-(trifluoromethyl)phenyl]-1,3-thiazol-2-amine.

Method II:

Step 1: Preparation of PTSA salt of 4-[2,4-difluoro-3-(trifluoromethyl)phenyl]-1,3-thiazol-2-amine To a stirred solution of 4-[2,4-difluoro-3-(trifluoromethyl)phenyl]-1,3-thiazol-2-amine (240 g, 0.85 mol) in ethyl acetate (1.4 L) was added p-toluenesulphonic acid (162 g, 0.85 mol) and the reaction mixture was stirred for 1 h. The reaction mixture was heated to 75-80° C. and methanol (960 ml) was drop wise added to it. The reaction mixture was cooled to room temperature and stirred for 4 h at same temperature. The solid obtained was filtered and dried to yield 286 g (71%) of the product as white solid. $^1H$ NMR (300 MHz): δ 8.1 (q, 1H), 7.5 (t, 1H), 7.4 (d, 2H), 7.1 (d, 2H), 7.0 (d, 1H), 2.2 (s, 3H).

Step 2: Preparation of 4-[2,4-difluoro-3-(trifluoromethyl)phenyl]-1,3-thiazol-2-amine To a stirred solution of PTSA salt in ethyl acetate or dichloromethane was basified to pH 12 using aqueous solution of sodium hydroxide. The workup and isolation of the product provided free thiazole amine as a white solid.

Method C:

Alternatively, 4-[2,4-difluoro-3-(trifluoromethyl)phenyl]-1,3-thiazol-2-amine can be prepared by following method as described in WO 2010/10933.

Intermediate-2

Preparation of 6-Chloro-1,3-dimethylpyrimidine-2,4(1H,3H)-dione

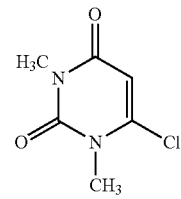

Method A:

To ice-cold solution of 1,3-dimethylbarbituric acid (50.0 g, 320.22 mmol) in water (20 ml), phosphorous oxychloride (200 ml) was drop wise added and the resulting mixture was refluxed for 3 h. The reaction mixture was cooled to 0° C. The reaction mixture was quenched with ice cold water (500 ml) and extracted with chloroform (2×500 ml). The combined organic extract was washed with water (2×200 ml), dried ($Na_2SO_4$) and concentrated to obtain the desired product (Yield: 90%); $^1H$ NMR (300 MHz, $CDCl_3$): δ 3.33 (s, 3H), 3.57 (s, 3H), 5.94 (s, 1H). APCI-MS (m/z) 175.26 $(M+H)^+$. IR (KBr): 3074.9, 2961.4, 1704, 1651, 1027, 755, 486 $cm^{-1}$. Melting point: 111-114° C. by DSC.

Method B:

To ice-cold solution of 1,3-dimethylbarbituric acid (1 Kg) in water (300 ml), phosphorous oxychloride (3.3 L) was drop wise added and the reaction mixture was refluxed for 3 h. After completion of reaction, the excess of phosphorous oxychloride was evaporated under reduced pressure. The reaction mixture was quenched using ice cold water under cooling. The mixture was extracted with dichloromethane (2×2.5 L). The combined organic extract was washed with saturated sodium bicarbonate solution (2.5 L), dried (anhydrous $Na_2SO_4$) and concentrated to obtain the product. The product was washed with ethanol (0.5 L) and dried to obtain 0.9 Kg of the title compound.

Intermediate-3

Preparation of 1,3-dimethyl-6-sulfanylpyrimidine-2,4(1H,3H)-dione

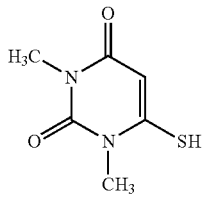

Method A:

A solution of sodium hydrosulphide hydrate (74.77 g, 1335.243 mmol) in water (125 ml) was added drop wise to a stirred solution of 6-chloro-1,3-dimethylpyrimidine-2,4 (1H,3H)-dione (50.0 g, 286.532 mmol) in a mixture of chloroform (250 ml) and ethanol (636 ml) at 0° C. and the resulting mixture was stirred at room temperature overnight. The reaction mixture was evaporated to dryness under vacuum. The residue obtained was dissolved in water (100 ml) and extracted with dichloromethane (2×100 ml). The aqueous layer was acidified with 1 N hydrochloric acid. The precipitated solid was collected by filtration, washed with water (2×100 ml) and dried to obtain the desired product (yield: 98%); $^1$H NMR (300 MHz, CDCl$_3$): δ 3.33 (s, 3H), 3.74 (s, 3H), 4.17 (s, 2H); APCI-MS (m/z) 171.33 (M−H)$^−$. IR (KBr): 3093, 2946, 1729, 1681, 1062, 1034, 754 cm$^{-1}$. Melting point: 130-134° C. (DSC).

Method B:

To a stirred solution of 6-chloro-1,3-dimethylpyrimidine-2,4(1H,3H)-dione (550.0 g, 3.16 mol) in absolute ethanol (5.5 L) was added portions wise sodium hydrosulphide hydrate (550.0 g 9.8 mol) at 0-5° C. over a period of 45 min. After complete addition, the reaction mixture was stirred at 25-30° C. for 1 to 2 h. The reaction mixture was filtered and washed with absolute ethanol (1.1 L). The filtrate was concentrated under vacuum to obtain residue which was then dissolved in water (2.75 L). The aqueous solution was washed with dichloromethane (2×2.2 L) followed by petroleum ether (1.1 L). The aqueous solution was acidified using hydrochloric acid (2.2 L) [equal portion of conc. hydrochloric acid and water (1:1)]. The precipitated solid was filtered and washed with water and dried to obtain the desired product (yield: 440 g, 86.2%).

Method C:

The stirred solution of solution of 6-chloro-1,3-dimethylpyrimidine-2,4(1H,3H)-dione (1 Kg) in ethanol (12 L) was added portion wise sodium hydrosulphide hydrate (1 kg) over a period of 1 h at 0 to 5° C. After addition, the reaction mixture was stirred at 25 to 30° C. for 2 h. The reaction mixture was filtered and washed with ethanol (2 L). The filtrate was collected and concentrated under vacuum to obtain residue which was then dissolved in water (8 L). The aqueous solution was washed with dichloromethane (3 L) followed by petroleum ether (2 L). The aqueous layer was separated and was acidified using hydrochloric acid solution [4 L, conc. hydrochloric acid and water (1:1)]. The precipitated solid was filtered and washed with water followed by ethanol and dried to obtain the 0.8 Kg of the title compound.

Intermediate-4

Preparation of ethyl 4-[(1,3-dimethyl-2,6-dioxo-1,2,3,6-tetrahydropyrimidin-4-yl) sulfanyl]-3-oxobutanoate

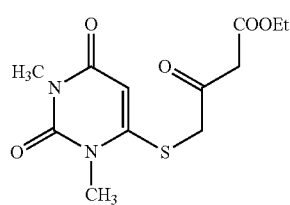

Method A:

To a stirred solution of 1,3-dimethyl-6-sulfanylpyrimidine-2,4(1H,3H)-dione (49 g, 284.883 mmol) in dry dichloromethane (60 ml) were added triethyl amine (43.23 g, 427.325 mmol) and ethyl 4-chloroacetoacetate (56.26 g, 341.860 mmol). The reaction mixture was stirred at room temperature for 2 h. The reaction mixture was diluted with water (800 ml) and extracted with chloroform (2×750 ml). The combined organic layer was washed with water (500 ml), dried over Na$_2$SO$_4$ and evaporated to give a product, which was crystallised from methanol (180 ml) and hexane (360 ml) to obtain product as a white solid (yield: 50%); $^1$H NMR (300 MHz, CDCl$_3$): δ 1.31 (t, J=7.5 Hz, 3H), 3.32 (s, 3H), 3.53 (s, 3H), 3.65 (s, 2H), 4.06 (s, 2H), 4.24 (q, J=7.2 Hz, 2H), 5.46 (s, 1H); APCI-MS (m/z) 301.03 (M+H)$^+$. IR (KBr): 2975, 1736, 1703, 1645, 1449, 1325, 1192, 1021 cm$^{-1}$. Melting point: 118-122° C. (DSC).

Method B:

The mixture of 1,3-dimethyl-6-sulfanylpyrimidine-2,4 (1H,3H)-dione (837 g, 0.011 mol) and 4-chloroethyl acetoacetate (1315 ml, 0.022 mol) in ethanol (6.6 L) was stirred at 25 to 30° C. for 36 h. The solid obtained was filtered and washed with ethanol (418 ml) to yield product as an off white solid (yield: 962 g, 66%).

Method C:

The mixture of 1,3-dimethyl-6-sulfanylpyrimidine-2,4 (1H,3H)-dione (1 Kg) and 4-chloroethyl acetoacetate (1.58 L) in ethanol (6.6 L) were stirred at 25 to 30° C. for 36-40 h. The product obtained was filtered and washed with ethanol (0.5 L) followed by petroleum ether (1 L) to get 1 Kg off white solid title compound.

Intermediate-5

Preparation of ethyl (1,3-dimethyl-2,4-dioxo-1,2,3,4-tetrahydrothieno[2,3-d]pyrimidin-5-yl)acetate

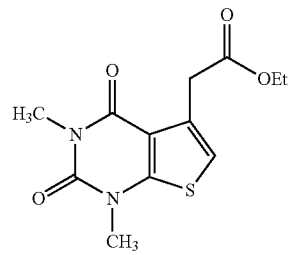 [SMILES: CCOC(=O)Cc1csc2c1c(=O)n(C)c(=O)n2C]

Method A:

A mixture of ethyl 4-[(1,3-dimethyl-2,6-dioxo-1,2,3,6-tetrahydropyrimidin-4-yl)sulfanyl]-3-oxobutanoate (450 g) and polyphosphoric acid (4 Kg) was stirred at 60-70° C. for 2 h. The reaction mixture was cooled to room temperature and carefully quenched with water (24 L). The mixture was extracted with ethyl acetate (2×2.25 L) and combined organic layer was washed with water (2×2.25 L). The mixture was dried over sodium sulphate and concentrated to obtain residue which was triturated with ethanol (450 ml) to afford product as an off-white solid (yield: 340 g, 80%). $^1$H NMR (300 MHz, CDCl$_3$): δ 1.26-1.31 (t, 3H), 3.39 (s, 3H), 3.55 (s, 3H), 3.93 (s, 2H), 4.16-4.23 (q, 2H), 6.70 (s, 1H), APCI-MS (m/z) 283.0 (M+H)$^+$. IR (KBr): 3114, 2986, 1722, 1697, 1657, 1495, 1201 cm$^{-1}$. Melting point: 159-160° C. (DSC).

Method B:

To a stirred solution of ethyl 4-[(1,3-dimethyl-2,6-dioxo-1,2,3,6-tetrahydropyrimidin-4-yl)sulfanyl]-3-oxobutanoate (42.10 g, 140.802 mmol) in dry toluene (420 ml) was added phosphorous pentoxide (29.97 g, 211.204 mmol) and the reaction mixture was heated at reflux temperature for 2 h. The reaction mixture was cooled to room temperature and quenched with water (400 ml). The mixture was extracted with ethyl acetate (2×400 ml) and the combined organic layer was washed with water (200 ml). The organic layer was dried (Na$_2$SO$_4$) and concentrated. The residue obtained after evaporation of the solvent was crystallised from methanol to afford the product as an off white solid (yield: 68%).

Method C:

To a stirred solution of ethyl 4-[(1,3-dimethyl-2,6-dioxo-1,2,3,6-tetrahydropyrimidin-4-yl)sulfanyl]-3-oxobutanoate (300 mg, 1.00 mmol) in dry toluene (10 ml) was added anhydrous zinc chloride (163 mg, 1.20 mmol) and the reaction mixture was heated to reflux for 2 h. The solvent was evaporated under reduced pressure and diluted with water (25 ml). The precipitated solid was collected by filtration, washed with water and dried to give the desired product as an off white solid (yield: 78%).

Method D:

To a stirred solution of ethyl 4-[(1,3-dimethyl-2,6-dioxo-1,2,3,6-tetrahydropyrimidin-4-yl)sulfanyl]-3-oxobutanoate (200 mg, 0.666 mmol) in dry toluene (5 ml) was added a drop of concentrated sulphuric acid at room temperature and the resulting mixture was refluxed for 1 h. The reaction mixture was cooled to room temperature and the solvent was evaporated. The residue obtained was diluted with water (25 ml). The precipitated solid was filtered, washed with water and dried to obtain the desired product as off white solid (yield: 33%).

Method E:

A mixture of ethyl 2-bromo-4-(2-ethoxy-2-oxoethyl)thiophene-3-carboxylate (1.5 g, 0.0046 mol, Intermediate-10), N,N'-dimethylurea (0.48 g, 0.0055 mol), Pd$_2$(dba)$_3$ (0.2 g, 4.2 mol %), xantphos (4,5-Bis(diphenylphosphino)-9,9-dimethylxanthene) (0.2 g, 6.5 mol %) and Cs$_2$CO$_3$ (4.0 g, 0.012 mol in dioxane (15 ml) was refluxed for 4 to 5 h. The reaction mixture was concentrated under vacuum and purified by column chromatography (20% Ethyl acetate in hexane) to obtain title compound as an off-white solid (0.4 g, 30%). $^1$H NMR (300 MHz, CDCl$_3$): δ 1.26-1.31 (t, 3H), 3.39 (s, 3H), 3.55 (s, 3H), 3.93 (s, 2H), 4.16-4.23 (q, 2H), 6.71 (s, 1H), APCI-MS (m/z) 283.0 (M+H)$^+$. IR (KBr): 3114, 2986, 1722, 1697, 1657, 1495, 1201 cm$^{-1}$. Melting point: 159-161° C.

Method F:

A mixture of ethyl 4-[(1,3-dimethyl-2,6-dioxo-1,2,3,6-tetrahydropyrimidin-4-yl)sulfanyl]-3-oxobutanoate (1 Kg) and polyphosphoric acid (8 Kg) were stirred at 60-70° C. for 2 h. The reaction mixture was cooled to room temperature and carefully quenched with water (40 L). The precipitated solid was filtered and washed with water (2 L). The precipitate was dissolved in dichloromethane (10 L), and the mixture was washed with water (2×3 L). The layers were separated, organic layer was dried over anhydrous sodium sulphate and treated with charcoal (10 g) and filtered. The filtrate was concentrated to give residue which was triturated with ethanol (0.5 L) to afford 0.7 Kg of title compound.

Intermediate-6

Preparation of (1,3-dimethyl-2,4-dioxo-1,2,3,4-tetrahydrothieno[2,3-d]pyrimidin-5-yl) acetic acid

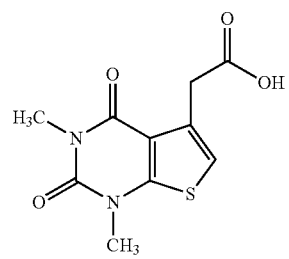 [SMILES: Cn1c(=O)c2c(CC(=O)O)csc2n(C)c1=O]

Method A:

A mixture of ethyl (1,3-dimethyl-2,4-dioxo-1,2,3,4-tetrahydrothieno[2,3-d]pyrimidin-5-yl)acetate (1.3 g, 4.850 mmol) and H$_2$SO$_4$ (6 N, 12 ml) in 1,4-dioxane (12 ml) was heated to reflux for 1 h. The reaction mixture was cooled to room temperature, diluted with water (50 ml) and extracted with ethyl acetate (2×50 ml). The combined organic layers were washed with water (50 ml), separated, dried over anhydrous sodium sulphate and concentrated under reduced pressure. The residue obtained was triturated with diethyl ether. The solid was filtered and washed with diethyl ether (10 ml) to obtain 450 mg of product (yield: 40%); $^1$H NMR (300 MHz, DMSO-d): δ 3.21 (s, 3H), 3.45 (s, 3H), 3.79 (s, 2H), 7.01 (s, 1H), 12.22 (br s, 1H).

Method B:

A solution of ethyl (1,3-dimethyl-2,4-dioxo-1,2,3,4-tetrahydrothieno[2,3-d]pyrimidin-5-yl)acetate (340.0 g, 1.20 mol) in 1,4-dioxane (1700 ml) was stirred for 30 min at room temperature, followed by addition of sulfuric acid (3 N, 133 ml in 1700 ml water). The reaction mixture was refluxed for 3 to 4 h and concentrated under vacuum to get an oily mass. It was diluted with water (1700 ml) and stirred for 30 min at 25 to 30° C. to obtain the product as a light brown solid which was further washed with water. The product was dried well and further stirred in dichloromethane (1220 ml). The solid was filtered, washed with dichloromethane (680 ml) and dried to yield the title compound (yield: 244 g, 80%).

Method C:

To the solution of ethyl (1,3-dimethyl-2,4-dioxo-1,2,3,4-tetrahydrothieno[2,3-d]pyrimidin-5-yl)acetate (1 Kg) in 1,4-dioxane (5 L) was stirred for 30 min at room temperature, followed by addition of sulfuric acid (3 N, 0.4 L in 5 L water). The reaction mixture was heated at 80-90° C. for 3 to 4 h. To the reaction mixture, water (10 L) was added and cooled to 25-30° C. The crude solid product was filtered and washed with water (2×1 L). The product was dried well and further stirred in dichloromethane (4 L). The solid was filtered, washed with dichloromethane (1 L) and dried to afford 0.6 Kg of the title compound.

Intermediate-7

Preparation of N-{4-[2,4-Difluoro-3-(trifluoromethyl)phenyl]-1,3-thiazol-2-yl}-4-[(1,3-dimethyl-2,6-dioxo-1,2,3,6-tetrahydropyrimidin-4-yl)thio]-3-oxobutanamide

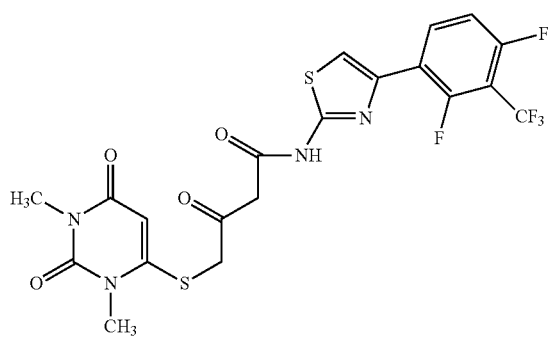 [SMILES: Cn1c(SCC(=O)CC(=O)Nc2nc(-c3ccc(F)c(C(F)(F)F)c3F)cs2)cc(=O)n(C)c1=O]

To a stirred solution of 4-[2,4-difluoro-3-(trifluoromethyl)phenyl]-1,3-thiazol-2-amine (224 mg, 0.801 mmol) in dry toluene (6 ml) was added sodium hydride (60% dispersion in mineral oil, 48 mg, 1.214 mmol) and the reaction mixture was stirred at room temperature for 30 min. Ethyl 4-[(1,3-dimethyl-2,6-dioxo-1,2,3,6-tetrahydropyrimidin-4-yl)sulfanyl]-3-oxobutanoate (200 mg, 0.607 mmol) was added to the above reaction mixture, and the resulting mixture was heated to reflux for 24 h. The reaction mixture was cooled to room temperature, diluted with water and extracted with ethyl acetate (3×50 ml). The combined organic layers were washed with brine and dried over Na$_2$SO$_4$. The filtrate was concentrated under reduced pressure. The crude residue thus obtained was purified by silica gel column chromatography using 2% methanol in chloroform to obtain the product as a white solid (yield: 25%); $^1$H NMR (300 MHz, CDCl$_3$): δ 3.14 (s, 3H), 3.41 (s, 3H), 3.95 (s, 2H), 4.43 (s, 2H), 5.60 (s, 1H), 7.53 (t, J=9.0 Hz, 1H), 7.67 (s, 1H), 8.25-8.35 (m, 1H), 12.51 (br s, 1H).

Intermediate-8

Preparation of 5-[2-(1H-Benzotriazol-1-yl)-2-oxoethyl]-1,3-dimethylthieno[2,3-d]pyrimidine-2,4(1H,3H)-dione

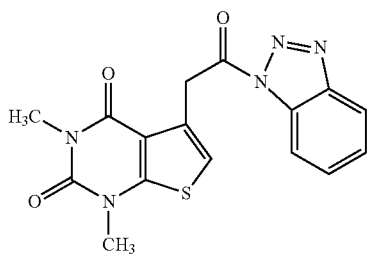 [SMILES: Cn1c(=O)c2c(CC(=O)n3nnc4ccccc43)csc2n(C)c1=O]

To a stirred solution of benzotriazole (563 mg, 4.724 mmol) in dry dichloromethane (15 ml) was added thionyl chloride (140 mg, 92 μl, 1.181 mmol) and the reaction mixture was stirred at room temperature for 30 min. To the reaction mixture was added (1,3-dimethyl-2,4-dioxo-1,2,3,4-tetrahydrothieno[2,3-d]pyrimidin-5-yl) acetic acid (300 mg, 1.181 mmol) and the resulting mixture was stirred at room temperature for 2 h. The solvent was distilled off under reduced pressure. The residue obtained after the evaporation of the solvent was purified by silica gel column chromatography using 10% ethyl acetate in chloroform to obtain 520 mg of the product as an off white solid; $^1$H NMR (300 MHz, CDCl$_3$): δ 3.33 (s, 3H), 3.59 (s, 3H), 5.04 (s, 2H), 6.84 (s, 1H), 7.52 (t, J=7.8 Hz, 1H), 7.65 (t, J=7.2 Hz, 1H), 8.15 (d, J=8.4 Hz, 1H), 8.24 (d, J=8.1 Hz, 1H).

Intermediate-9

Preparation of 2-Amino-4-ethoxycarbonylmethyl-thiophene-3-carboxylicacid ethylester

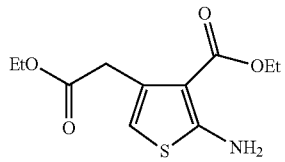 [SMILES: CCOC(=O)Cc1csc(N)c1C(=O)OCC]

To a stirred solution of ethyl-4-bromoacetoacetate (275 g, 1.31 mol), ethylcyanoacetate (150 ml, 1.33 mol) in ethanol (3.5 L) was added Na$_2$S.9H$_2$O (330 g, 4.23 mol) followed by drop wise addition of triethylamine (210 ml, 1.5 mmol) and the resulting mixture was stirred at 40-45° C. for 36 h. The reaction mixture was diluted with water and extracted with ethyl acetate. The organic phase was separated, dried over Na$_2$SO$_4$ and the solvent was distilled off under vacuum. The residue was purified by column chromatography (n-hexane:ethyl acetate 4:1) to give the title compound. (36 g, 12%). $^1$H NMR (300 MHz, CDCl$_3$): δ 1.27 (m, 6H), 3.68 (s, 2H), 4.19 (m, 4H), 6.00 (s, 1H), 6.18 (br, 2H); APCI-MS (m/z) 257.96 (M+H)$^+$. IR (KBr): 3415.8, 3315.7, 2981, 1733, 1657, 1604, 1489, 1479, 1272, 1174, 1071, 1028, 707.8 cm$^{-1}$. Melting point: 71° C.

Intermediate-10

Preparation of Ethyl 2-bromo-4-(2-ethoxy-2-oxo-ethyl)thiophene-3-carboxylate

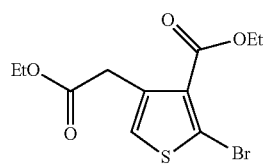 [SMILES: CCOC(=O)Cc1csc(Br)c1C(=O)OCC]

Anhydrous copper (II) bromide (7 g, 0.031 mol) and tertiary-butyl nitrite (6 g, 0.058 mol) in acetonitrile were added to a solution of 2-amino-4-ethoxycarbonylmethyl-thiophene-3-carboxylicacid ethylester (10 g, 0.038 mol) in acetonitrile at 25 to 30° C. and the resulting mixture was stirred at 60-65° C. for 1 to 2 h. After gas evolution was completed the reaction mixture was allowed to cool to room temperature and poured into 10% aqueous hydrochloric acid solution. The reaction mixture was extracted with diethyl ether. The ether layer was concentrated and purified by column chromatography (25% ethyl acetate in hexane) to give the desired product as oil (3.1 g, 24%). $^1$H NMR (300 MHz, DMSOd$_6$): δ 1.15-1.19 (t, 3H), 1.26-1.30 (t, 3H), 3.84 (s, 2H), 4.04-4.10 (q, 2H), 4.18-4.25 (q, 2H), 7.50 (s, 1H), APCI-MS (m/z) 322.90 (M+H)$^+$. IR (KBr): 3434, 2927, 1643, 1537, 1028, 747 cm$^{-1}$ Example-1

Preparation of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide

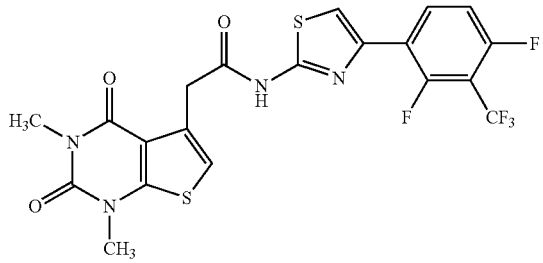 [SMILES: Cn1c(=O)c2c(CC(=O)Nc3nc(-c4ccc(F)c(C(F)(F)F)c4F)cs3)csc2n(C)c1=O]

Method A:

A solution of 4-[2,4-difluoro-3-(trifluoromethyl)phenyl]-1,3-thiazol-2-amine (38.66 g, 0.138 mol) in dichloromethane (154 ml) was added to a solution of (1,3-dimethyl-2,4-dioxo-1,2,3,4-tetrahydrothieno[2,3-d]pyrimidin-5-yl) acetic acid (29.0 g, 0.114 mol) in dichloromethane (174 ml) at 0° C. and the resulting mixture was stirred for 5 min. To the above mixture was added 1-hydroxybenzotriazole (HOBt) (5.80 g, 0.0429 mol) followed by N-methyl morpholine (13.53 g, 0.133 moles) and the reaction mixture was stirred for 30 min. (1-(3-dimethylaminopropyl)-3-ethylcarbodiimide) (25.90 g, 0.135 mol) was added to it and the reaction mixture was stirred at 0° C. for 3 h. The reaction mixture was allowed to warm to 25 to 30° C. and stirred for 22 to 24 h. The precipitated solid was filtered and washed with dichloromethane. It was further purified by dissolving it in DMSO (1000 ml) at 60 to 65° C. and filtered through celite bed. To the filtered solution demineralised water (3.5 L) was added. The resultant precipitated product was filtered on Buchner funnel at 25 to 30° C. and washed with water. The solid was unloaded and dried. (yield: 47 g, 65%). $^1$H NMR (300 MHz, DMSO d$_6$): δ 3.19 (s, 3H), 3.46 (s, 3H), 4.07 (s, 2H), 7.07 (s, 1H), 7.48-7.54 (t, J=9.0 Hz, 1H), 7.61 (s, 1H), 8.30-8.37 (q, J=7.8 Hz, 1H), 12.48 (br s, 1H); ESI-MS (m/z): 517.09 (M+H)$^+$. IR (KBr): 3218, 3101, 1699, 1642, 1626, 1561, 1480, 1307, 1128, 1019, 743 cm$^{-1}$. Melting point: 274° C.
Method B:

To a stirred solution of 4-[2,4-difluoro-3-(trifluoromethyl) phenyl]-1,3-thiazol-2-amine (11.9 g, 42.553 mmol) in dry toluene (350 ml) was added sodium hydride (60% dispersion in mineral oil, 1.02 g, 42.553 mmol) and the reaction mixture was stirred for 30 min at room temperature. Ethyl (1,3-dimethyl-2,4-dioxo-1,2,3,4-tetrahydrothieno[2,3-d]pyrimidin-5-yl)acetate (10.0 g, 35.460 mmol) was added to the above reaction mixture and refluxed for 24 h. The reaction mixture was cooled to room temperature and another portion of sodium hydride (60% dispersion in mineral oil, (1.02 g, 42.553 mmol) was added and it was further refluxed for 24 h. The solvent was evaporated under reduced pressure and quenched using HCl (1 N, 150 ml). The precipitated solid was collected by filtration and recrystallised from isopropyl alcohol to give the product as a white solid (yield: 90%).
Method C:

To a stirred solution of N-{4-[2,4-difluoro-3-(trifluoromethyl)phenyl]-1,3-thiazol-2-yl}-4-[(1,3-dimethyl-2,6-dioxo-1,2,3,6-tetrahydropyrimidin-4-yl)thio]-3-oxobutanamide (85 mg, 0.159 mmol) in dry toluene (1.5 ml) was added phosphorous pentoxide (34 mg, 0.238 mmol) at room temperature and the resulting mixture was refluxed for 2 h. The reaction mixture was cooled to room temperature and quenched with water (15 ml). The mixture was extracted with ethyl acetate (2×15 ml) and the combined organic extract was washed with water (10 ml). The organic layer was dried over Na$_2$SO$_4$ and concentrated under reduced pressure. The residue obtained after evaporation of the solvent was purified by silica gel column chromatography using 10% ethyl acetate in chloroform to afford the product as an off white solid (yield: 65%);
Method D:

To a stirred solution of 4-[2,4-difluoro-3-(trifluoromethyl) phenyl]-1,3-thiazol-2-amine (118 mg, 0.422 mmol) in dry THF (15 ml), sodium hydride (60% dispersion in mineral oil, (12.17 mg, 0.507 mmol) was added and the reaction mixture was stirred for 30 min at room temperature. 5-[2-(1H-Benzotriazol-1-yl)-2-oxoethyl]-1,3-dimethylthieno[2,3-d]pyrimidine-2,4(1H,3H)-dione (150 mg, 0.422 mmol) was added to the above reaction mixture and it was refluxed for 24 h. The solvent was removed under reduced pressure and quenched with HCl (1 N, 10 ml). The precipitated solid was collected by filtration. The solid was recrystallised from isopropyl alcohol to give the product as a white solid (yield: 15%).
Method E:

To a stirred solution of (1,3-dimethyl-2,4-dioxo-1,2,3,4-tetrahydrothieno[2,3-d]pyrimidin-5-yl) acetic acid (100 mg, 0.393 mmol) in 1,2-dichloroethane (4 ml) was added EDCI (90 mg, 0.471 mmol), HOBt (16 mg, 0.117 mmol) and 4-dimethylaminopyridine (5 mg, 0.039 mmol). The mixture was then stirred at room temperature for 10-15 min. 4-[2, 4-Difluoro-3-(trifluoromethyl)phenyl]-1,3-thiazol-2-amine (110 mg, 0.393 mmol) was then added to the reaction mixture and it was stirred at the room temperature for 48 h. The solvent was evaporated under reduced pressure and the residue obtained was diluted with methanol (15 ml). The mixture was stirred at room temperature for 30 min. The solid precipitated was collected by filtration. The solid product was further purified by recrystallization from isopropanol to give the desired product.
Method F:

To a stirred solution of (1,3-dimethyl-2,4-dioxo-1,2,3,4-tetrahydrothieno[2,3-d]pyrimidin-5-yl) acetic acid (1 Kg) in dichloromethane (6 L), solution of 4-[2,4-difluoro-3-(trifluoromethyl)phenyl]-1,3-thiazol-2-amine (1.33 Kg) in dichloromethane (4 L) was added at 0-5° C. and the mixture was stirred for 5 min. To the reaction mixture HOBt (0.2 kg) and N-methyl morpholine (0.46 kg) were added and the reaction mixture was stirred for 30 min. To the reaction mixture (1-(3-dimethylaminopropyl)-3-ethylcarbodiimide).hydrochloride (EDCI.HCl) (0.89 Kg) was added and the reaction mixture was stirred for 3 h at 0-5° C. The reaction mixture was allowed to warm to 25 to 30° C. and stirred for 36-40 h. The precipitated solid was filtered and washed with dichloromethane. To the crude solid was added DMSO (29 L) and it was stirred at 50 to 60° C. until clear solution was observed. The solution was filtered through celite bed and to the filtrate, water (75 L) was added. The precipitated product was filtered, washed with water and dried to obtain 1.0 Kg of the title compound.

Example-2

Preparation of Form X of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide

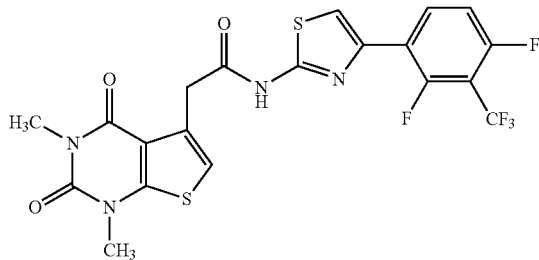 [SMILES: Cn1c(=O)c2c(CC(=O)Nc3nc(-c4ccc(F)c(C(F)(F)F)c4F)cs3)csc2n(C)c1=O]

To a stirred solution of (1,3-dimethyl-2,4-dioxo-1,2,3,4-tetrahydrothieno[2,3-d]pyrimidin-5-yl) acetic acid (0.5 g, 1.9 mmol) in 1,2-dichloroethane (20 ml) was added EDCI (0.43 g, 2.2 mmol), HOBt (0.07 g, 0.5 mmol) and 4-dimethylaminopyridine (0.02 g, 0.1 mmol). The reaction mixture was stirred at room temperature for 10-15 min. 4-[2,4-Difluoro-3-(trifluoromethyl)phenyl]-1,3-thiazol-2-amine (0.55 g, 1.9 mmol) was added and the reaction mixture was stirred at room temperature for 48 h. The solvent was evaporated under reduced pressure and the residue obtained was diluted with methanol (20 ml). The reaction mixture was stirred at room temperature for 30 min. The solid separated out was collected by filtration. It was washed with methanol and dried to obtain 0.240 g of Form X of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide.

Example-3

Preparation of Form Y of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide To a solution of (1,3-dimethyl-2,4-dioxo-1,2,3,4-tetrahydrothieno[2,3-d]pyrimidin-5-yl) acetic acid (300 g, 1.181 mol) in dichloromethane (1.8 L), a solution of 4-[2,4-difluoro-3-(trifluoromethyl)phenyl]-1,3-thiazol-2-amine (400.5 g, 1.430 mol) in dichloromethane (1.2 L) was added at 0-5° C. The reaction mixture was stirred for 5 min. To the reaction mixture HOBt (60 gm, 0.44 mol) and N-methyl morpholine (139.94 g, 1.36 mol) were added and the reaction mixture was stirred for 30 min. To the reaction mixture, (1-(3-dimethylaminopropyl)-3-ethylcarbodiimide).hydrochloride (EDCI.HCl) (267.91 gm, 1.39 mol) was added and it was stirred for 3 h at 0-5° C. The reaction mixture was allowed to warm to 25 to 30° C. and stirred for 36-40 h. The precipitated solid was filtered and washed with dichloromethane. The solid obtained was dried to obtain 385 g of Form Y of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide.

Example-4

Preparation of Form Z of N-{4-[2,4-difluoro-3-(trifluoromethyl)phenyl]-1,3-thiazol-2-yl})-2-(1,3-dimethyl-2,4-dioxo-1,2,3,4-tetrahydrothieno[2,3-d]pyrimidin-5-yl)acetamide A solid obtained in example 2 was dissolved in DMSO (7.3 L) and it was stirred at 50 to 60° C. to get a clear solution. Charcoal (3.6 g) was added to the solution and it was stirred. The solution was filtered through celite bed. To the filtrate, water (15 L) was added and it was stirred. The precipitated solid was filtered, washed with water and dried to obtain 365 g of Form Z of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide.

Example-5

Preparation of crystalline potassium salt of [N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide] designated as Form I To a stirred solution of N-{4-[2,4-Difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide (1.0 g; 1.93 mmol) in absolute ethanol (7.0 ml) and n-pentane (25 ml) was drop wise added freshly prepared potassium tert-butoxide in ethanol (0.228 g of potassium tert-butoxide in 3.0 ml of ethanol) under nitrogen atmosphere at −5.0 to 0° C. and the resulting mixture was stirred at same temperature for 1.0 h. n-Pentane (5.0 ml) was added and the reaction mixture was maintained for 1-2 h at room temperature. The solid obtained was filtered and dried for 3 to 4 h at 30 to 35° C. under vacuum. The dried solid was stirred in acetonitrile (10 ml) for 1 to 2 h. The solid was collected on Buchner funnel and washed with acetonitrile (2 ml). The solid was dried for 8 to 10 h at 30 to 35° C. under vacuum. $^1$H NMR (300 Hz, DMSO-$d_6$): 8.373-8.452 (m, 1H); 7.338-7.403 (t, 1H); 7.037-7.048 (d, J=3.3, 1H); 6.903 (s, 1H); 3.827 (s, 2H); 3.465 (s, 3H); 3.235 (s, 3H). APCI-MS (m/z): 517.02 (M+H)$^+$. Yield: 89.89%.

Example-6

Preparation of crystalline potassium salt of [N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide] designated as Form II To a stirred solution of crystalline N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl) acetamide (1.0 g (1.93 mmol) in n-pentane (25.0 ml) was added t-butanol (6.0 ml) at −5.0 to 0° C. under nitrogen atmosphere and the resulting mixture was stirred for 10 min. To this reaction mixture was drop wise added freshly prepared solution of potassium t-butoxide solution in t-butanol (0.239 g of potassium t-butoxide in 2.0 ml of t-butanol) at −5 to 0° C. and it was stirred at same temperature for 1 h. The solid obtained was filtered and washed with 5.0 ml of n-Pentane. The solid was dried for 3-4 h at 30-35° C. under vacuum. The dried solid was charged in a flask followed by the addition of 10 ml acetonitrile. The reaction mixture was stirred for 1-2 h. The solid was filtered and washed with 1.0 ml of acetonitrile and dried for 8-10 h at 30-35° C. under vacuum. Yield: 0.9 g, 90%.

Example-7

Preparation of amorphous potassium salt of [N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide]

N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide potassium salt (1 g) was heated to 300-320° C. on heating mental to melt the compound under reduced pressure. It was then cooled to room temperature to obtain 0.8 g of the amorphous form.

Example-8

Preparation of crystalline sodium salt of [N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide]designated as Form A N-{4-[2,4-Difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide (1.0 g 1.93 mmol) was taken into a flask followed by addition of absolute ethanol (15.0 ml) under nitrogen atmosphere. The reaction mass was cooled to −5.0 to 0° C. and it was further maintained for 10 min. In a separate flask ~3.0% sodium methoxide solution in ethanol (0.157 g of sodium methoxide in 5.0 ml of ethanol) was prepared. The sodium methoxide solution was added slowly into reaction mass at −5 to 0° C. and it was maintained for 1 h. The solvent was distilled off at 30 to 35° C. to get solid. The solid was dried for 1 to 2 h at 30-35° C. under vacuum. The dried solid was stirred in acetonitrile (10 ml) for 1-2 h at room temperature. The solid was collected on Buchner funnel and dried for 3 to 4 h at 30 to 35° C. under vacuum. $^1$H NMR (300 Hz, DMSO-$d_6$): 8.382 (m, 1H); 7.458-7.393 (t, 1H); 7.273-7.263 (d, J=3.0, 1H); 6.96 (s, 1H); 3.937 (s, 2H); 3.461 (s, 3H); 3.214 (s, 3H). APCI-MS (m/z): 517.02 (M+H)$^+$. Yield: 86.37%.

Example-9

Preparation of [N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide]sodium in amorphous form N-{4-[2,4-Difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide (1 g 1.93 mmol) was taken into a flask followed by addition of absolute ethanol (20 ml) under nitrogen atmosphere. The reaction mixture was cooled to −5 to 0° C. and further maintained for 10 min. In a separate flask ~4% sodium tert-butoxide solution in ethanol (0.195 g of sodium tert-butoxide in 5 ml of ethanol) was prepared. The sodium tert-butoxide solution was slowly added into the reaction mass at −5 to 0° C. and maintained for 1 h. The solvent was distilled off completely at 30 to 35° C. under vacuum till to get solid. The solid was dried for 1 to 2 h at 30 to 35° C. under vacuum. $^1$H NMR (300 Hz, DMSO-$d_6$): 8.37-8.45 (m, 1H); 7.37-7.43 (t, 1H); 7.09-7.08 (d, J=3.0 Hz, 1H); 6.90 (s, 1H); 3.83 (s, 2H); 3.46 (s, 3H); 3.23 (s, 3H). APCI-MS (m/z): 517.02 (M+H)$^+$. Yield: 91.40%.

Example-10

Preparation of crystalline lithium salt of [N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide]designated as Alpha N-{4-[2,4-Difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide (1 g; 1.93 mmol) was taken into a flask followed by the addition of absolute ethanol (20 ml) under nitrogen atmosphere. The reaction mixture was cooled to −5 to 0° C. and maintained for 10 min. Lithium hydroxide monohydrate (0.122 g; 2.90 mmol) was slowly added in portion wise to the reaction mixture at −5 to 0° C. and further maintained for 1 h. The solvent was distilled off completely at 30 to 35° C. under vacuum to get solid. The solid was dried for 1 to 2 h at 30-35° C. under vacuum. The solid was stirred in diethyl ether (15 ml) for 1 to 2 h, collected on Buchner funnel and washed with diethyl ether (15 ml). The solid was dried for 1 to 2 h at 30 to 35° C. under vacuum. $^1$H NMR (300 Hz, DMSO-$d_6$): 8.42-8.36 (m, 1H); 7.36-7.43 (t, 1H); 7.03-7.04 (d, J=3.3 Hz, 1H); 6.89 (s, 1H); 3.81 (s, 2H); 3.42 (s, 3H); 3.23 (s, 3H). APCI-MS (m/z): 517.02 (M+H)$^+$. Yield: 90%.

Example-11

Solubility Studies of Compound of Formula (II) and its Sodium and Potassium Salt I. Methodology:
   Shake flask method was used to determine the solubility of compound in various bio-relevant media of different pH and quantification is done using HPLC method.
II. Experimental:
   Following bio-relevant media and water were selected to study the solubility behaviour.
   i. FaSSIF (Fasted state simulated intestinal fluid) of pH 6.5
   ii. FeSSIF (Fed state simulated intestinal fluid) of pH 5.0
   iii. Water.
   Procedure: Test substance (1 mg) was taken in a test tube and medium [FaSSIF (pH 6.5) or FeSSIF (pH 5.0) or water] was added in the increment of 1 ml with shaking. After completion of addition of 10 ml of media, test tubes containing sample solution were put on a mechanical shaker set at 37° C. and 200 rpm for shaking up to about 15 minutes. After shaking, the content of each flask, it was filtered through 0.45 µl filter. The filtered solution was analysed using HPLC for quantification. A sample solution of 1 mg in 10 ml of DMSO was used as reference standard for quantifying dissolved test substance in each media. The solubility in each media is expressed as µg/ml (Table-10).

TABLE-10

Solubility data for compound (II) and its Sodium and Potassium salt

| Buffers | Compound (II) (Conc. in µg/ml) | Sodium salt of compound (II) (Conc. in µg/ml) | Potassium salt of compound (II) (Conc. in µg/ml) |
|---|---|---|---|
| FaSSIF (pH 6.5) | 0.16 | 1.07 | 5.91 |
| FeSSIF (pH 5.0) | 0.06 | 0.24 | 5.53 |
| Water | 0.1 | 0.13 | 0.49 |

Example-12

Stability Studies of Salts of Compound of Formula II

The salts of the compound of formula II were stored under conditions as shown in below table and a total amount of degradation products (related substances) as well as single maximum impurity formed during storage was estimated by HPLC. The material was packed in inner clear polythene bag under nitrogen lined with black polythene bag, covered with triple laminated aluminium bag placed in HDPE drum and subjected to the conditions mentioned in the table 11.

TABLE 11

| Storage conditions | Condition 1 | Condition 2 | Condition 3 |
|---|---|---|---|
| temperature | 25 ± 2° C. | 30 ± 2° C. | 40 ± 2° C. |
| Humidity (% RH) | 60 ± 5% RH | 65 ± 5% RH | 75 ± 5% RH |
| Testing intervals | 0, 1, 2, 3, 6, 9 months | 0, 1, 2, 3, 6 months | 0, 1, 2, 3, 6 months |

Stability of salts of compound of formula II under the storage condition 1:

TABLE 12

| Salts | Test Item (%) | Storage period (months) | | | | | |
|---|---|---|---|---|---|---|---|
| | | 0 | 1 | 2 | 3 | 6 | 9 |
| Potassium | Related substances | 0.44 | 0.45 | 0.31 | 0.43 | 0.35 | 0.35 |
| | single max. impurity | 0.26 | 0.27 | 0.19 | 0.26 | 0.21 | 0.21 |
| Sodium | Related substances | 0.22 | 0.28 | 0.36 | 0.38 | 0.51 | 0.75 |
| | single max. impurity | 0.05 | 0.06 | 0.10 | 0.11 | 0.23 | 0.39 |

Stability of salts of compound of formula II under the storage condition 2:

TABLE 13

| Salts | Test Item (%) | Storage period (months) | | | | |
|---|---|---|---|---|---|---|
| | | 0 | 1 | 2 | 3 | 6 |
| Potassium | Related substances | 0.44 | NT | NT | NT | 0.51 |
| | single max. impurity | 0.26 | NT | NT | NT | 0.31 |
| Sodium | Related substances | 0.22 | 0.30 | 0.40 | 0.47 | 0.71 |
| | single max. impurity | 0.05 | 0.05 | 0.14 | 0.18 | 0.35 |

NT: not tested

Stability of salts of compound of formula II under the storage condition 3:

TABLE 14

| Salts | Test Item (%) | Storage period (months) | | | | |
|---|---|---|---|---|---|---|
| | | 0 | 1 | 2 | 3 | 6 |
| Potassium | Related substances | 0.44 | 0.44 | 0.32 | 0.46 | 0.52 |
| | single max. impurity | 0.26 | 0.27 | 0.20 | 0.28 | 0.32 |
| Sodium | Related substances | 0.22 | 0.54 | 0.70 | 0.77 | 1.0 |
| | single max. impurity | 0.05 | 0.22 | 0.36 | 0.39 | 0.58 |

Example-13

Dissolution Studies of Compound of Formula (II), Sodium Salt of Compound of Formula (II) and Potassium Salt of Compound of Formula (II)

Suspension of compound of formula (II) and its salts with same composition was prepared using conventional homogenization technique. The % drug release was determined by comparing with 10 mg equivalent suspension (after sonication).

TABLE-15

Dissolution studies of Compound of formula (II), its sodium salt and potassium salt in suspension form

| Sr. No | Composition | Batch No | | |
|---|---|---|---|---|
| | | 1A Compound (II) | 2A Sodium salt of Compound of formula (II) | 3A Potassium salt of Compound of formula (II) |
| 1 | Active Ingredient | 10 mg | 10 mg | 10 mg |
| 2 | Kollidon VA 64 | 40 mg | 40 mg | 40 mg |
| 3 | Sodium lauryl sulphate (SLS) | 20 mg | 20 mg | 20 mg |
| 4 | Purified water | q.s. | q.s. | q.s. |
| | % drug release after 15 minutes | 0.40 | 1.2 | 6.3 |

What is claimed is:

1. Potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide represented by the formula (II)

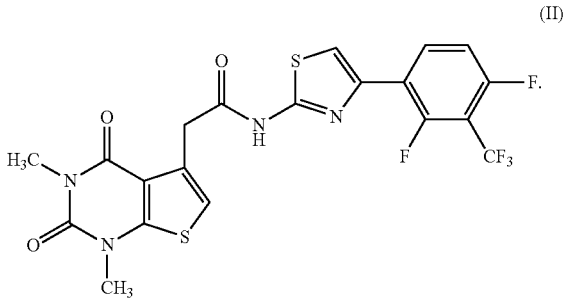 [SMILES: Cn1c(=O)c2c(CC(=O)Nc3nc(-c4ccc(F)c(C(F)(F)F)c4F)cs3)csc2n(C)c1=O]

2. Potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide represented by the formula (II)

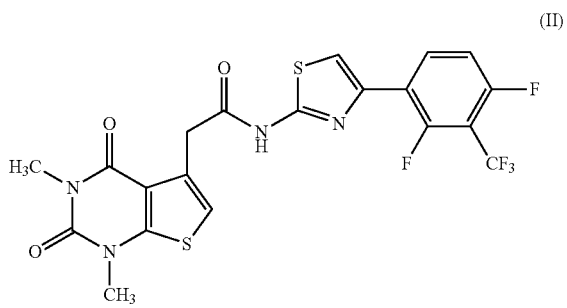 [SMILES: Cn1c(=O)c2c(CC(=O)Nc3nc(-c4ccc(F)c(C(F)(F)F)c4F)cs3)csc2n(C)c1=O]

in crystalline form.

3. The crystalline potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide according to claim 2, which is designated as Form I, characterised by the X-ray Powder Diffraction (XRPD) pattern as provided in FIG. 1.

4. The crystalline potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide according to claim 2, which is designated as Form I, characterised by the X-ray Powder Diffraction (XRPD) pattern comprising one or more of the following peaks expressed in terms of 2θ: 15.93, 20.61, 23.63, 24.47 and 25.08±0.2.

5. The crystalline potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide according to claim 2, which is designated as Form I, characterised by the X-ray Powder Diffraction (XRPD) pattern comprising one or more of the following peaks expressed in terms of 2θ: 23.63 and 24.47±0.2.

6. The crystalline potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide according to claim 2, which is designated as Form II, characterised by the X-ray Powder Diffraction (XRPD) pattern as provided in FIG. 3.

7. The crystalline potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide according to claim 2, which is designated as Form II, characterised by the X-ray Powder Diffraction (XRPD) pattern comprising one or more of the following peaks expressed in terms of 2θ: 12.07, 12.39, 20.98, 24.01 and 25.69±0.2.

8. The crystalline potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide according to claim 2, which is designated as Form II, characterised by the X-ray Powder Diffraction (XRPD) pattern comprising one or more of the following peaks expressed in terms of 2θ: 24.01 and 25.69±0.2.

9. The potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide according to claim 1 is in Amorphous form.

10. The amorphous form of potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide according to claim 9, characterised by the X-ray Powder Diffraction (XRPD) pattern as provided in FIG. 5.

11. The potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide according to claim 1, having water content less than about 5%.

12. The potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide according to claim 1, wherein 10% of the particles ($D_{10}$) have size in the range from about 0.3 μm to about 10 μm.

13. The potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide according to claim 1, wherein 10% of the particles ($D_{10}$) have size in the range 0.5 μm to about 5 μm.

14. The potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide according to claim 1, wherein 90% of the particles ($D_{90}$) have size in the range from about 4 μm to about 300 μm.

15. The potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide according to claim 1, wherein 90% of the particles ($D_{90}$) have size in the range from about 5 μm to about 150 μm.

16. The potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide according to claim 1 having average particle size ($D_{50}$) in the range from about 1 μm to about 100.

17. The potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide according to claim 1 having average particle size ($D_{50}$) in the range from about 1 μm to about 20 μm.

18. A process for the preparation of crystalline potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as Form I, which process comprises the following steps:
(a) taking N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide in a mixture of ethanol and n-pentane;

(b) adding ethanolic solution of potassium tertiary butoxide or potassium ethoxide to the solution or suspension of step (a) or adding the solution or suspension of step (a) to ethanolic solution of potassium tertiary butoxide or potassium ethoxide; and (c) isolating the desired potassium salt.

19. A process for the preparation of crystalline potassium salt of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as Form II, which process comprises the following steps:

(a) taking N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide in a mixture of tertiary butanol and n-pentane;

(b) adding potassium tertiary butoxide in tertiary butanol to the solution or suspension of step (a) or adding the solution or suspension of step (a) to potassium tertiary butoxide in tertiary butanol; and (c) isolating the desired potassium salt.

20. Crystalline N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as Form Y characterised by the X-ray Powder Diffraction (XRPD) pattern as provided in FIG. 14.

21. The crystalline N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as Form Y according to claim 20, characterised by the X-ray Powder Diffraction (XRPD) pattern comprising one or more of the following peaks expressed in terms of 2θ: 4.72, 9.40, 21.04, 25.87 and 31.73±0.2.

22. Crystalline N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as Form Y characterised by the Fourier Transform Infrared Spectroscopy (FT-IR) pattern wherein the ratio between the intensity of the absorption bands at wavelengths 1500 cm$^{-1}$ and 1480 cm$^{-1}$ is from 1:1.7 to 1:2.4.

23. Crystalline N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as Form Z characterised by the X-ray Powder Diffraction (XRPD) pattern as provided in FIG. 16.

24. The crystalline N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as Form Z according to claim 23, characterised by the X-ray Powder Diffraction (XRPD) pattern comprising one or more of the following peaks expressed in terms of 2θ: 10.63, 19.25, 22.11, 22.76 and 27.27±0.2.

25. Crystalline N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide designated as Form Z characterised by the Fourier Transform Infrared (FT-IR) Spectroscopy pattern wherein the ratio between the intensity of the absorption bands at wavelengths 1500 cm$^{-1}$ and 1480 cm$^{-1}$ is from 1:2.5 to 1:2.9.

26. A process for the preparation of N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide or pharmaceutically acceptable salt thereof, which process comprises the steps of (a) treating dimethylbarbituric acid with a suitable chlorinating agent to afford 6-chloro-1,3-dimethyluracil of formula (1);

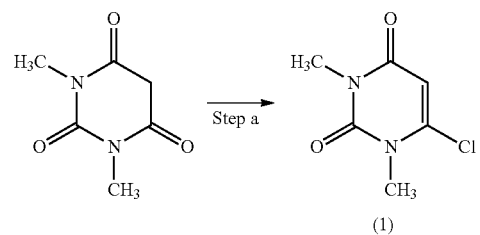

(b) treating 6-chloro-1,3-dimethyluracil of formula (1) with sodium hydrosulphide hydrate to give 6-mercapto-1,3-dimethyluracil of the formula (2);

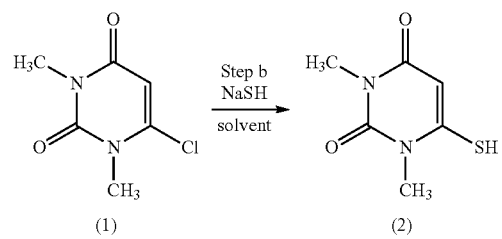

(c) treating 6-mercapto-1,3-dimethyluracil of the formula (2) with the compound of formula (3) wherein R is (C$_1$-C$_4$)alkyl, to give ester compound of formula (4); and

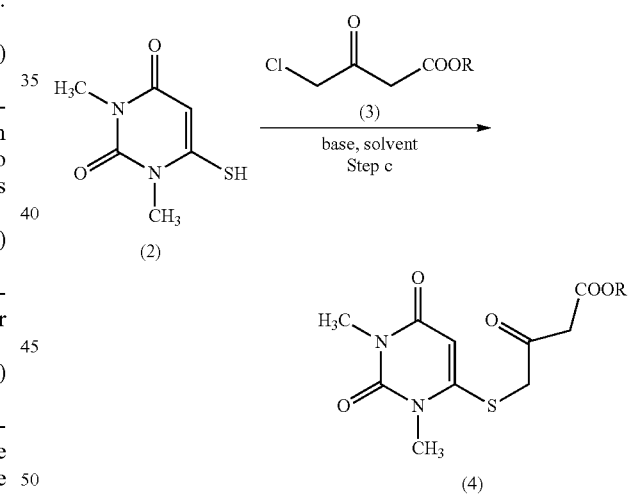

(d) cyclising keto ester of the formula (4) to obtain thieno-pyrimidinyl ester of the formula (5)

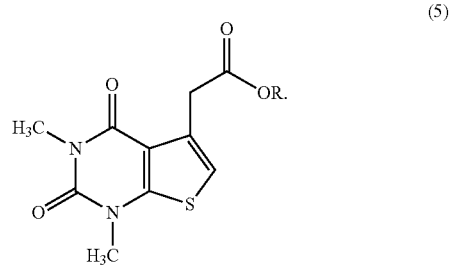

27. N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide having less than about 0.1% (by HPLC) of the compound of formula (III):
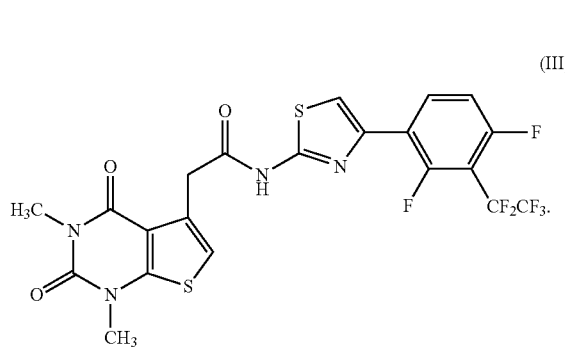
28. A compound of Formula (III)
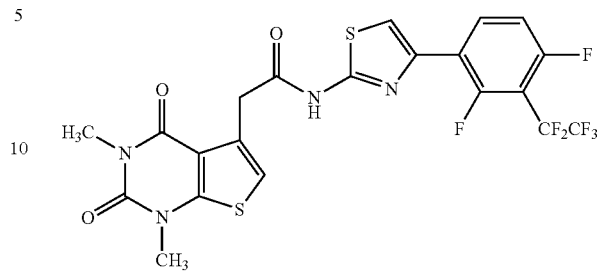
or a pharmaceutically acceptable salt thereof.
* * * * *